US009918776B2

(12) United States Patent
Chen

(10) Patent No.: US 9,918,776 B2
(45) Date of Patent: *Mar. 20, 2018

(54) MULTI-POLE SYNCHRONOUS PULMONARY ARTERY RADIOFREQUENCY ABLATION CATHETER

(71) Applicant: PULNOVO MEDICAL (WUXI) CO., LTD., Wuxi, Jiangsu (CN)

(72) Inventor: Shaoliang Chen, Nanjing (CN)

(73) Assignee: Pulnovo Medical (Wuxi) Co., Ltd., Wuxi (CN)

( * ) Notice: Subject to any disclaimer, the term of this patent is extended or adjusted under 35 U.S.C. 154(b) by 0 days.

This patent is subject to a terminal disclaimer.

(21) Appl. No.: 14/672,013

(22) Filed: Mar. 27, 2015

(65) Prior Publication Data

US 2015/0272668 A1  Oct. 1, 2015

Related U.S. Application Data

(63) Continuation of application No. 14/666,214, filed on Mar. 23, 2015, which is a continuation-in-part of
(Continued)

(30) Foreign Application Priority Data

Nov. 13, 2012 (CN) .......................... 2012 1 0453470
Mar. 27, 2013 (CN) .......................... 2013 1 0103141

(51) Int. Cl.
*A61B 18/14* (2006.01)
*A61B 18/12* (2006.01)
(Continued)

(52) U.S. Cl.
CPC .. *A61B 18/1206* (2013.01); *A61B 17/320068* (2013.01); *A61B 18/00* (2013.01);
(Continued)

(58) Field of Classification Search
CPC ........... A61B 2018/00351; A61B 2018/00357; A61B 2018/00369; A61B 2018/00375;
(Continued)

(56) References Cited

U.S. PATENT DOCUMENTS 5,263,493 A   11/1993  Avitall
5,643,197 A    7/1997  Brucker et al.
(Continued)

FOREIGN PATENT DOCUMENTS

AU    2007290727    1/2012
CN     102119009    7/2011
(Continued)

OTHER PUBLICATIONS

Benza et al. Predicting survival in pulmonary arterial hypertension: insights from the Registry to Evaluate Early and Long-Term Pulmonary Arterial Hypertension Disease Management (REVEAL). Circulation 2010; 122:164-72.
(Continued)

*Primary Examiner* — Jaymi Della
(74) *Attorney, Agent, or Firm* — Wilson, Sonsini, Goodrich & Rosati

(57) ABSTRACT

A multi-pole synchronous pulmonary artery radiofrequency ablation catheter may comprise a control handle, a catheter body and an annular ring. One end of the catheter body may be flexible, and the flexible end of the catheter body may be connected to the annular ring. The other end of the catheter body may be connected to the control handle. A shape memory wire may be arranged in the annular ring. One end of the shape memory wire may extend to an end of the annular ring and the other end of the shape memory wire may pass through a root of the annular ring and be fixed on the flexible end of the catheter body. The annular ring may be provided with an electrode group. The device possesses
(Continued)

advantages of simple operation, short operation time and controllable precise ablation. The device can be used to treat pulmonary hypertension with pulmonary denervation.

15 Claims, 34 Drawing Sheets

Related U.S. Application Data application No. 14/530,588, filed on Oct. 31, 2014, and a continuation-in-part of application No. 14/079,230, filed on Nov. 13, 2013.

(60) Provisional application No. 62/023,781, filed on Jul. 11, 2014.

(51) Int. Cl.
| | |
|---|---|
| A61M 25/01 | (2006.01) |
| A61N 1/06 | (2006.01) |
| A61B 17/32 | (2006.01) |
| A61B 18/00 | (2006.01) |
| A61B 17/00 | (2006.01) |

(52) U.S. Cl.
CPC ..... *A61B 18/1492* (2013.01); *A61M 25/0136* (2013.01); *A61M 25/0147* (2013.01); *A61N 1/06* (2013.01); *A61B 2017/00084* (2013.01); *A61B 2017/00734* (2013.01); *A61B 2017/00867* (2013.01); *A61B 2018/00029* (2013.01); *A61B 2018/00214* (2013.01); *A61B 2018/00345* (2013.01); *A61B 2018/00357* (2013.01); *A61B 2018/00375* (2013.01); *A61B 2018/00404* (2013.01); *A61B 2018/00434* (2013.01); *A61B 2018/00577* (2013.01); *A61B 2018/00613* (2013.01); *A61B 2018/00642* (2013.01); *A61B 2018/00702* (2013.01); *A61B 2018/00791* (2013.01); *A61B 2018/00797* (2013.01); *A61B 2018/00916* (2013.01); *A61B 2018/00988* (2013.01); *A61B 2018/122* (2013.01); *A61B 2018/124* (2013.01); *A61B 2018/144* (2013.01); *A61B 2018/1407* (2013.01); *A61B 2018/1467* (2013.01); *A61B 2218/002* (2013.01)

(58) Field of Classification Search
CPC .. A61B 2018/00386; A61B 2018/1472; A61B 2018/1467; A61B 18/1492
See application file for complete search history.

(56) References Cited

U.S. PATENT DOCUMENTS

| | | | |
|---|---|---|---|
| 5,715,817 A | 2/1998 | Stevens-Wright et al. | |
| 5,782,900 A | 7/1998 | de la Rama et al. | |
| 5,830,214 A | 11/1998 | Flom et al. | |
| 5,833,604 A | 11/1998 | Houser et al. | |
| 5,836,947 A | 11/1998 | Fleischman et al. | |
| 5,913,856 A | 6/1999 | Chia et al. | |
| 5,919,188 A | 7/1999 | Shearon et al. | |
| 5,938,694 A | 8/1999 | Jaraczewski et al. | |
| 6,064,902 A * | 5/2000 | Haissaguerre | A61B 18/1492 600/381 |
| 6,090,104 A | 7/2000 | Webster | |
| 6,096,036 A | 8/2000 | Bowe et al. | |
| 6,115,626 A | 9/2000 | Whayne et al. | |
| 6,123,702 A | 9/2000 | Swanson et al. | |
| 6,198,974 B1 * | 3/2001 | Webster, Jr. | A61M 25/0136 600/146 |
| 6,237,886 B1 | 5/2001 | Katsumata | |
| 6,292,695 B1 | 9/2001 | Webster et al. | |
| 6,411,852 B1 | 6/2002 | Danek et al. | |
| 6,493,589 B1 | 12/2002 | Medhkour et al. | |
| 6,564,096 B2 | 5/2003 | Mest | |
| 6,575,969 B1 | 6/2003 | Rittman, III et al. | |
| 6,690,971 B2 | 2/2004 | Schauerte et al. | |
| 7,260,431 B2 | 8/2007 | Libbus et al. | |
| 7,269,457 B2 | 9/2007 | Shafer et al. | |
| 7,363,076 B2 | 4/2008 | Yun et al. | |
| 7,367,951 B2 | 5/2008 | Bennett et al. | |
| 7,587,238 B2 | 9/2009 | Moffitt et al. | |
| 7,616,990 B2 | 11/2009 | Chavan et al. | |
| 7,623,926 B2 | 11/2009 | Rossing et al. | |
| 7,630,760 B2 | 12/2009 | Libbus et al. | |
| 7,664,548 B2 | 2/2010 | Amurthur et al. | |
| 7,711,430 B2 | 5/2010 | Errico | |
| 7,715,915 B1 | 5/2010 | Ryu et al. | |
| 7,734,355 B2 | 6/2010 | Cohen et al. | |
| 7,744,618 B2 | 6/2010 | Shuros et al. | |
| 7,783,353 B2 | 8/2010 | Libbus et al. | |
| 7,789,877 B2 | 9/2010 | Vanney | |
| 7,801,604 B2 | 9/2010 | Brockway et al. | |
| 7,826,899 B1 | 11/2010 | Ryu et al. | |
| 7,828,795 B2 | 11/2010 | Privitera et al. | |
| 7,899,527 B2 | 3/2011 | Yun et al. | |
| 7,925,342 B2 | 4/2011 | Amurthur et al. | |
| 7,937,147 B2 | 5/2011 | Sih et al. | |
| 8,019,435 B2 | 9/2011 | Hastings et al. | |
| 8,027,724 B2 | 9/2011 | Wei et al. | |
| 8,052,668 B2 | 11/2011 | Sih | |
| 8,073,538 B2 | 12/2011 | Peters et al. | |
| 8,088,127 B2 | 1/2012 | Mayse et al. | |
| 8,249,705 B1 | 8/2012 | Kieval et al. | |
| 9,005,100 B2 | 4/2015 | Gnanashanmugam et al. | |
| 9,028,391 B2 | 5/2015 | Gnanashanmugam et al. | |
| 2001/0031987 A1 | 10/2001 | Saksena et al. | |
| 2002/0065514 A1 | 5/2002 | Rashidi | |
| 2002/0120304 A1 | 8/2002 | Mest | |
| 2005/0004440 A1 * | 1/2005 | Vanney | A61B 18/1492 600/374 |
| 2005/0004565 A1 | 1/2005 | Vanney | |
| 2005/0010095 A1 | 1/2005 | Stewart et al. | |
| 2005/0113822 A1 | 5/2005 | Fuimaono et al. | |
| 2005/0261672 A1 | 11/2005 | Deem et al. | |
| 2005/0283148 A1 | 12/2005 | Janssen et al. | |
| 2006/0041277 A1 | 2/2006 | Deem et al. | |
| 2006/0074272 A1 | 4/2006 | Di Ubaldi | |
| 2006/0116737 A1 | 6/2006 | Libbus | |
| 2006/0167498 A1 | 7/2006 | Dilorenzo | |
| 2006/0217772 A1 | 9/2006 | Libbus et al. | |
| 2006/0241366 A1 * | 10/2006 | Falwell | A61B 5/0422 600/374 |
| 2007/0032835 A1 | 2/2007 | Rittman | |
| 2007/0060921 A1 | 3/2007 | Janssen et al. | |
| 2007/0083193 A1 | 4/2007 | Werneth et al. | |
| 2007/0083194 A1 * | 4/2007 | Kunis | A61B 18/1492 606/41 |
| 2007/0129720 A1 | 6/2007 | Demarais et al. | |
| 2007/0129760 A1 | 6/2007 | Demarais et al. | |
| 2007/0142879 A1 | 6/2007 | Greenberg et al. | |
| 2007/0191904 A1 | 8/2007 | Libbus et al. | |
| 2007/0225641 A1 * | 9/2007 | Schneider | A61M 25/0136 604/93.01 |
| 2007/0255379 A1 | 11/2007 | Williams et al. | |
| 2008/0255642 A1 | 10/2008 | Zarins et al. | |
| 2008/0281312 A1 | 11/2008 | Werneth et al. | |
| 2008/0306570 A1 | 12/2008 | Rezai et al. | |
| 2009/0024124 A1 | 1/2009 | Lefler et al. | |
| 2009/0062873 A1 | 3/2009 | Wu et al. | |
| 2009/0118780 A1 | 5/2009 | Dilorenzo | |
| 2009/0177262 A1 | 7/2009 | Oberti et al. | |
| 2009/0216290 A1 | 8/2009 | Ruse et al. | |
| 2009/0254142 A1 | 10/2009 | Edwards et al. | |
| 2010/0057074 A1 * | 3/2010 | Roman | A61B 18/1492 606/33 |
| 2010/0094196 A1 | 4/2010 | Nash et al. | |
| 2010/0113928 A1 | 5/2010 | Thapliyal et al. | |
| 2010/0114095 A1 | 5/2010 | Janssen et al. | |
| 2010/0137860 A1 | 6/2010 | Demarais et al. | |
| 2010/0152726 A1 | 6/2010 | Cadouri | |

(56) References Cited

U.S. PATENT DOCUMENTS

| | | |
|---|---|---|
| 2010/0168548 A1 | 7/2010 | Govari et al. |
| 2010/0217347 A1 | 8/2010 | Swoyer et al. |
| 2010/0228317 A1 | 9/2010 | Libbus et al. |
| 2010/0241188 A1 | 9/2010 | Errico et al. |
| 2010/0249568 A1 | 9/2010 | Stehr et al. |
| 2010/0249773 A1 | 9/2010 | Clark et al. |
| 2010/0249859 A1 | 9/2010 | Dilorenzo |
| 2010/0268307 A1 | 10/2010 | Demarais et al. |
| 2010/0274221 A1 | 10/2010 | Sigg et al. |
| 2010/0286684 A1 | 11/2010 | Hata et al. |
| 2010/0286734 A1 | 11/2010 | Yun et al. |
| 2010/0298905 A1 | 11/2010 | Simon |
| 2011/0034915 A1 | 2/2011 | Ibrahim et al. |
| 2011/0118725 A1 | 5/2011 | Mayse et al. |
| 2011/0152855 A1 | 6/2011 | Mayse et al. |
| 2011/0178569 A1 | 7/2011 | Parnis et al. |
| 2011/0200171 A1 | 8/2011 | Beetel et al. |
| 2011/0202098 A1 | 8/2011 | Demarais et al. |
| 2011/0207758 A1 | 8/2011 | Sobotka et al. |
| 2011/0257708 A1 | 10/2011 | Kramer et al. |
| 2011/0276103 A1 | 11/2011 | Maile et al. |
| 2011/0301587 A1 | 12/2011 | Deem et al. |
| 2011/0301679 A1 | 12/2011 | Rezai et al. |
| 2012/0029505 A1 | 2/2012 | Jenson |
| 2012/0029509 A1 | 2/2012 | Smith |
| 2012/0029510 A1 | 2/2012 | Haverkost |
| 2012/0029511 A1 | 2/2012 | Smith et al. |
| 2012/0029512 A1 | 2/2012 | Willard et al. |
| 2012/0065554 A1 | 3/2012 | Pikus |
| 2012/0116382 A1 | 5/2012 | Ku et al. |
| 2012/0123258 A1 | 5/2012 | Willard |
| 2012/0123406 A1 | 5/2012 | Edmunds et al. |
| 2012/0143294 A1 | 6/2012 | Clark et al. |
| 2012/0157992 A1 | 6/2012 | Smith et al. |
| 2012/0157993 A1 | 6/2012 | Jenson et al. |
| 2012/0158104 A1 | 6/2012 | Huynh et al. |
| 2012/0165815 A1 | 6/2012 | Collins et al. |
| 2012/0172680 A1 | 7/2012 | Gelfand et al. |
| 2012/0172870 A1 | 7/2012 | Jenson et al. |
| 2012/0184952 A1 | 7/2012 | Jenson et al. |
| 2012/0232551 A1 | 9/2012 | Swanson et al. |
| 2012/0272839 A1 | 11/2012 | Kramer et al. |
| 2012/0277839 A1 | 11/2012 | Kramer et al. |
| 2012/0290024 A1 | 11/2012 | Zhang et al. |
| 2012/0294424 A1 | 11/2012 | Chin et al. |
| 2012/0302909 A1 | 11/2012 | Mayse et al. |
| 2013/0165922 A1 | 6/2013 | Falwell et al. |
| 2013/0204068 A1 | 8/2013 | Gnanashanmugam et al. |
| 2013/0317375 A1 | 11/2013 | Garcia et al. |
| 2014/0180277 A1 | 6/2014 | Chen et al. |
| 2015/0057599 A1 | 2/2015 | Chen |
| 2015/0196357 A1 | 7/2015 | Chen |
| 2015/0201988 A1 | 7/2015 | Chen |
| 2015/0272656 A1 | 10/2015 | Chen |

FOREIGN PATENT DOCUMENTS

| | | |
|---|---|---|
| CN | 102198015 | 9/2011 |
| CN | 102641153 | 8/2012 |
| CN | 102686179 A | 9/2012 |
| CN | 102908191 A | 2/2013 |
| CN | 202982207 U | 6/2013 |
| EP | 0 467 422 | 12/1997 |
| EP | 0916360 A2 | 5/1999 |
| EP | 1 637 086 | 3/2006 |
| RU | 2102090 | 2/1997 |
| RU | 2074645 | 3/1997 |
| SU | 1119663 | 10/1984 |
| SU | 1412745 | 7/1988 |
| SU | 1734708 | 5/1992 |
| WO | WO 93/01862 | 2/1993 |
| WO | WO 99/065561 | 12/1999 |
| WO | WO-0137723 A2 | 5/2001 |
| WO | WO-0137925 A2 | 5/2001 |
| WO | WO 10/110785 | 9/2010 |
| WO | WO 11/075328 | 6/2011 |
| WO | WO 11/091069 | 7/2011 |
| WO | WO-2011139589 A2 | 11/2011 |
| WO | WO 12/068268 | 5/2012 |
| WO | WO 12/120495 | 9/2012 |
| WO | WO 12/149341 | 11/2012 |
| WO | WO 12/149511 | 11/2012 |
| WO | WO 12/154800 | 11/2012 |

OTHER PUBLICATIONS

Brace, Radiofrequency and Microwave Ablation of the Liver . . . ; National Institute of Health/NIH Public Access Author Manuscript; Curr Probl Diagn Radiol. 2009; 38(3); 135-143. doi:10.1067.

Chen et al. Percutaneous pulmonary artery denervation completely abolishes experimental pulmonary arterial hypertension in vivo. EuroIntervention 2013; 9:269-76.

Chen et al. Pulmonary artery denervation to treat pulmonary arterial hypertension: the single-center, prospective, first-in-man PADN-1 study (first-in-man pulmonary artery denervation for treatment of pulmonary artery hypertension). J Am Coll Cardiol 2013; 62:1092-100.

Chinese Clinical Trial Register (ChiCTR): "First-in-Man of Pulmonary artery denervation for treatment of pulmonary artery hypertention: the PADN-1 trial" dated Apr. 6, 2012, http://www.chictr.org/en/proj/show.aspx?proj=2741 (3 pages).

Chinese Clinical Trial Register (ChiCTR): "Percutaneous pulmonary arterial denervation for treatment of chronic heart failure with secondary pulmonary hypertension" dated Nov. 2, 2012, http://www.chictr.org/en/proj/show.aspx? proj=3677 (3 pages).

Chinese Clinical Trial Register (ChiCTR): "Pulmonary Artery Denervation in Patients with Pulmonary Artery Hypertention (The PADN-2 trial): a randomised controlled trial" dated Apr. 12, 2012, http://www.chictr.org/en/proj/show.aspx?proj=2756 (4 pages).

Cruz et al; Cardiopulmonary Effects Following Endoscopic Thoracic Sympathectomy . European Journal of Cardio-Thoracic Surgery, (2009) 491-496, Published by Elsevier BV.

Farber et al. Predicting outcomes in pulmonary arterial hypertension based on the 6-minute walk distance. J Heart Lung Transplant 2014. doi: 10.1016/j.healun.2014.08.020.

Farber et al. Validation of 6-minute walk distance as a surrogate end point in pulmonary arterial hypertension trials. Circulation 2012; 126:258-60.

Flues et al, "Cardiac and pulmonary arterial remodeling after sinoaortic denervation in normotensive rats", dated Jan. 26, 2012, http://www.ncbi.nlm.nih.gov/pubmed/22079748, printed Apr. 28, 2014 (2 pages).

Fritz et al. Baseline and follow-up 6-minute walk distance and brain natriuretic peptide predict 2-year mortality in pulmonary arterial hypertension. Chest 2013; 143:315-23.

Frost et al., Evaluation of the predictive value of a clinical worsening definition using 2-year outcomes in patients with pulmonary arterial hypertension: a RAVEAL registry analysis. Chest 2013; 144:152-9.

Galie et al. A meta-analysis of randomized controlled trials in pulmonary arterial hypertension. Eur Heart J 2009; 30:394-403.

Galie et al. Tadalafil therapy for pulmonary arterial hypertension. Circulation 2009; 119:2894-903.

Galie et al., Guidelines for the diagnosis and treatment of pulmonary hypertension: The Task Force for the Diagnosis and Treatment of Pulmonary Hypertension of the European Society of Cardiology (ESC) and the European Respiratory Society (ERS), endorsed by the International Society of Heart and Lung Transplantation (ISHLT). Eur Heart J 2009; 30:2493-537.

Galiè, New treatment strategies for pulmonary arterial hypertension: hopes or hypes? J Am Coll Cardiol 2013; 62:1101-2.

Garutti et al., Surgical Upper Thoracic Sympathectomy Reduces Arterial Oxygenation. Letters to the Editor, p. 703-4, doi;10.1053/j.jvca.2004.12.008.

Hiremath et al. Exercise improvement and plasma biomarker changes with intravenous treprostinil therapy for pulmonary arterial hypertension: a placebo-controlled trial. J Heart Lung Transplant 2010; 29:137-49.

(56) References Cited

OTHER PUBLICATIONS

Humbert et al. Survival in patients with idiopathic, familial, and anorexigen-associated pulmonary arterial hypertension in the modern management era. Circulation 2010; 122:156-63.
Juratsch et al., Experimental pulmonary hypertension produced by surgical and chemical denervation of the pulmonary vasculature. Chest 1980; 77:525-30.
Lang et al. Recommendations for chamber quantification: a report from the American Society of Echocardiography's Guidelines and Standards Committee and the Chamber Quantification Writting Group. J Am Soc Echocardiogr 2005; 18:1440-63.
McLaughlin et al. Prognosis of pulmonary arterial hypertension: ACCP evidence-based clinical practice guidelines. Chest 2004; 126(Suppl 1):78S-92S.
McLaughlin et al. Randomized study of adding inhaled iloprost to existing bosentan in pulmonary arterial hypertension. Am J Respir Crit Care Med 2006; 174:1257-63.
McLauglin et al. End points and clinical trial design in pulmonary arterial hypertension. J Am Coll Cardiol 2009; 54:S97-107.
Mereles et al. Exercise and respiratory training improve exercise capacity and quality of life in patients with severe chronic pulmonary hypertension. Circulation 2006; 114: 1482-9.
Naeije et al., "Pulmonary vascular responses to surgical chemodenervation and chemical sympathectomy in dogs", dated Jan. 1989, http://www.ncbi.nlm.nih.gov/pubmed/2917946, printed Apr. 28, 2012 (2 pages).
Odero et al; Left Cardiac Sympathetic Denervation for the Prevention of Life-Threatening Arrhythmias . . . ; 2010 Heart Rhythm Society; Aug. 2010, pp. 1161-1165, vol. 7, No. 8.
Ommen et al., Assessment of right atrial pressure with 2-dimensional and Doppler echocradiography: a simultaneous catheterization and cardiographic study. Mayo Clin Proc 2000; 75:24-9.
Savarese et al. Do changes of 6-minute walk distance predict clinical events in patients with pulmonary arterial hypertension? A meta-analysis of 22 randomized trials. J Am Coll Cardiol 2012; 60: 1192-1201.
Tei et al., Noninvasive Doppler-derived myocardial performance index: correlation with simultaneous measurement of cardiac catheterization measurements. J Am Soc Echocardiogr 1997; 10:169-78.
Chen. Pulmonary artery denervaion to treat pulmonary arterial hypertension unresponive to medication: a single-center, prospective, first-in-man PADN1 study. Najing First Hospital, Nanjing Medical University, Nanjing, China. TCT2012. Oct. 22, 2012. 23 pages.
Co-pending U.S. Appl. No. 15/228,358, filed Aug. 4, 2016.
European search report and opinion dated Nov. 18, 2015 for EP Application No. 13840133.
International search report and written opinion dated Aug. 22, 2013 for PCT/CN2013/073338.
International search report and written opinion dated Nov. 23, 2015 for PCT/US2015/039930.
Notice of allowance dated Aug. 16, 2016 for U.S. Appl. No. 14/672,021.
Office action dated Jan. 5, 2015 for U.S. Appl. No. 14/530,588.
Office action dated Jan. 21, 2016 for U.S. Appl. No. 14/672,021.
Office action dated Feb. 4, 2016 for U.S. Appl. No. 14/079,230.
Office action dated Jul. 14, 2015 for U.S. Appl. No. 14/666,214.
Office action dated Jul. 31, 2015 for U.S. Appl. No. 14/530,588.
Office action dated Aug. 5, 2015 for U.S. Appl. No. 14/672,010.
Office action dated Sep. 15, 2015 for U.S. Appl. No. 14/672,021.
Office action dated Oct. 28, 2015 for U.S. Appl. No. 14/666,214.
Office action dated Dec. 21, 2015 for U.S. Appl. No. 14/672,010.
Zhou, et al. Pulmonary Artery Denervation Attenuates Pulmonary Arterial Remodeling in Dogs With Pulmonary Arterial Hypertension Induced by Dehydrogenized Monocrotaline. JACC Cardiovasc Interv. Dec. 28, 2015;8(15):2013-23. doi: 10.1016/j.jcin.2015.09. 015.
Chen, SL. et al., Hemodynamic, functional, and clinical responses to pulmonary artery denervation in patients with pulmonary arterial hypertension of different causes: phase II results from the Pulmonary Artery Denervation-1 study. Circ Cardiovasc Interv. Nov. 2015;8(11):e002837. doi: 10.1161/CIRCINTERVENTIONS.115. 002837.
Chen, SL. et al., Response to Letter Regarding Article, "Hemodynamic, Functional, and Clinical Responses to Pulmonary Artery Denervation in Patients With Pulmonary Arterial Hypertension of Different Causes: Phase II Results From the Pulmonary Artery Denervation-1 Study". Circ Cardiovasc Interv. Jan. 2016;9(1):e003463. doi: 10.1161/CIRCINTERVENTIONS.115. 003463. No abstract available.
Chen,SL. et al., Pericardial effusion is correlated with clinical outcome after pulmonary artery denervation for pulmonary arterial hypertension. Oncotarget. Dec. 20, 2016. doi: 10.18632/oncotarget. 14031. [Epub ahead of print].
Zhang, H. et al., Pulmonary artery denervation for treatment of a patient with pulmonary hypertension secondary to left heart disease. Pulm Circ. Jun. 2016;6(2):240-3. doi: 10.1086/685550.
Zhang, YJ. et al., Pulmonary arterial hypertension: pharmacologic therapies and potential pulmonary artery denervation treatment. EuroIntervention. May 2013;9 Suppl R:R149-54. doi: 10.4244/ EIJV9SRA25. Review.
Notice of Allowance dated Sep. 11, 2017 for U.S. Appl. No. 14/672,010.
Notice of Allowance dated Sep. 14, 2017 and Sep. 22, 2017 for U.S. Appl. No. 14/672,021.
Notice of Allowance dated Sep. 19, 2017 and Sep. 7, 2017 for U.S. Appl. No. 14/666,214.
Notice of Allowance dated Sep. 22, 2017 for U.S. Appl. No. 14/672,021.
Notice of Allowance dated Oct. 13, 2017 for U.S. Appl. No. 14/672,010.
Notice of Allowance dated Oct. 13, 2017 for U.S. Appl. No. 14/666,214.
Notice of Allowance dated Oct. 13, 2017 for U.S. Appl. No. 14/672,021.

\* cited by examiner

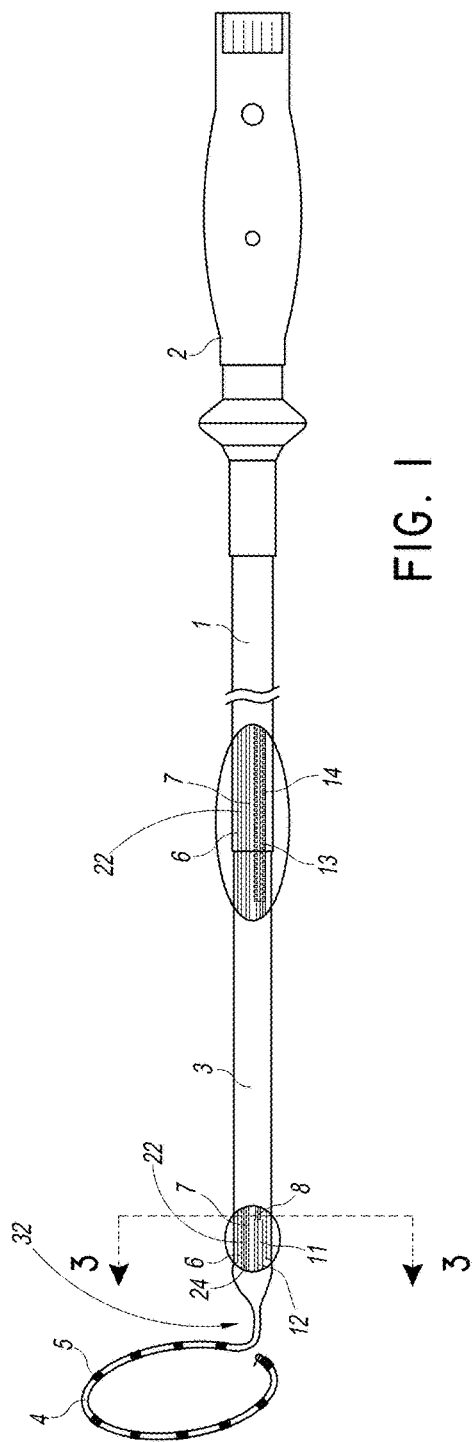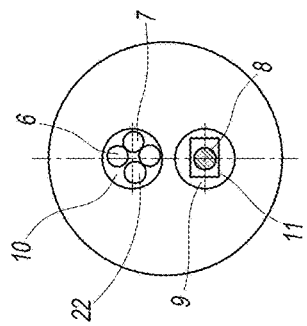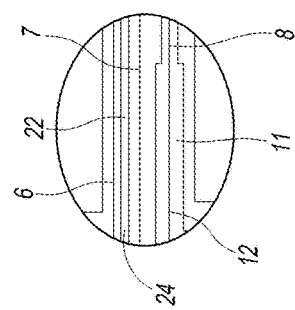

|  | Systolic Pulmonary Artery Pressure (mmHg) | | | Mean Pulmonary Artery Pressure (mmHg) | | |
|---|---|---|---|---|---|---|
| Parameter | Before surgery | during surgery | Decline | Before surgery | during surgery | Decline |
| Parameter Status 1<br>Temperature <50°<br>Energy 8-10W<br>Ablation 120s | 96 | 94 | 2.1% | 56 | 54 | 3.6% |
| Parameter Status 2<br>Temperature 50°~60°<br>Energy 8-10W<br>Ablation 120s | 88 | 64 | 27.3% | 52 | 36 | 31% |
| Parameter Status 3<br>Temperature 40°~45°<br>Energy <8W<br>Ablation 120s | 86 | 86 | 0% | 54 | 53 | 1.9% |
| Parameter Status 4<br>Temperature 50°~60°<br>Energy 8-10W<br>Ablation 60s | 86 | 78 | 9.3% | 54 | 49 | 11.1% |

FIG. 14B

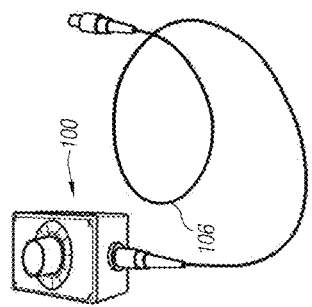
FIG. 15A
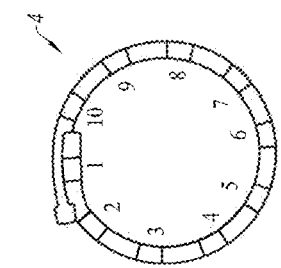
FIG. 15B
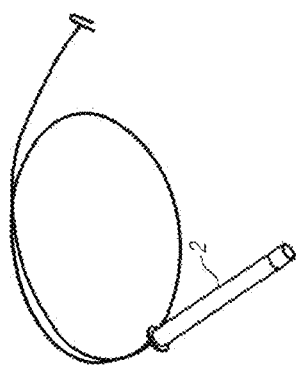
FIG. 15C
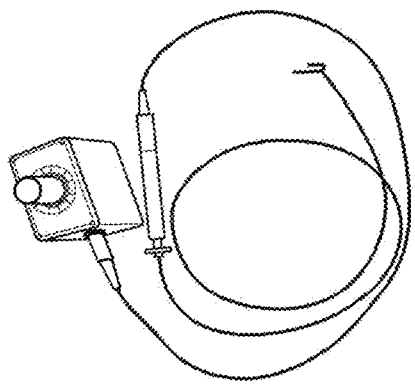
FIG. 15C
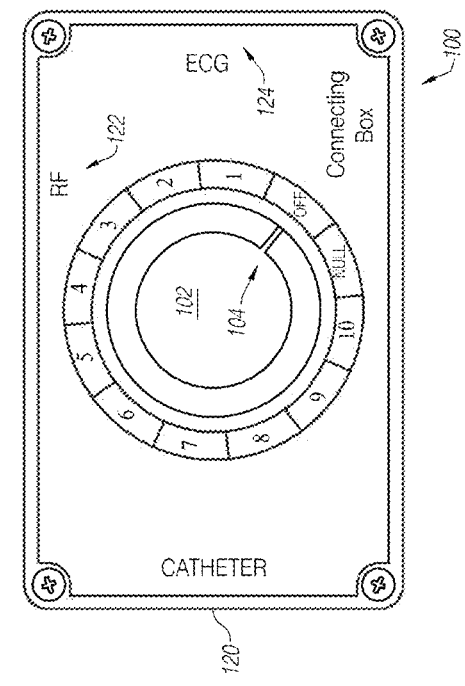
FIG. 15D
FIG. 15E

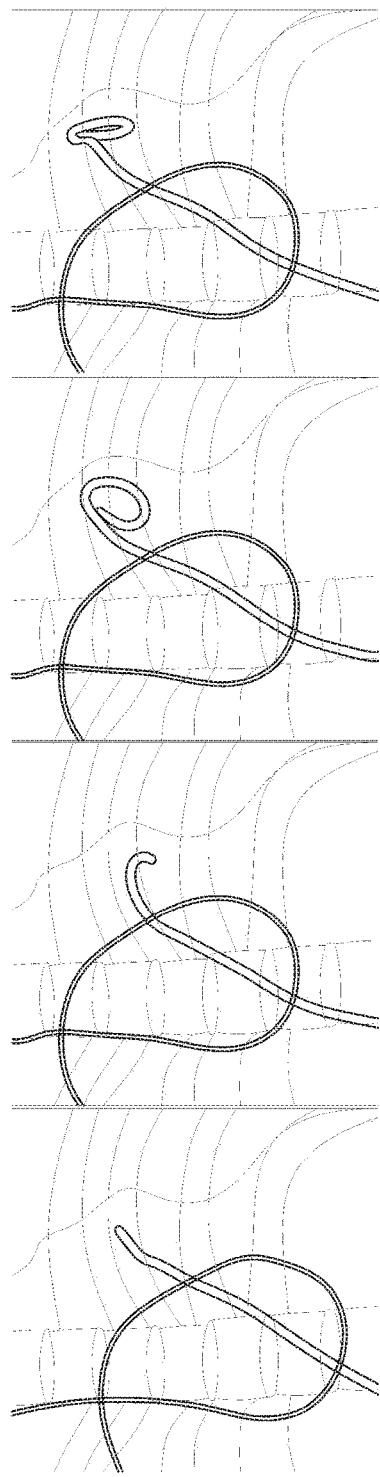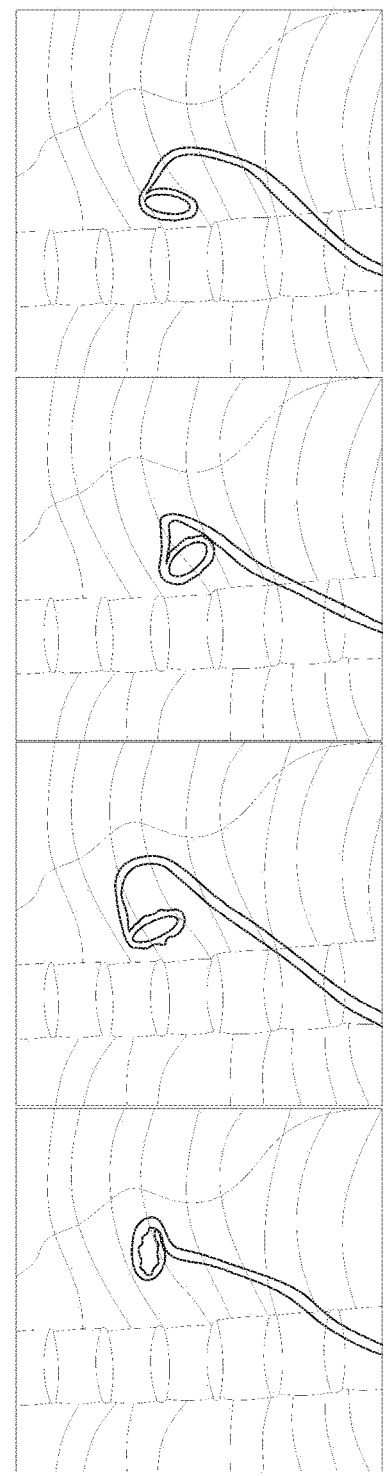

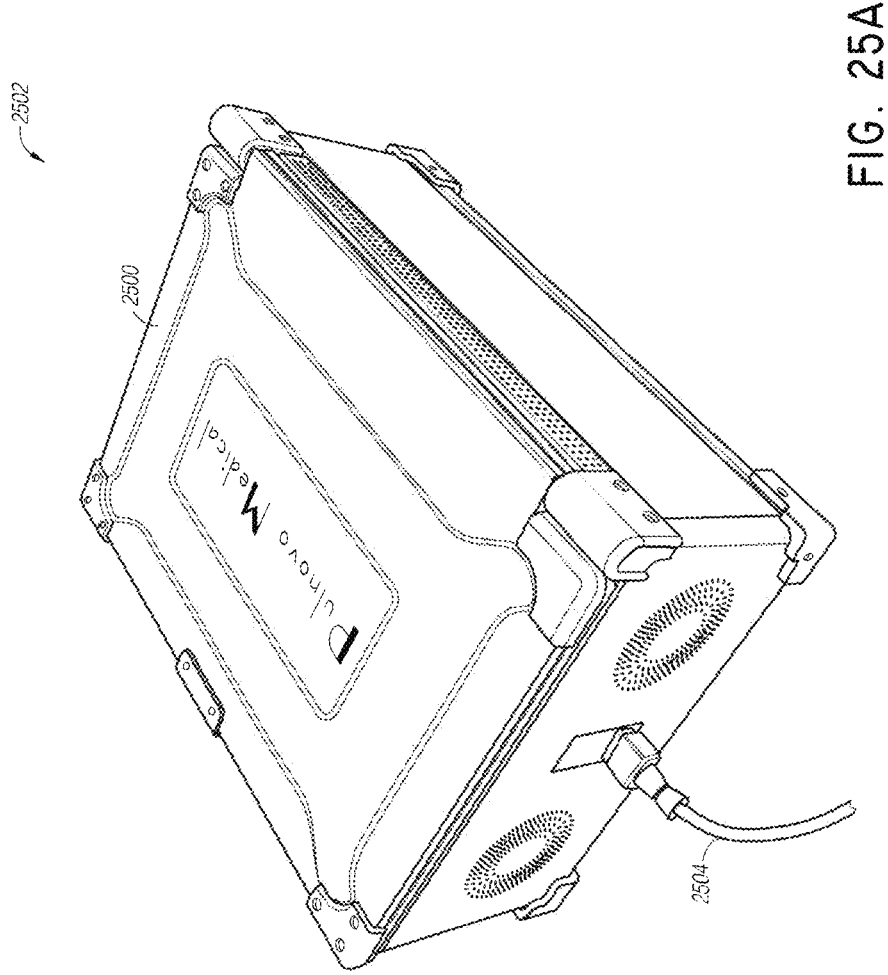

FIG. 25E

MULTI-POLE SYNCHRONOUS PULMONARY ARTERY RADIOFREQUENCY ABLATION CATHETER

CROSS-REFERENCE TO RELATED APPLICATIONS

The present application is a continuation of U.S. application Ser. No. 14/666,214 filed Mar. 23, 2015, which claims priority to U.S. Application Provisional No. 62/023,781 filed on Jul. 11, 2014, the entire contents of each of which are hereby incorporated by reference. U.S. application Ser. No. 14/666,214 is a continuation-in-part application of U.S. application Ser. No. 14/530,588 filed on Oct. 31, 2014, and U.S. application Ser. No. 14/079,230 filed on Nov. 13, 2013, both of which claim priority to Chinese Application No. 201210453470.4 filed on Nov. 13, 2012, and Chinese Application No. 201310103141.1 filed on Mar. 27, 2013, the entire contents of each of which are hereby incorporated by reference.

BACKGROUND OF THE INVENTIONS

Field of the Inventions

The present inventions relate to medical devices for treatment of pulmonary hypertension in the pulmonary artery by de-sympathetic methods, for example, with multi-pole synchronous pulmonary artery radiofrequency ablation catheters, as well as methods for diagnosis and method of treating pulmonary hypertension.

Description of the Related Art

Pulmonary hypertension (PH) is understood to be an intractable disease in the cardiovascular, respiratory, connective tissue, immune and rheumatic systems. Currently available clinical treatments of pulmonary hypertension are limited and therapy efficacy thereof is poor. Incidence of primary pulmonary hypertension is low, but those secondary to pulmonary interstitial fibrosis, connective tissue disease, portal hypertension, chronic pulmonary artery embolism and left heart system disorder are common, with five-year mortality rate up to 30%. Therefore, prevention and treatment for pulmonary hypertension is of great significance.

In recent years, new targeted drugs have emerged based on the research into the pathogenesis of pulmonary hypertension. However, some of those drugs have serious limitations including many side effects, inappropriate dosage form, expensive cost and unreliable efficacy, and thus many have not been widely applied in clinical treatment.

SUMMARY OF THE INVENTIONS

An aspect of at least one of the inventions disclosed herein includes the realization, supported by experimental data which demonstrates, that pulmonary hypertension is associated with hyper sympathetic activity in pulmonary artery and hyperactive baroreceptor. Blocking the sympathetic nerves in the pulmonary artery or permanently damaging the baroreceptor structure and function thereof can decrease the pulmonary artery pressure, which can provide more successful treatments of pulmonary hypertension.

Some embodiments disclosed herein provide a multi-pole synchronous pulmonary artery radiofrequency ablation catheter for treatment of pulmonary hypertension in the pulmonary artery by a de-sympathetic method. In some embodiments, the catheter only heats the adherent tissue rather than the blood. Additionally, in some embodiments, the catheter can be configured to provide cold saline perfusion at or near the ablation site to protect the vascular intima. Some embodiments can also provide advantages of simple operation, short operation time and controllable, precise ablation.

In some embodiments, a multi-pole synchronous pulmonary artery radiofrequency ablation catheter can comprise a control handle, a catheter body and an annular ring. The control handle can be provided with an adjustment apparatus. The catheter body can be hollow and can include a cavity. One or a plurality of lead wires, one or more temperature sensing wires and one or more pull wires can be arranged in the cavity. One end of the catheter body can be flexible. The flexible end can be connected to an annular ring and the other end of the catheter body can be connected to the control handle. One end of the pull wire can be connected to the flexible end and the other end of the pull wire can be connected to the adjustment apparatus. Tension in the pull wire can be adjusted through the adjustment apparatus to achieve shape control, such as curvature control, of the flexible end. A shape memory wire can be arranged in the annular ring. One end of the shape memory wire can extend to the end of the annular ring and the other end of the shape memory wire can pass through the root of the annular ring and can be fixed on the flexible end of the catheter body. The annular ring can be provided with an electrode group with each electrode connected to the one or more lead wires and the one or more temperature sensing wires. The lead wire(s) and the temperature sensing wire(s) extend through the catheter body and are electrically connected to the control handle.

An infusion tube can be arranged in the cavity of the catheter body and a through hole can be arranged on one or more of the electrodes. The infusion tube can be connected to the electrodes through the annular ring. The transfused fluid flows out from the through hole and thus can be used for cooling purposes during ablation as part of the percutaneous pulmonary denervation (PADN) procedure.

The electrodes on the annular ring can be made of material selected from a group consisting of platinum-iridium alloy, gold, stainless steel and nickel alloy, with the number in the range of 3-30 electrodes, a diameter in the range of 1.3-2.0 mm, a length in the range of 1.2-4 mm and an edge space between adjacent electrodes in the range of 0.5-10 mm.

The flexible end of the catheter body can be provided with a counterbore, an inner diameter of the counterbore can be sized to fit an outer diameter of the root of the annular ring, and thus the root of the annular ring can be inserted and fixed into the counterbore.

The flexible end of the catheter body is provided with a groove in which a connector is arranged, one end of the connector is connected to the pull wire and the other end of the connector is connected to the shape memory wire.

The material of the shape memory wire in the annular ring can be a shape memory alloy selected from a group consisted of nickel-titanium alloy, stainless steel or titanium, with a diameter of 0.25-0.5 mm. The diameter of the annular ring can be 12-40 mm. For example, the annular ring can be configured so as to be biased toward a circumferential shape, having a desired diameter (e.g., in the range of 12-40 mm), for example, with the use of a memory shape material. Preferably, 10 electrodes are arranged on the annular ring. The width of naked section of the electrode is 0.75 mm, and the space therebetween is 5 mm.

The flexible end can be made of medical polymer materials with a length in the range of 30-80 mm. The connection can be achieved by a UV-curing adhesive. The joint between the flexible end and the annular ring can be sealed.

The pull wire is made of stainless steel or nickel-titanium alloy. The outside of pull wire is provided with a spring coil, and the outside of the spring coil is provided with a spring sleeve made of polyimide material.

In some embodiments, the catheter can be packaged into a kit including a plurality of different annular rings that are biased to different diameters. In some embodiments, where the annular rings, flexible bodies, and handles are permanently connected together, a kit can include a plurality of different catheters, each having handles and flexible bodies, but differently sized annular rings.

In some embodiments and/or methods of use, the catheter can heat, with radiofrequency energy, the tissue in direct contact with the electrode and avoid heating blood. Additionally, the catheter can provide advantages of simple operation, short operation time and controllable precise ablation. The catheter body can preferably be made of a polymer material, which is a poor heat conductor, so that it can avoid transmitting the heat when heating the electrodes to the flowing blood contacting the catheter body, thereby effectively avoid heating the blood.

Furthermore, the shape or curvature of the flexible end can be adjusted by operating the adjustment apparatus, which allows the operator to control the handle with one hand, so as to easily adjust the curvature of the flexible end for purposes of placement of the annular ring and the electrodes. As such, after achieving the desired placement, the electrodes on the annular ring can be pressed against the pulmonary artery and achieve ablation of pulmonary artery intima. During application of the radiofrequency current, the electrodes can produce high local temperature and cause severe damage on the vascular intima.

Thus, in some embodiments, the catheter can be configured to provide cold saline perfusion to cool down the local temperature. When the electrodes receive current, the saline is automatically and uniformly diffused through the through holes, which can provide beneficial cooling, for example, decreasing the local temperature to be below 60° C., thereby protecting the vascular intima.

In some embodiments, a multi-pole synchronous pulmonary artery radiofrequency ablation catheter may comprise a control handle, a catheter body and an annular ring. The control handle may include an adjustment apparatus. The catheter body may be hollow and comprise a cavity arranged in the catheter body. A lead wire, a temperature sensing wire and a pull wire may be arranged in the cavity. One end of the catheter body may be flexible, and the flexible end of the catheter body may be connected to the annular ring. The other end of the catheter body may be connected to the control handle. One end of the pull wire may be connected to the flexible end. The other end of the pull wire may be connected to the adjustment apparatus on the control handle. The adjustment apparatus may adjust the tension of the pull wire to change a curvature of the flexible end. A shape memory wire may be arranged in the annular ring. One end of the shape memory wire may extend to an end of the annular ring and the other end of the shape memory wire may pass through a root of the annular ring and be fixed on the flexible end of the catheter body. The annular ring may be provided with an electrode group. The electrode group may comprise a first electrode of a first length, a second electrode of a second length different than the first length, and a third electrode. Each electrode of the electrode group may be connected to the lead wire and temperature sensing wire. The lead wire and the temperature sensing wire may go through the catheter body and be electrically connected to the control handle.

The annular ring may extend from the root of the annular ring to the end of the annular ring and comprise a curve of less than 360 degrees. The annular ring may extend from the root of the annular ring to the end of the annular ring and comprise a curve of more than 270 degrees. The annular ring may comprise a first diameter and a second diameter different than the first diameter. The first diameter may be at least 25 mm and the second diameter may be at least 20 mm.

The electrodes of the electrode group may be substantially coplanar. The first length of the first electrode may be least 4 mm. The second length of the second electrode may be least 3 mm. The third electrode may comprise a third length different than the first length and different than the second length. The third length may be at least 2 mm.

In some embodiments, a catheter may comprise a catheter body and an annular ring. One end of the catheter body may be flexible and connected to the annular ring. The curve of the annular ring may be less than 360 degrees and greater than 270 degrees.

The annular ring may be provided with an electrode group comprising a first electrode of a first length, a second electrode of a second length different than the first length, and a third electrode of a third length different than the first length and different than the second length. The electrodes of the electrode group may be substantially coplanar and arranged along a curve of the annular ring that extends from a root of the annular ring to an end of the annular ring. The first length may be least 4 mm. The second length may be least 3 mm and may be less than the first length. The third length may be least 2 mm and may be less than the second length. The first length may be 4 mm. The electrode group may comprise less than four electrodes.

The first electrode may be separated from the second electrode and the third electrode by an equal distance. The equal distance may be 1 mm. The first electrode may be farther in distance from a root of the annular ring than the second electrode and the third electrode.

In some embodiments, a controller may comprise a housing, an electronic display, a battery, an electronic data store, and a computing device. The housing may comprise a catheter connection port disposed along a surface of the housing. The connection port may be configured to interface with a catheter. The catheter may comprise a first electrode of a first length, and a second electrode of a second length different than the first length. The housing may comprise an electronic display disposed along the surface of the housing. The housing may envelop a battery, an electronic data store and a computing device. The electronic display may be configured to present a user interface. The battery may be configured to store power at a level sufficient for ablation using the first electrode, or the second electrode. The electronic data store may comprise stored patient profiles characterizing a plurality of patients. The computing device may comprise one or more processors. The computing device may be in communication with the electronic data store, the electronic display and the battery. The computing device may be configured to at least: receive a selection of a first patient profile of the stored patient profiles from the user interface, display information characterizing the first patient profile on the user interface, receive a selection of the first electrode from the user interface, direct power from the battery at the level sufficient for ablation using the first electrode to the first electrode, receive a selection of the second electrode from the user interface, and direct power from the battery at the level sufficient for ablation using the second electrode to the second electrode.

The computing device may be configured to direct power from the battery to the first electrode and direct power from the battery to the second electrode at a same time. The computing device may be configured to direct power from the battery to the first electrode and direct power from the battery to the second electrode at different times. The computing device may be configured to interrupt power directed from the battery to the first electrode and direct power from the battery to the second electrode after the power directed from the battery to the first electrode is interrupted. The computing device may be configured to direct power from the battery to the first electrode after the battery has finished charging. The computing device may be configured to display on the user interface first electrode ablation information captured by the first sensor while the first electrode receives power from the battery. The computing device may be configured to store the first electrode ablation information with the first patient profile. The computing device may be configured to display on the user interface first electrode ablation information captured by the first sensor while the first electrode receives power from the battery and second electrode ablation information captured by the second sensor while the second electrode receives power from the battery. The second electrode ablation information may be displayed on the user interface after the first electrode stops receiving power from the battery.

The housing may comprise a power connection port configured to receive power at a level sufficient to charge the battery.

The catheter may comprise a first sensor connected with the first electrode. The catheter may comprise a first sensor connected with the first electrode and a second sensor connected with the second electrode.

In some embodiments, a computer-implemented method, under control of one more computing devices executing specific computer executable instructions, may comprise receiving a selection of a first patient profile of a plurality of stored patient profiles from a user interface presented on an electronic display disposed across a surface of a housing. The method may comprise displaying information characterizing the first patient profile on the user interface. The method may comprise receiving a selection of the first electrode from the user interface. The method may comprise directing power from a battery at the level sufficient for ablation using the first electrode to the first electrode, the battery configured to store power at a level sufficient for ablation using the first electrode. The method may comprise receiving a selection of the second electrode from the user interface. The method may comprise directing power from the battery at the level sufficient for ablation using the second electrode to the second electrode. The battery may be configured to store power at a level sufficient for ablation using the second electrode. The housing may comprise a catheter connection port disposed along a surface of the housing. The connection port may be configured to interface with a catheter comprising a first electrode of a first length, and a second electrode of a second length different than the first length. The housing may envelop the battery, an electronic data store and the one or more computing devices executing specific computer executable instructions. The electronic data store may comprise the plurality of stored patient profiles characterizing a plurality of patients.

The first electrode and the second electrode may be configured to convert the power from the battery to radiofrequency (RF) energy for ablation of sympathetic nerve fibers. The first electrode and the second electrode may be configured to convert the power from the battery to ultrasonic energy for ablation of sympathetic nerve fibers. The first electrode and the second electrode is configured to convert the power from the battery to electroporation energy for ablation of sympathetic nerve fibers. The first electrode and the second electrode may be configured to convert the power from the battery to ionizing energy for ablation of sympathetic nerve fibers.

In some embodiments, a computer-readable, non-transitory storage medium storing computer executable instructions that, when executed by one or more computer systems, configure the one or more computer systems to perform operations comprising receiving a selection of a first patient profile of a plurality of stored patient profiles from a user interface presented on an electronic display disposed across a surface of a housing. The operations may comprise displaying information characterizing the first patient profile on the user interface. The operations may comprise receiving a selection of the first electrode from the user interface. The operations may comprise directing power from a battery at the level sufficient for ablation using the first electrode to the first electrode. The battery may be configured to store power at a level sufficient for ablation using the first electrode. The operations may comprise receiving a selection of the second electrode from the user interface. The operations may comprise directing power from the battery at the level sufficient for ablation using the second electrode to the second electrode. The battery may be configured to store power at a level sufficient for ablation using the second electrode.

The housing may comprise a catheter connection port disposed along a surface of the housing. The connection port may be configured to interface with a catheter comprising a first electrode of a first length, and a second electrode of a second length different than the first length. The housing may envelop the battery, an electronic data store and the one or more computer systems. The electronic data store may comprise the plurality of stored patient profiles characterizing a plurality of patients.

The directing power from the battery to the second electrode may be performed by switching power directed from the battery from the first electrode to the second electrode. The directing power from the battery to the second electrode may direct an amount of power greater than an amount of power directed from the battery to the first electrode.

In some embodiments, a multi-pole synchronous pulmonary artery radiofrequency ablation catheter comprises a control handle, a catheter body and an annular ring. The control handle may comprise an adjustment apparatus. The catheter body may be hollow and comprising a cavity arranged in the catheter body. One end of the catheter body may be flexible. The flexible end may be connected to the annular ring. The other end of the catheter body may be connected to the control handle. One end of the pull wire may be connected to the flexible end, and the other end of the pull wire may be connected to the adjustment apparatus on the control handle. The adjustment apparatus may adjust the tension of the pull wire to change a curvature of the flexible end. A shape memory wire may be arranged in the annular ring. One end of the shape memory wire may extend to an end of the annular ring and the other end of the shape memory wire may pass through a root of the annular ring and be fixed on the flexible end of the catheter body. The annular ring may be shaped with an oval comprising a major axis and a minor axis. The major axis may comprise a first diameter along the major axis longer than a second diameter along the minor axis. The annular ring, extending from the root of the annular ring to the end of the annular ring, may comprise a curve of less than 360 degrees. The annular ring may an electrode that straddles the apex of the major axis.

In some embodiments, a catheter comprises a catheter body and an annular ring. One end of the catheter body may be flexible and connected to the annular ring. The annular ring may be oval shaped.

The annular ring may comprise a major axis and a minor axis, the major axis comprising a first diameter along the major axis longer than a second diameter along the minor axis. The first diameter may be 5 mm longer than the second diameter. The major axis may be along a first axis of symmetry and the minor axis may be along a second axis of symmetry. The annular ring may comprise an electrode that straddles the apex of the major axis. The annular ring may be orthogonal to the end of the catheter body that is flexible. The annular ring may be planar. The annular ring may comprise a curve of less than 360 degrees. The annular ring may comprise a curve of less than 360 degrees and greater than 270 degrees.

The annular ring may comprise an electrode group comprising a first electrode of a first length, a second electrode of a second length different than the first length, and a third electrode of a third length different than the first length and different than the second length. The electrodes of the electrode group may be substantially coplanar. The first length may be least 4 mm. The second length may be least 3 mm and may be less than the first length. The third length may be least 2 mm and may be less than the second length. The first length may be 4 mm. The first electrode may be separated from the second electrode and the third electrode by an equal distance.

In some embodiments, a method of performing pulmonary denervation may comprise positioning an ablation device in a pulmonary artery trunk of a live animal. The pulmonary artery trunk may include a distal portion of a main pulmonary artery, a proximal portion of a left pulmonary artery, and a proximal portion of a right pulmonary artery. The method may comprise deploying an annular ring from the ablation device. The annular ring may comprise a major axis and a minor axis. The major axis may comprise a first diameter along the major axis longer than a second diameter along the minor axis. The method may comprise ablating at least one of the distal portion of the main pulmonary artery, the proximal portion of the left pulmonary artery and the proximal portion of the right pulmonary artery.

In some embodiments, a controller may comprise a housing, an electronic display, an electronic data store, and a computing device. The housing may comprise a connection port disposed along a surface of the housing. The connection port may be configured to interface with a catheter comprising a first electrode of a first length, and a second electrode of a second length different than the first length. The electronic display may be disposed along the surface of the housing. The housing may envelop the electronic data store and the computing device. The electronic display may be configured to present a user interface. The electronic data store may comprise stored patient profiles characterizing a plurality of patients. The computing device may comprise one or more processors. The computing device may be in communication with the electronic data store and the electronic display. The computing device may be configured to at least receive a selection of a first patient profile of the stored patient profiles from the user interface, display information characterizing the first patient profile on the user interface, and direct power at a first power level sufficient for ablation using the first electrode to the first electrode. The first power level may be based on the first patient profile. The power may be directed from a power source. The power source may be a battery. The power source may be a wall socket connected to a power grid.

The catheter may comprise a second electrode of a second length different than the first length. The computing device may be configured to direct power at a second power level sufficient for ablation using the second electrode to the second electrode. The second power level may be based on the first patient profile. The second power level may be different than the first power level.

The housing may envelop the battery. The battery may be configured to store power at the first power level sufficient for ablation using the first electrode. The computing device may be in communication with the battery and configured to direct power from the battery at the first power level sufficient for ablation using the first electrode to the first electrode. The housing may comprise a power connection port configured to receive power at a level sufficient to charge the battery. The computing device may be configured to direct power from the battery to the first electrode after the battery has finished charging. The computing device may be configured to direct power to the first electrode before the battery has finished charging.

The catheter may comprise a first sensor connected with the first electrode. The computing device may be further configured to display on the user interface first electrode ablation information captured by the first sensor while the first electrode receives power from the battery. The computing device may be further configured to store the first electrode ablation information with the first patient profile. The first electrode ablation information may comprise a temperature. The catheter may comprise an annular ring shaped with an oval comprising a major axis and a minor axis. The major axis may comprise a first diameter along the major axis longer than a second diameter along the minor axis. The first electrode may straddle the apex of the major axis.

In some embodiments, a computer-implemented method may be under control of one more computing devices executing specific computer executable instructions. The method may comprise receiving a selection of a first patient profile, displaying information characterizing the first patient profile on a user interface, receiving a selection of the first patient profile from the user interface, determining, from the first patient profile, a first power level sufficient for ablation using a first electrode, and directing power at the first power level to the first electrode.

The first patient profile may be part of a plurality of stored patient profiles from the user interface presented on an electronic display disposed across a surface of a housing. The housing may comprise a catheter connection port disposed along a surface of the housing. The connection port may be configured to interface with a catheter comprising the first electrode. The housing may envelop an electronic data store and the one or more computing devices executing specific computer executable instructions. The electronic data store may comprise the plurality of stored patient profiles characterizing a plurality of patients.

The first electrode may be configured to convert the power to radiofrequency (RF) energy for ablation of sympathetic nerve fibers. The first electrode may be configured to convert the power to ultrasonic energy for ablation of sympathetic nerve fibers. The first electrode may be configured to convert the power to electroporation energy for ablation of sympathetic nerve fibers. The first electrode may be configured to convert the power to ionizing energy for ablation of sympathetic nerve fibers.

In some embodiments, a computer-readable, non-transitory storage medium storing computer executable instructions that, when executed by one or more computer systems, configure the one or more computer systems to perform operations comprising receiving a selection of a first patient profile of a plurality of stored patient profiles from a user interface presented on an electronic display disposed across a surface of a housing, displaying information characterizing the first patient profile on the user interface, receiving a selection of the first patient profile from the user interface, determining, from the first patient profile, a first power level sufficient for ablation using the first electrode, determining, from the first patient profile, a second power level sufficient for ablation using the second electrode, directing power at the first power level to the first electrode, and directing power at the second power level to the second electrode.

The housing may comprise a catheter connection port disposed along a surface of the housing. The connection port may be configured to interface with a catheter comprising a first electrode of a first length, and a second electrode of a second length different than the first length. The housing may envelop an electronic data store and the one or more computer systems. The electronic data store may comprise the plurality of stored patient profiles characterizing a plurality of patients. The directing power to the second electrode may direct an amount of power greater than an amount of power directed to the first electrode.

In some embodiments, a controller may comprise a housing, a user interface, an electronic data store, and a computing device including one or more processors, the computing device in communication with the electronic data store, and the user interface. The housing may comprise a connection port disposed along the surface of the housing, a user interface disposed along the surface of the housing. The housing may envelop the electronic data store and the computing device. The connection port may be configured to interface with a catheter comprising a first electrode of a first length, and a second electrode of a second length different than the first length. The computing device may be configured to at least receive a selection of the first electrode from the user interface, direct power at a first power level sufficient for ablation using the first electrode to the first electrode, receive a selection of the second electrode from the user interface, and direct power at a second power level sufficient for ablation using the second electrode to the second electrode.

The computing device may be configured to direct power to the first electrode and direct power to the second electrode at a same time. The computing device may be configured to direct power to the first electrode and direct power to the second electrode at different times. The computing device may be is configured to interrupt power directed to the first electrode and direct power to the second electrode after the power directed from the battery to the first electrode is interrupted.

The catheter may comprise an annular ring shaped with an oval comprising a major axis and a minor axis. The major axis may comprise a first diameter along the major axis longer than a second diameter along the minor axis. The first electrode may straddle the apex of the major axis.

The controller may comprise a battery configured to store power at the first power level sufficient for ablation using the first electrode or the second power level sufficient for ablation using the second electrode. The housing may envelop the battery. The computing device may be in communication with the battery and configured to direct power from the battery at the first power level sufficient for ablation using the first electrode, and direct power from the battery at the second power level sufficient for ablation using the second electrode. The housing may comprise a power connection port configured to receive power at a level sufficient to charge the battery. The computing device may be configured to direct power from the battery to the first electrode after the battery has finished charging. The computing device may be configured to direct power from the battery to the second electrode after the battery has finished charging.

The catheter may comprise a first sensor connected with the first electrode. The computing device may be further configured to display on the user interface first electrode ablation information captured by the first sensor while the computing device directs power to the first electrode. The catheter may comprise a first sensor connected with the first electrode and a second sensor connected with the second electrode. The computing device may be configured to display on the user interface first electrode ablation information captured by the first sensor while the computing device directs power to the first electrode and second electrode ablation information captured by the second sensor while the computing device directs power to the second electrode. The second electrode ablation information may be displayed on the user interface after the computing device stops directing power to the first electrode.

In some embodiments, a computer-implemented method may, under control of one more computing devices executing specific computer-executable instructions, comprise receiving a selection of a first electrode on a user interface disposed across a surface of a housing, directing power at a first power level sufficient for ablation using the first electrode to the first electrode, receiving a selection of the second electrode from the user interface, and switching from directing power to the first electrode to directing power at a second power level sufficient for ablation using the second electrode to the second electrode. The housing may comprise a connection port disposed along a surface of the housing, the connection port configured to interface with a catheter comprising the first electrode (which may be of a first length), and the second electrode (which may be of a second length different than the first length). The housing may envelop an electronic data store and the one or more computing devices executing specific computer-executable instructions.

The switching may be performed using a mechanical switch that comprises at least one moving part. The user interface may be a rotatable knob. The switching may be performed using a switching system comprising a mechanical switch that comprises at least one moving part, and a solid state switch that comprises no moving parts.

In some embodiments, a computer-readable, non-transitory storage medium storing computer executable instructions that, when executed by one or more computer systems, may configure the one or more computer systems to perform operations. The operations may comprise receiving a selection of a first electrode from a user interface presented on an electronic display disposed across a surface of a housing, directing power at a first power level sufficient for ablation using the first electrode to the first electrode, receiving a selection of the second electrode from the user interface, and switching from directing power to the first electrode to directing power at a second power level sufficient for ablation using the second electrode to the second electrode. The housing may comprise a connection port disposed along the surface of the housing. The connection port may be configured to interface with a catheter comprising the first electrode (of a first length), and the second electrode (of a second length different than the first length). The housing may envelop an electronic data store and the one or more computer systems. The switching may be performed by controlling a solid state switch that comprises no moving parts.

BRIEF DESCRIPTION OF THE DRAWINGS

FIG. 1 is a schematic structural diagram of an embodiment of a catheter in accordance with an embodiment;

FIG. 2 is a partially enlarged view of Part B identified in FIG. 1;

FIG. 3 is schematic sectional view taken along line A-A' of FIG. 1;

FIG. 14B is a table showing reductions in pulmonary artery pressure (PAP) resulting from the use of different ablation operating parameters;

FIG. 15A is a perspective view of a catheter that can be used to perform pulmonary denervation;

FIG. 15B is an enlarged end view of a distal end of the catheter of FIG. 15A with indicia indicating positions of ten (10) RF electrodes;

FIG. 15C is a perspective view of a controller that can be used for controlling the catheter of FIG. 15A during an ablation procedure;

FIG. 15D is a top plan view of the controller of FIG. 15C;

FIG. 15E is a perspective view of the controller connected to the catheter of FIG. 15A;

FIG. 16A is a fluoroscope image of a sheath device inserted into the main pulmonary artery for guiding the catheter of FIG. 15A into the main pulmonary artery;

FIGS. 16B and 16C are additional fluoroscope images of the catheter of FIG. 15A having been inserted and expanded within the left pulmonary artery of a human patient;

FIG. 16D illustrates a position used for ablation and arterial denervation of the left pulmonary artery of the patient;

FIG. 16E illustrates the catheter of FIG. 15A being positioned within the main pulmonary artery of the patient in a position used for ablation;

FIGS. 16F and 16G illustrate the catheter of FIG. 15A being positioned in the proximal right pulmonary artery and being pushed (FIG. 16F) and pulled (FIG. 16G) to determine if the catheter is properly seated for purposes of ablation;

FIG. 16H is a fluoroscope image of the catheter of FIG. 15A in a position for performing ablation in a proximal portion of the right pulmonary artery;

FIGS. 25A-25H are various perspective views and user interface screenshots of a digital ablation controller.

DETAILED DESCRIPTION OF THE PREFERRED EMBODIMENTS

Figure 4:
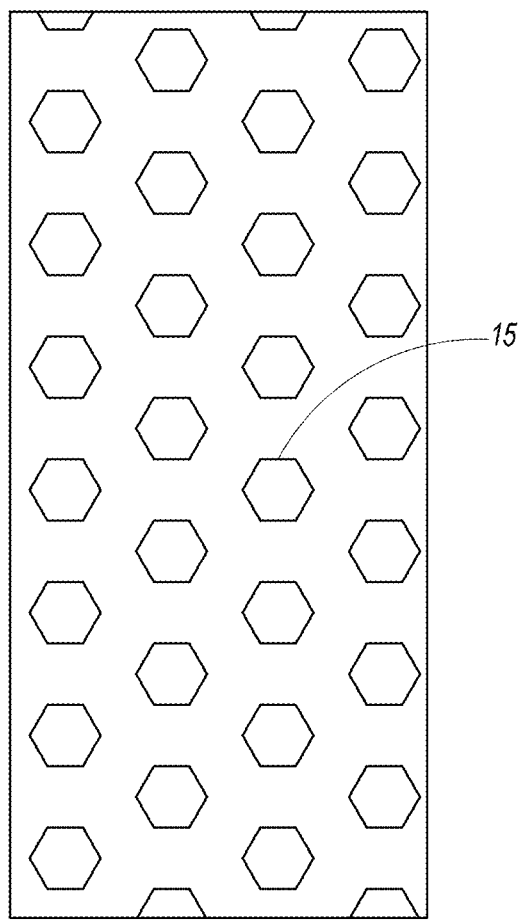
FIG. 4 is a schematic structural view of an optional outer surface of an electrode that can be used with the catheter of FIG. 1.

The following examples further illustrate embodiments of the present inventions, but should not be considered as to limit the present inventions. Without departing from the spirit and essence of, the present inventions, modification or replacement of the method, steps or conditions of the embodiments disclosed below still falls in the scope of the present inventions.

If not otherwise specified, the technical means used in the embodiments are conventional means well known by a person skilled in the art.

EXAMPLE 1

Through the example below and with reference to FIGS. 1-3, some of the technical solutions that can be achieved by various embodiments are further described below.

In some embodiments, a multi-pole synchronous pulmonary artery radiofrequency ablation catheter for de-sympathetic ablation in the pulmonary artery can include a catheter body 1 that has a distal end and a proximal end. The distal end can be provided with a flexible end 3 and the proximal end can be provided with a control handle 2. A pull wire can extend in the catheter body.

Preferably, the catheter body can be made of a polymer material, which is a poor heat conductor, so that it can avoid transmitting or reducing the amount of heat transferred from the electrodes to the blood flow contacting the catheter body, and thereby can better prevent the electrode from heating the blood flow.

The flexible end 3 can include a proximal end and a distal end. An annular ring 4 can be arranged on the distal end. The flexible end 3 can be soft relative to the rest of the catheter body. The annular ring 4 can be provided with a plurality of electrodes 5, wherein each electrode 5 can be configured to sense or extract neural electrical signals, sense temperature and conduct ablation. Each of the electrodes can be connected to lead wires and temperature sensing wires, which extend through the catheter body to the control handle, thus is electrically connected to the control handle. One or more temperature sensing wires can be embedded under each electrode for precise monitoring of the temperature during ablation. Additionally, in some embodiments, the temperature sensing wires can be connected to a thermocouple connected to an inner facing side of the electrodes 5, or can include integrated thermocouples. Other configurations can also be used.

In accordance with several embodiments, ablation may be performed by the electrodes 5 using radiofrequency (RF) energy to ablate sympathetic nerve fibers to cause neuromodulation or disruption of sympathetic communication. In some embodiments, the electrodes 5 may use ultrasonic energy to ablate sympathetic nerve fibers. In some embodiments, the electrodes 5 use ultrasound (e.g., high-intensity focused ultrasound or low-intensity focused ultrasound) energy to selectively ablate sympathetic nerve fibers. In other embodiments, the electrodes 5 use electroporation to modulate sympathetic nerve fibers.

However, the electrodes 5, as used herein, shall not be limited to causing ablation, but also include devices that facilitate the modulation of nerves (e.g., partial or reversible ablation, blocking without ablation, or stimulation). In some embodiments, the catheter may use agents offloaded at the location of the electrodes 5 to nerve fibers to modulate the nerve fibers (e.g., via chemoablation). Chemical agents used with chemoablation (or some other form of chemically-mediated neuromodulation) may, for example, include phenol, alcohol, or any other chemical agents that cause chemoablation of nerve fibers. In some embodiments, cryotherapy is used. For example, the catheter may use agents offloaded at the location of the electrodes 5 for cryoablation to selectively modulate (e.g., ablate) sympathetic nerve fibers. In other embodiments, the catheter may use brachytherapy to modulate the nerve fibers. The catheter may further utilize any combination of RF energy, microwave energy, ultrasonic energy, focused ultrasound (e.g., HIFU, LIFU) energy, ionizing energy (such as X-ray, proton beam, gamma rays, electron beams, and alpha rays), electroporation, drug delivery, chemoablation, cryoablation, brachytherapy, or any other modality to cause disruption or neuromodulation (e.g., ablation, denervation, stimulation) of autonomic (e.g., sympathetic or parasympathetic) nerve fibers.

In accordance with some embodiments, the neuromodulation system is used to modulate or disrupt sympathetic nerve fibers at one or more locations or target sites. For example, the catheter may perform ablation in a circumferential or radial pattern (such as by using the annular ring 4), and/or the catheter may perform ablation at a plurality of points linearly spaced apart along a vessel length. In other embodiments, the catheter performs ablation at one or more locations in any other pattern capable of causing disruption in the communication pathway of sympathetic nerve fibers (e.g., spiral patterns, zig-zag patterns, multiple linear patterns, etc.). The pattern can be continuous or non-continuous (e.g., intermittent). The ablation may be targeted at certain portions of the circumference of the vessels (e.g., half or portions less than half of the circumference).

A shape memory wire can be arranged in the annular ring 4, and a distal end of the shape memory wire can extend to the distal end of the annular ring 4. The proximal end of the shape memory wire can be fixed to the distal end of the flexible end 3. The shape memory wire in the annular ring 4 can preferably be made of various shape memory alloys such as nickel-titanium alloy, stainless steel or titanium, with a diameter in the range of 0.25-0.5 mm.

The diameter of the annular ring 4 is in the range of 12-40 mm. For example, the shape memory wire can be configured to bias the annular ring 4 to a desired diameter, such as in the range of 12-40 mm. Additionally, in some embodiments, the pull wire can be used to change or adjust the diameter of the annular ring 4 through a range of diameters including 12-40 mm or other ranges.

The length of the flexible end 3 can be in the range of 30-80 mm and can be made of medical polymer materials such as fluorine, polyesters, polyurethane, polyamide and polyimide. A counterbore can be arranged on the distal end of the flexible end 3, the proximal end of the annular ring can be fixed in the counterbore, wherein the proximal end of the annular ring is a ground thin end.

A pull wire can be embedded in the catheter body, and one end of the pull wire can be fixed to the control handle. The curvature of the flexible end 3 can be controlled by operating the control handle. For example, one end of the pull wire can be fixed to a control button on the handle and the curvature of the flexible end 3 can be controlled by operating the button. This allows the operator to control the handle with one hand and adjust the curvature of the flexible end 3 easily, so that the electrodes 5 on the annular ring 4 can be pressed into contract with the pulmonary artery and achieve acceptable ablation of pulmonary artery intima.

Furthermore, a counterbore can be made on the distal end of the flexible end 3, and its depth can be set according to actual needs, preferably with a depth in the range of 2-8 mm. The proximal end of the annular ring 4 can be a ground thin end, and an outer diameter of the ground thin end fits an inner diameter of the counterbore. The ground-thin end can be inserted into the flexible end 3 and can be fixed to the distal end of the flexible end 3 by bonding, welding or other suitable means, preferably by UV-curing adhesive. Excess glue may be used to seal the distal end of the flexible end 3 and the proximal end of the annular ring 4.

FIG. 1 shows a schematic structural diagram of the multi-pole synchronous pulmonary artery radiofrequency ablation catheter. The annular ring 4 can be arranged at the distal end of the flexible end 3. The annular ring 4 can be an annular structure, and the radius of the annular ring 4 can be effected with shape memory wire.

The annular ring 4 can be provided with a plurality of electrodes 5. Each electrode 5 can be configured to extract or detect neural electrical signals, sense the temperature and conduct ablation. The number of electrodes 5 can vary from the range of 3 to 30, preferably 5 to 20. The electrodes 5 are made of platinum-iridium alloy, gold, stainless steel or nickel alloy. The electrode diameter can be generally 1.3-2.0 mm, and the length of the electrode 5 can be generally in the range of 1.2-4 mm, more suitably 2-3.5 mm. Edge space between the adjacent electrodes suitably can be in the range of 0.5-10 mm, more suitably 1-5 mm.

The pull wire 8 can preferably be made of stainless steel or nickel-titanium. As shown in FIG. 2 and FIG. 3, the distal end of the pull wire 8 extends through a hollow cavity 9 to the proximal end of the annular ring 4, and can be fixed to the distal end of the flexible end 3. The method used for fixing the pull wire 8 to the distal end of the flexible end 3 can be any known method in the prior art.

Optionally, a groove can be arranged on the distal end of the flexible end 3, and a connector 11 can be arranged in the groove. One end of the connector 11 can be connected to the pull wire 8 and the other end of the connector 11 can be connected to the shape memory wire 12. The connector 3 can be fixed to the distal end of the flexible end 3 by injecting glue such as UV-curing adhesive into the groove.

A segment of pull wire 8 extends in the flexible end 3 and a segment of pull wire 8 extends in the catheter body 1. The pull wire can preferably be jacketed with a coil spring 13, and the coil spring 13 can be jacketed with a spring sleeve 14. The spring sleeve 14 may be made of any suitable material, preferably a polyimide material.

The proximal end of the pull wire 8 can be fixed on or in the control handle 2, which can be provided with an adjustment apparatus, and the adjustment apparatus can be configured to adjust the curvature or the diameter of the annular ring 4.

Lead wire 6, as shown in FIG. 2 and FIG. 3, extends through the lead wire cavity 10 to the lead wire cavity of the annular ring 4. The distal end of the lead wire 6 can be connected to electrode 5. The distal end of the lead wire 6 can be fixed to electrode 5 by welding. In some embodiments, the catheter includes one lead wire 6 for each of the electrodes 5.

The distal end of the temperature sensing wire 7 can be embedded under the electrode 5 and the distal end of the temperature sensing wire 7 can be fixed on electrode 5 by bonding, welding or other suitable means. The temperature sensing wire 7 can extend into the catheter body 1 in the lead wire cavity 10 of the flexible end 3 and then extend out from the control handle 2 and can be connected to a temperature control device. In some embodiments, the catheter includes one temperature sensing wire 7 for each of the electrodes 5.

When using the catheter, the pull wire 8 can be operated through the control handle 2 in order to deflect the flexible end 3, thereby providing enhanced control for the user when positioning the annular ring 4 in a desired location, such as an orifice of the pulmonary artery. At this time, the electrodes 5 can be energized for performing ablation on pulmonary artery intima.

The multi-electrode design according to some embodiments can improve the efficacy and safety of ablation, and achieve signal analysis and preferably simultaneous ablation by a plurality of electrodes. This can also improve target accuracy, achieve timely judgment of ablation effect and save operation time. For example, with the annular ring 4 in a desired location, the electrodes can be individually activated to perform ablation at selected sites. This can be a benefit because in some methods of treatment described below, ablation can be performed at selected sites, less than the entire circumferential surface of certain anatomy.

EXAMPLE 2

A multi-pole synchronous pulmonary artery radiofrequency ablation catheter comprises a control handle 2, a catheter body 1, and an annular ring 4. The control handle 2 can be provided with an adjustment apparatus, the catheter body 1 can be hollow, and a cavity can be arranged in the catheter body 1. One or more lead wires 6, temperature sensing wires 7, and a pull wire 8 can be arranged in cavity.

One end of catheter body can be flexible, and the flexible end 3 can be connected to the annular ring 4. The other end of the catheter body can be connected to the control handle 2. One end of the pull wire 8 can be connected to the flexible end 3, and the other end of the pull wire 8 can be connected to the adjustment apparatus of the control handle, and the adjustment apparatus adjusts the tension of the pull wire 3 to control the curvature of the flexible end. This allows the operator to control the handle with one hand and adjust the curvature of the flexible end 3 easily. Thereby the electrodes 5 of the annular ring 4 can be pressed against to better contact an inner surface of a desired anatomy, such as a pulmonary artery, so as to enhance ablation of pulmonary artery intima.

A shape memory wire 12 can be arranged in the annular ring 4. One end of the shape memory wire 12 can extend to the end of the annular ring 4, and the other end of the shape memory wire 12 goes through the root of the annular ring 4 and can be fixed on the flexible end 3 of the catheter body.

The annular ring 4 can also be provided with an electrode group. Each electrode 5 can be connected to a lead wire 6 and a temperature sensing wire 7 and can be configured to extract or detect the nerve electrical signals, sense the temperature and conduct ablation. The lead wires 6 and temperature sensing wires 7 can extend through the catheter body 1 and can be electrically connected to the control handle 2. The control handle 2 can be connected to an external temperature control device.

The annular ring electrodes 5 can be made of a material selected from a group consisting of platinum-iridium alloy, gold, stainless steel and nickel alloy material, with the number in the range of 3-30, a diameter in the range of 1.3-2.0 mm, a length in the range of 1.2-4 mm and an edge space between adjacent electrodes in the range of 0.5-10 mm.

The flexible end 3 of the catheter body can have a counterbore 32. An outer diameter of the root of the annular ring 4 can fit an inner diameter of the counterbore 32. The root of the annular ring 4 can be inserted into the counterbore 32 and fixed.

The flexible end 3 of the catheter body can be provided with a groove. A connector 11 can be arranged in the groove. One end of the connector can be connected to the pull wire 8 and the other end of the connector can be connected to the shape memory wire 12.

The shape memory wire 12 can be made of shape memory alloy such as nickel-titanium alloy, stainless steel or titanium, with a diameter in the range of 0.25-0.5 mm. The diameter of the annular ring 4 can be in the range of 12-40 mm. Preferably, 10 electrodes are arranged on the annular ring, and the width of naked (exposed) side of electrodes can be 0.75 mm, and the space there between can be 5 mm.

The flexible end 3 of the catheter body can be made of medical polymer materials such as fluorine, polyesters, polyurethane, polyamide and polyimide, with a length in the range of 30 mm to 80 mm.

The connection can be via UV-curing adhesive. The joint between the flexible end of the catheter body and the annular ring can be sealed. The pull wire 8 can be made of stainless steel or nickel-titanium alloy. The pull wire 8 can be jacketed with a coil spring 13, and the coil spring 13 can be jacketed with a spring sleeve 14 made of polyimide material.

EXAMPLE 3

Example 3 is similar to Example 1 and Example 2, and the differences can include an infusion tube 22 arranged in the catheter body, a group of evenly distributed through holes 15 (FIG. 4) arranged on one or more of the electrodes 5, with a bore diameter of 1 One end of the infusion tube 22 can be connected to the electrodes 5 through the annular ring 4 such that fluid diffuses out from the through holes 15 on each of the electrodes 5. For example, the annular ring 4 can include or define at least one lumen 24 extending between a proximal end of the annular ring 4 and to the through holes 15 so as to form a closed fluidic connection. In such embodiments, a distal end of the infusion tube 22 can be connected to the proximal end of the lumen 24 in the annular ring 4. The other end of the infusion tube 22 can be connected to a transfusion system, such as a constant-flux pump or other known pumps.

When electrodes 5 generate current, the liquid automatically diffuses from the through holes 15. The transfused liquid can be saline. The cold saline (4° C.) perfusion can help decrease local temperature. When the electrode generates current, the saline can automatically diffuse from the through holes 15, and thus can allow the local temperature to be controlled to a desired temperature, such as to below 60° C. and thereby protect the vascular intima.

Figure 5:
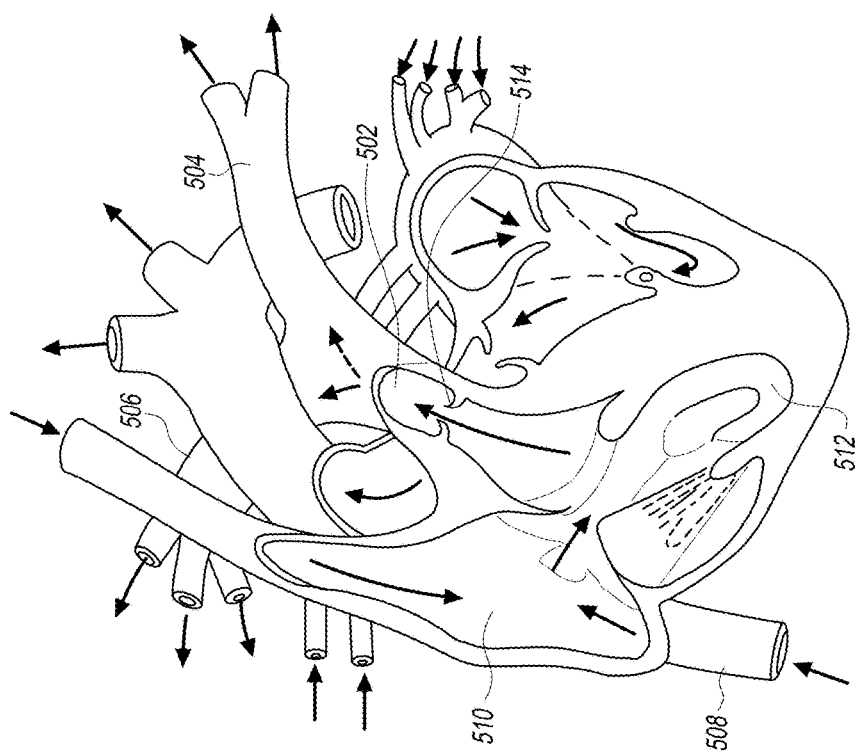
FIG. 5 is a front elevational and partial sectional view of a human heart.

FIG. 5 is a schematic diagram of a human heart and surrounding vasculature, which can be an environment in which the catheter of FIGS. 1-4 can be used to perform ablation treatments such as, for example, but without limitation, denervation of the pulmonary artery. In some methods of treatment, access to the inner walls of the main pulmonary artery 502 as well as the left pulmonary artery 504 and right pulmonary artery 506 can be achieved by passing a catheter, using well known techniques, into a femoral vein, upwardly into the inferior vena cava 508 (lower left hand corner of FIG. 5). The catheter can then be pushed upwards into the right atrium 510, down into the right ventricle 512, then up through the pulmonary semilunar valve 514 into the trunk of the main pulmonary artery 502. As used herein, the term main pulmonary artery (MPA) 502 includes the proximal end of the main pulmonary artery which is the furthest upstream end of the main pulmonary artery 502, at the pulmonary semilunar valve 514, up to the bifurcation of the main pulmonary artery. The distal portion of the MPA 502 includes the portions of the MPA 502 near the bifurcation of the MPA 502 into the left and right pulmonary arteries (LPA 504, RPA 506).

Similarly, the proximal ends of the RPA 506 and LPA 504 are those ends of the LPA 504 and RPA 506 which are adjacent and connected to the distal end of the MPA 502. The distal direction along the LPA 504 and RPA 506 would be the downstream direction of blood flow through the LPA 504 and RPA 506 toward the left and right lungs, respectively.

Thus, using well known techniques, a catheter can be used to provide access to the proximal and distal portions of the MPA 502 as well as the proximal and distal portions of the LPA 504 and RPA 506.

Figure 6:
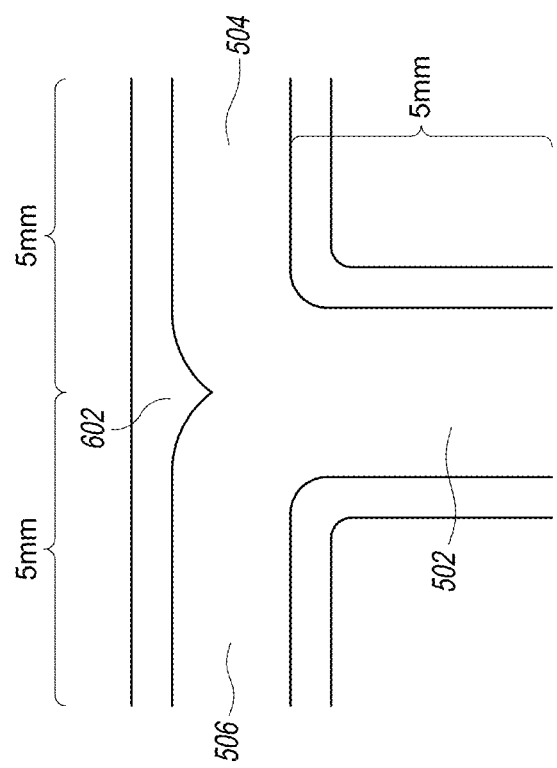
FIG. 6 is a schematic sectional diagram of a pulmonary artery trunk including a distal portion of a main pulmonary artery and the proximal portions of the left and right pulmonary arteries.

FIG. 6 is a schematic diagram of the "trunk" of the pulmonary artery. As used herein, the "trunk" of the MPA 502 is intended to include at least the distal portion of the MPA 502 and the proximal portions of the LPA 504 and RPA 506. FIG. 6 also includes a schematic representation of a carina 602 at the branch of the LPA 504 and RPA 506 from the MPA 502.

As described below, an aspect of at least some of the inventions disclosed herein includes the realization that the trunk of the pulmonary artery of certain animals, including canine and humans, can include concentrated bundles of sympathetic nerves extending from the MPA 502 into the LPA 504 and RPA 506. For example, it has been discovered that there are higher concentrations of sympathetic nerves on the anterior sides of the MPA 502 and in particular, in the vicinity of the distal portion of the MPA 502. Additionally, it has been discovered that the sympathetic nerves bifurcate from this area of higher concentration into the anterior side of the proximal portions of the LPA 504 and RPA 506. In the area of these proximal portions, it has also been discovered that higher concentrations of the sympathetic nerves extend upwardly and toward the posterior side of the LPA 504 and RPA 506.

Thus, in accordance with some of the inventions disclosed herein, ablation is performed in the distal portion of the MPA 502 and the proximal portions of the LPA 504 and RPA 506. In some embodiments ablation is preferentially performed on the anterior side of the inner walls of these structures. In some embodiments, ablation is performed preferentially on the anterior side of the proximal portion of the MPA 502 and on the anterior side and an upper portion of the proximal portions of the LPA 504 and RPA 506, such as at approximately the upper conjunctive site of the distal portion of the MPA 502 at the LPA 504 and RPA 506. As such, high success rates of sympathetic nerve denervation can be achieved as well as high success rates of reduction or elimination of the symptoms of pulmonary hypertension.

It is widely accepted that all vascular walls are regulated by sympathetical and parasympathetical nervous systems. Particularly, pulmonary vessels are known to be innervated by sensory nerve fibers. Previous studies have demonstrated that sympathetic noradrenergic innervation density along the pulmonary artery is highest at its proximal segments and then decreases toward the periphery, a typical finding that is different than arteries in other organs where highest innervation density is found at the level of the smallest arterioles. However, the conclusions of the above-noted study were based on procedures in which the identification of innervation in the pulmonary artery was mainly based on the stimulation of sympathetical nerves or equivalent methods, without direct evidence or other location of sympathetical nerve fibers. However, it has been discovered that some of the conclusions of the above-noted study are incorrect, through the use of techniques for identifying the presence and location of sympathetical nerves in the pulmonary artery using direct labeling techniques.

In particular, experimental procedures were approved by the Institutional Animal Care and Use Committees of the Nanjing Medical University and were performed in accordance with the National Guide for the Care and Use of Laboratory Animals. Mongolia dogs (n=6, weight 7.8±1.2 kg) were obtained from the Nanjing Experimental Center (Nanjing, China). All animals were housed in a single room at 24° C. on a 12 h-light/12 h-dark cycle with fresh food and water.

In this study, a dog was anesthetized with sodium pentobarbital (60 mg per kg, intraperitoneal injection). The chest was excised and opened carefully. The whole pulmonary artery was removed from the chest, with particular attention to avoid the injury of adventitia. In one dog, the pulmonary artery was longitudinally cut along the blood flow direction from the orifice of the main pulmonary artery (the proximal portion of the main pulmonary artery) toward the right and left branches. Then, a vernier focusing camera was used to take pictures in order to identify whether there is a visible difference in the surface of the pulmonary artery between different segments.

With regard to five other dogs, connective tissue was manually dissected away from the pulmonary artery using fine microdissection scissors, under the guidance of stereomicroscope. During this procedure, great care was taken to avoid stripping off the adventitia and possible damage to the perivascular nerves. Vessels were stored at −70° C. for further staining.

Frozen vessels were processed in paraffin wax and fixed in 4% paraformaldehyde for 30 minutes and then incubated at 0.5% Pontamine Sky Blue (Sigma-Aldrich, St. Louis, Mo.) in phosphate-buffered saline (PBS) for 30 minutes to reduce background fluorescence. This was followed by 1 hour at room temperature in a blocking solution of 4% normal goat serum/0.3% Triton X-100 in PBS, then overnight at 4° C. in blocking solution containing an affinity-purified polyclonal antibody against tyrosine hydroxylase (Temecula, Calif.). Vessel segments were then washed in PBS and incubated for 1 hour with secondary antibody (Invitrogen, Carlsbad, Calif.), washed again and positioned on a glass slide. Preparations remained immersed in PBS during image acquisition to maintain hydration and preserve vessel morphology.

Based on previous studies, the sympathetical nerves were thought to be mainly localized at the proximal segment of the pulmonary artery. Thus the distal segment (5 mm in length) of the main pulmonary artery and proximal 5 mm segments of the right and left branches were selected for investigation in the present study. FIG. 6 schematically illustrates, not to scale, a 5 mm segment of the distal portion of the MPA and 5 mm long proximal portions of the LPA and RPA.

Figure 8:
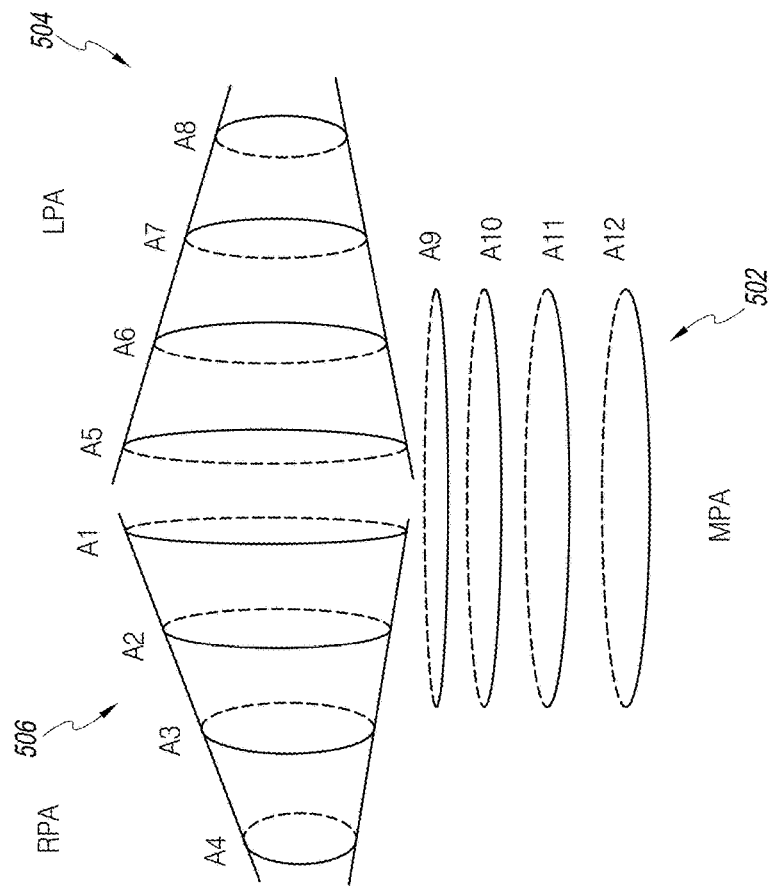
FIG. 8 is a schematic diagram of segmentations of dissected pulmonary arteries including the distal portion of the main pulmonary artery and the proximal portions of the left and right pulmonary arteries.
Figure 14A:
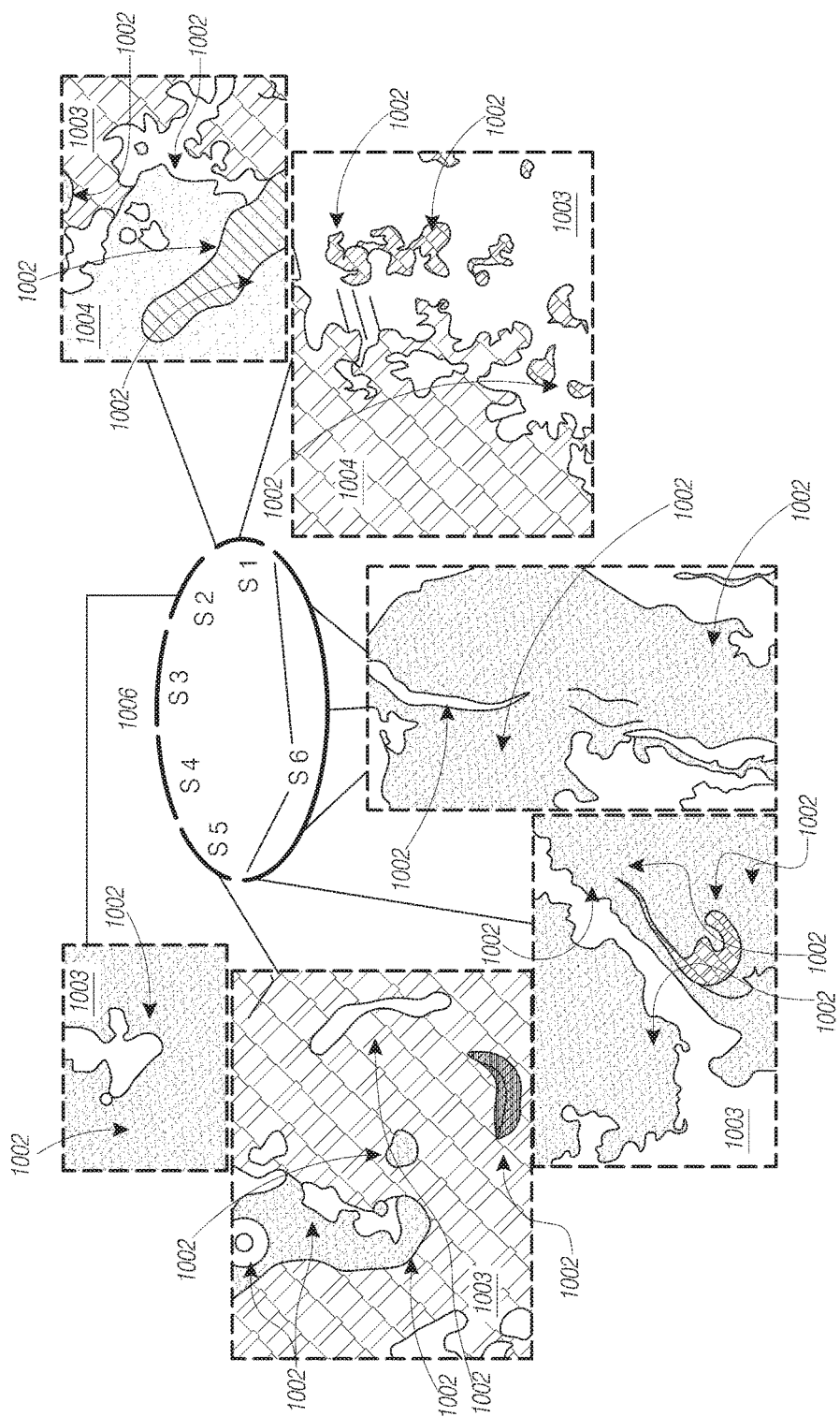
FIG. 14A is a diagram identifying the location corresponding to microscopy of six different locations on level A9 of the main pulmonary artery of FIG. 8.

Multiple transverse slices (2 μm of thickness) of the vessels were cut at 1.6 mm intervals and are identified in the description set forth below in accordance with the labels of FIG. 8 (A1, A2, A3, A4, A5, A6, A7, A8, A9, A10, A11, A12). FIG. 14A is a diagram identifying the location corresponding to microscopy of six different locations on level A9 of the main pulmonary artery of FIG. 8 showing a posterior section 1006, adventitia 1003, and media 1004. Care was taken to keep the luminal morphology of slices consistent with the vessel contour, in order to precisely position the location of nerves. The slices were examined by a pathologist.

Images of each slice were recorded (magnification 40× to 200×) using stereomicroscope (Olympus), and the numbers of total sympathetical nerves bundles (SPNDs) per level were manually calculated. Then all images were input to Image Analysis Software (Image-proplus 5.0), to calculate the minor radius (μm), major radius (μm) and total surface area (TSA, $\mu m^2 \times 10^3$) area of axons.

Figure 7B:
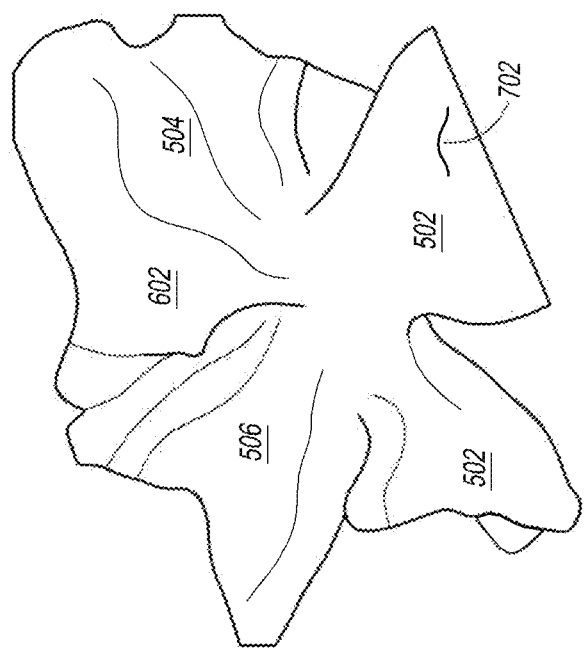
FIGS. 7A and 7B are diagrams of the inner surfaces of two canine pulmonary arteries that have been dissected and laid flat.
Figure 7A:
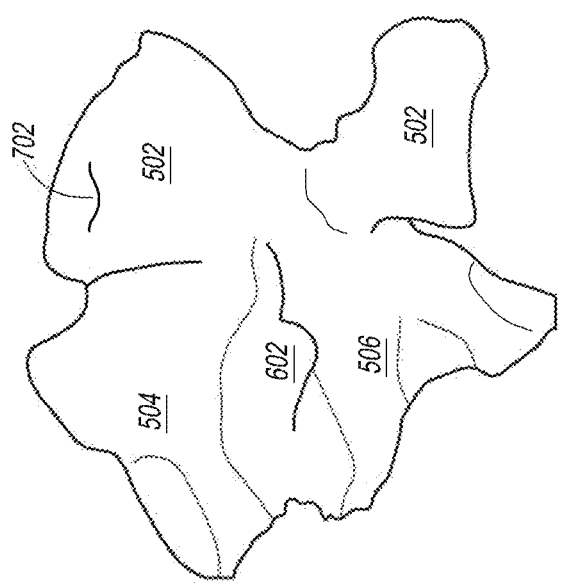

After the pulmonary artery was removed from the chest of the dog, the pulmonary artery was repeatedly cleaned with saline to clean away all blood on the surface of the vessel. Then the whole vessel was cut along the direction from the proximal portion of the main pulmonary artery up through the trunk and into the right and left branches. The above-noted diagrams (FIGS. 7A, 7B) showed that in the anterior wall of the main pulmonary artery, there was an obvious ridgy cystica 702 close to the orifice of the left pulmonary artery. The site of the ridgy cystica 702 felt rigid to the touch, compared to other areas of the pulmonary artery.

Figure 9C:
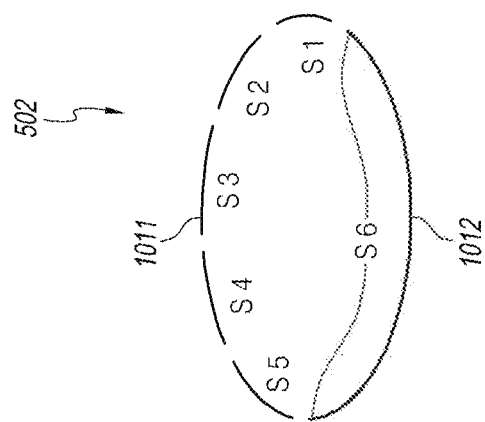
FIGS. 9A-C are diagrams of three of the segmentations identified in FIG. 8.
Figure 9B:
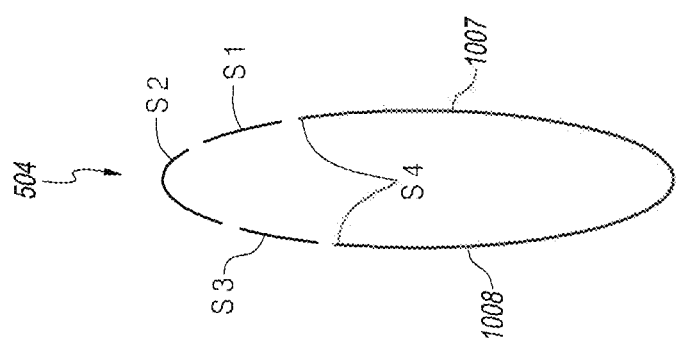
Figure 9A:
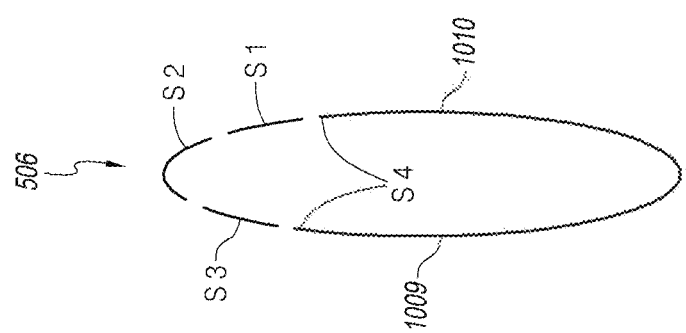

In the vicinity of the bifurcation portion of the pulmonary artery, segments 5 mm in length of the distal main pulmonary artery and the proximal portions of the right and left pulmonary arteries were studied. Four transverse slices (thickness 2 μm, 1.6 mm intervals) from each segment were prepared for analysis. Each slice ("level") was divided into 4 subsegments in the right and left pulmonary arteries (S1, S2, S3, S4 in FIGS. 9A-C) and 6 subsegments in the main pulmonary artery along the counterclockwise direction (S1, S2, S3, S4, S5, S6 in FIGS. 9A-C). FIG. 9A further shows an anterior wall 1009 and a posterior wall 1010. FIG. 9B further shows a posterior wall 1008 and an anterior wall 1007. FIG. 9C further shows a posterior wall 1011 and a anterior wall 1012. FIGS. 10A-D are enlargements of microscopy slides corresponding to the portions identified as S1-S4, respectively, of level A1 of the right pulmonary artery of FIGS. 9A-C. FIGS. 10A-D show adventitia 1003, media 1004, and a lumen 1005.

Figure 10A:
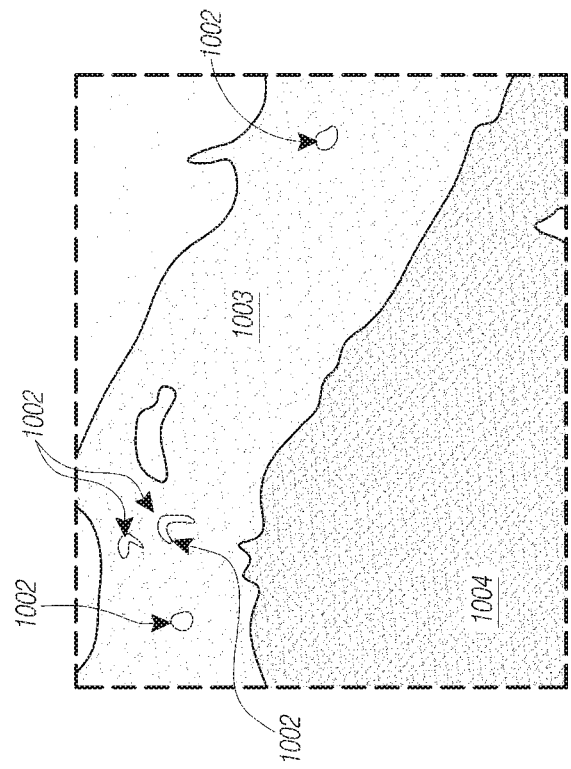
FIGS. 10A-10D are enlargements of microscopy slides corresponding to the portions identified as S1-S4 of level A1 of the right pulmonary artery of FIG. 9A.
Figure 10B:
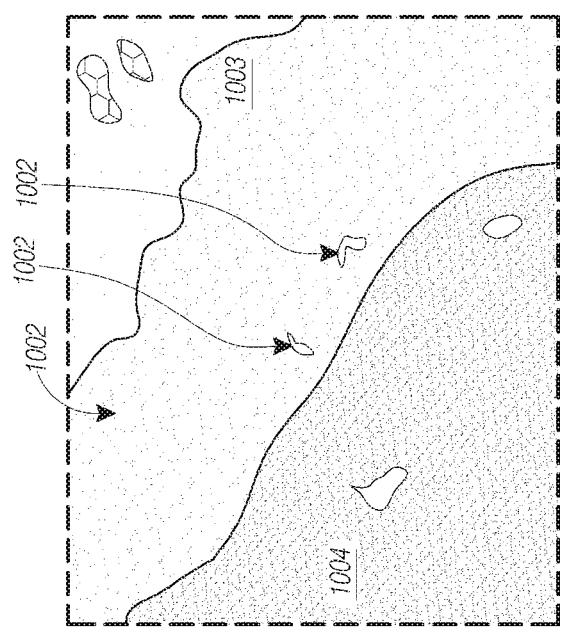
Figure 10D:
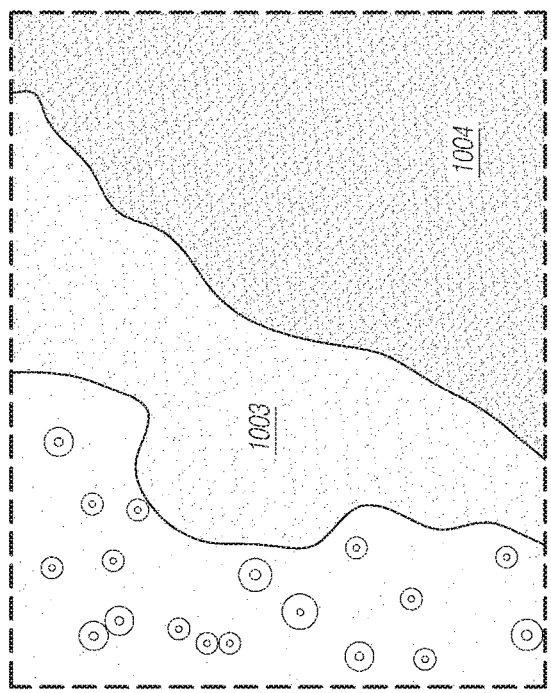
Figure 10C:
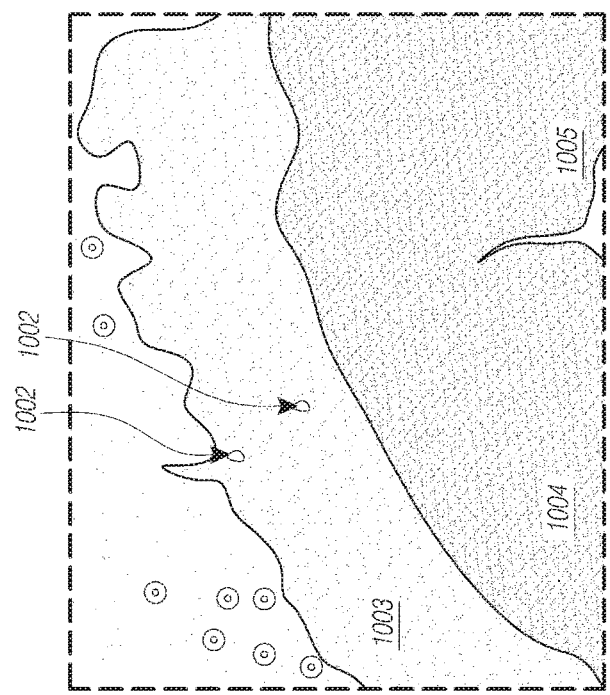
Figure 11:
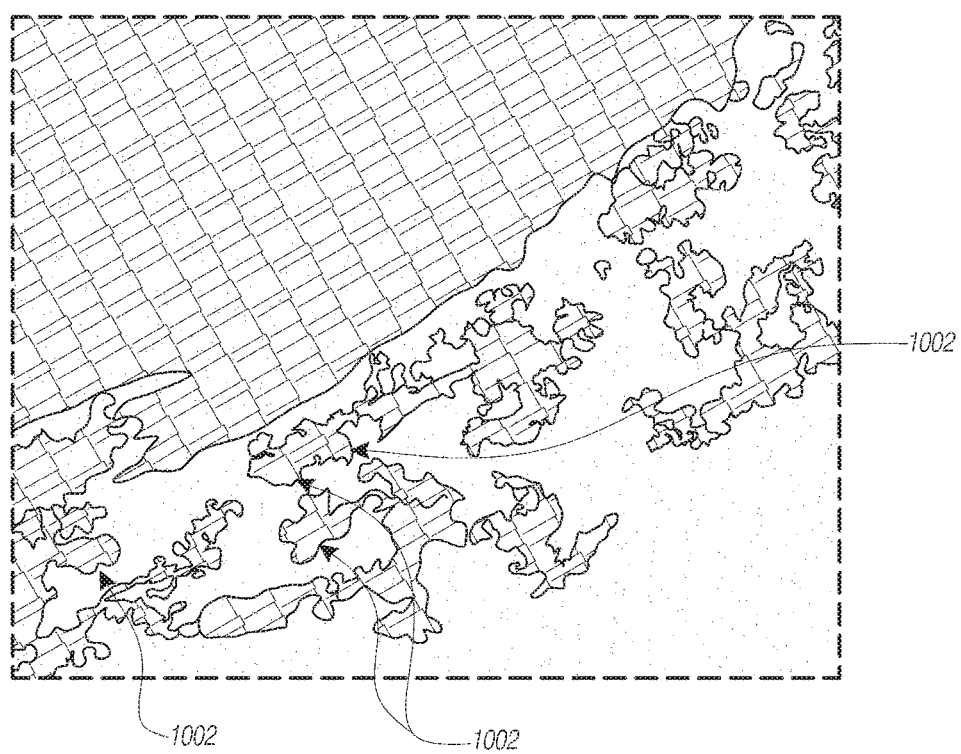
FIG. 11 is a photograph of microscopy of the portion identified as S6 of level A9 of the main pulmonary artery of FIG. 9C.

Upon inspection of these samples, it was observed that more SPNDs 1002 were identified in the posterior wall in both the left and right pulmonary arteries (FIG. 10A). However the number of SPNDs 1002 was 1.6±0.2 in the S1 subsegment of the A5 level in the left pulmonary artery branch, significantly different from 1.2±0.2 in the S1 subsegment of level A1 in the right pulmonary artery (p=0.033). In contrast, more SPNDs 1002 were labeled in the anterior wall (S6) of the main pulmonary artery (FIG. 11) and decreased gradually from the levels A9 to A12.

The minor and major radii of sympathetical axons in the main pulmonary artery were 85±2 μm and 175±14 μm, compared to 65±3 μm and 105±12 μm in the left pulmonary artery or 51±2 μm and 86±8 μm in the right pulmonary artery, respectively, resulting in significant differences in surface area of axons between the main pulmonary artery and the LPA and RPA (FIGS. 9A-C).

Figure 13:
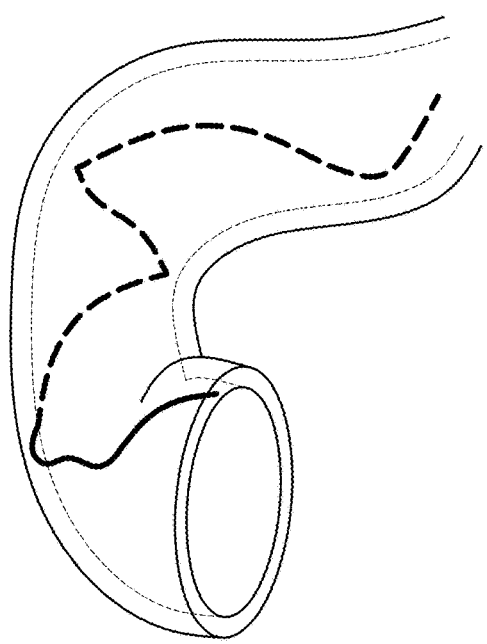
FIG. 13 is an anterior view of the left pulmonary artery of FIG. 12.
Figure 12:
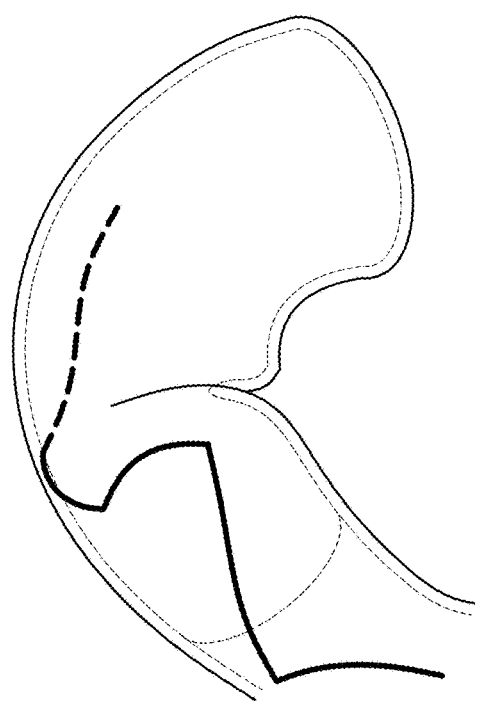
FIG. 12 is a posterior and perspective view of a model of the left pulmonary artery of FIGS. 7A and 7B.

Based on the results of the above-described observations, it has been determined that in canines, sympathetical nerves are distributed in higher concentrations along the anterior wall of the main pulmonary artery, then extend into the left and right pulmonary arteries, then extend upwardly and then toward the posterior walls of the left and right pulmonary arteries, as schematically represented in FIG. 12 and FIG. 13.

Further, inspection of subsegment S6 in level A9 (FIG. 11) of the MPA (magnification 200×) revealed that a bundle or main bundle of sympathetical nerves originate from approximately the middle of the anterior wall of the distal portion of the main pulmonary artery and that this main bundle is bifurcated to the left and right pulmonary arteries.

This discovery provides a basis for more effective denervation of the pulmonary artery. For example, by selectively ablating only portions of the main pulmonary artery and the left and right pulmonary arteries, a higher success rate of denervation can be achieved with less unnecessary tissue damage. Such denervation can provide significant benefits in the treatment of diseases such as pulmonary hypertension, as described below.

With regard to the disease of pulmonary hypertension, it is well known that the lung receives axons from principal sympathetic neurons residing in the middle and inferior cervical and the first five thoracic ganglia (including the stellate ganglion), and the vasculature is the major sympathetic target in the lung. Sympathetic nerve stimulation increases pulmonary vascular resistance and decreases compliance, which is mediated by noradrenaline via a-adrenoreceptors, primarily of the al-subtype.

Previous studies have confirmed the multiplicity of transmitters released from one nerve ending which might explain why pharmacological blockade of the "classical" transmitter alone does not effectively abolish the effects elicited by nerve stimulation. The present study explained above supports the concept that more successful sympathetical denervation along the pulmonary trunk can be enhanced at the proximal segments of the left and right pulmonary arteries rather than at the distal basal trunks. Further, the percutaneous pulmonary denervation (PADN) procedure has potential for decreasing pulmonary pressure and resistance induced by unilateral balloon occlusion in the interlobar artery. However, until now, there was a lack of data showing the distribution of sympathetical nerves in the pulmonary trunk. Thus, the accurate identification of the position of sympathetical nerves is important for performing a successful PADN procedure. In the present study, significantly larger bundles of sympathetical nerves were identified in the mid-anterior wall of the distal portion of the main pulmonary artery, which is bifurcated into the posterior wall of the left and right pulmonary arteries. These results imply that one or more ablation procedures, for example, by the PADN procedure, especially around the distal portion of the main pulmonary bifurcation and the proximal portions of the LPA and RPA are more likely to provide enhanced results and more successful denervation, as was suggested in the animal study noted above.

It is noted that sympathetic noradrenergic innervation density is highest at the large extra-pulmonary and hilar blood vessels, both arteries and veins, and then decreases toward the periphery. This is in marked contrast to many other organs, in which the highest innervation density is found at the level of the smallest arterioles. Such distribution varies from species to species with regard to the extent to which the sympathetic noradrenergic axons reach into the lung. In guinea pigs, rabbits, sheep, cats, dogs, and humans, small arteries down to 50 µm in diameter are innervated, whereas in rats, mice, hedgehogs, and badgers, noradrenergic innervation stops close to the lung.

An extensive network of noradrenergic and NPY-containing fibers has been noted around pulmonary arteries of several species, but only a few studies used double-labeling techniques to evaluate the extent of colocalization. In the guinea pig, principally all noradrenergic fibers innervating pulmonary arteries and veins contain NPY and, in addition, dynorphin, a neuropeptide of the opioid family. In this aspect, pulmonary vascular innervation differs markedly from that of skin arteries in the same species, wherein three different combinations of noradrenaline, NPY, and dynorphin are used by sympathetic axons. Each of these populations is restricted to a specific segment of the arterial tree in the skin. Still, noradrenergic and NPY-containing fibers do not match 1:1 in the lung either, as there is a minor population of axons innervating guinea pig pulmonary arteries and veins that contains NPY plus vasoactive intestinal peptide (VIP) but not noradrenaline. It remains to be clarified whether this less-frequent fiber population represents the non-noradrenergic neurons projecting to the guinea pig lung or originates from other systems.

The present study explained above, which relied on the serial slicing at various levels through the pulmonary artery trunk, demonstrates that larger bundles of nerves are more localized in the anterior wall of the main pulmonary artery and then bifurcate into the left and right pulmonary arteries along the posterior walls of the LPA and RPA. The above study was performed on canine anatomy.

One of the diseases that can be treated with the present methods and devices is idiopathic pulmonary arterial hypertension (IPAH). IPAH is characterized by elevations of mean pulmonary artery pressure (PAP) and pulmonary vascular resistance (PVR). The pathogenesis of IPAH was believed to be due to imbalance between locally produced vasodilators and vasoconstrictors. Recent studies have demonstrated that vascular wall remodeling also contributed to elevated PVR. The role of neural reflex in the mediation and development of IPAH has not been specifically investigated. The present animal study described above demonstrates that the PADN procedure can reduce or completely abolish elevations of PAP induced by balloon occlusion at interlobar segments, but not at the basal trunk.

In a further phase of the present study, a human study was conducted. Prior to enrollment, all 21 patients received a diuretic (hydrochlorothiazide at a dose of 12.5 mg to 25 mg, once daily, and/or spironolactone at a dose of 20 mg to 40 mg, once daily) and beraprost (120 mg, 4 times daily) (Table 1), with either sildenafil (20 mg, 3 times a day) or bosentan (120 mg, twice daily) or digoxin (0.125 mg, once daily). Functional capacity of the patients was determined by a 6-minute walk test (6MWT), followed by an assessment of dyspnea using the Borg scale. The 6MWT was performed at 1 week, 1 month, 2 months, and 3 months following the PADN procedure. The WHO classification at rest and during exercise was recorded by a physician who was blinded to the study design.

Echocardiography was performed at 1 week, 1 month, 2 months, and 3 months following the procedure. Echocardiographic studies were done using a Vivid 7 ultrasound system with a standard imaging transducer (General Electric Co., Easton Turnpike, Conn., US). All of the echocardiograms were performed and interpreted in the Medical University Echocardiographic Laboratory. All of the measurements were performed following the recommendations of the American Society of Echocardiography. Digital echocardiographic data that contained a minimum of 3 consecutive beats (or 5 beats in cases of atrial fibrillation) were acquired and stored. RV systolic pressure is equal to systolic PAP in the absence of pulmonary stenosis. Systolic PAP is equal to the sum of right atrial (RA) pressure and the RV to RA pressure gradient during systole. RA pressure was estimated based on the echocardiographic features of the inferior vena cava and assigned a standard value. The RV to RA pressure gradient was calculated as $4v_t^2$ using the modified Bernoulli equation, where $v_t$ is the velocity of the tricuspid regurgitation jet in m/s. The mean PAP was estimated according to the velocity of the pulmonary regurgitation jet in m/s. The tricuspid excursion index (TED is defined as (A–B)/B, where A is the time interval between the end and the onset of tricuspid annular diastolic velocity, and B is the duration of tricuspid annular systolic velocity (or the RV ejection time). PA compliance for patients was calculated as stroke volume divided by pulse pressure (systolic PAP minus diastolic PAP).

Hemodynamic measurements and blood oxygen pressure/saturation determinations from the RA, RV, and PA were done prior to and immediately after the PADN procedure. These measurements were repeated at 24 hours and 3 months.

A 7F flow-directed Swan-Ganz catheter (131HF7, Baxter Healthcare Corp., Irvine, Calif.) was inserted into an internal jugular or subclavian vein. Measurements of resting RA pressure, RV pressure, systolic/diastolic/mean PAP, pulmonary artery occlusive pressure (PAOP), cardiac output (CO) (using thermodilution method), and mixed venous oxygen saturation were recorded. The PVR [=(mean PAP−PAOP)/CO] and trans-pulmonary gradient (TPG=mean PAP−PAOP) were then calculated. All of the measurements were recorded at the end of expiration. Five criteria were used to evaluate if a PAOP measurement was valid: (1) the PAOP was less than the diastolic PAP; (2) the tracing was comparable to the atrial pressure waveform; (3) the fluoroscopic image exhibited a stationary catheter following inflation; (4) free flow was present within the catheter (flush test); and (5) highly oxygenated blood (capillary) was obtained from the distal portion in the occlusion position. If the PAOP measurement was unreliable, the left ventricular end-diastolic pressure was then measured and used rather than the PAOP. The blood samples from the SVC and pulmonary artery were obtained for the measurements of oxygen pressure and saturation. Particularly significant reductions in systolic and mean PAP were achieved using temperatures above 50° C., drawing an electrical load of 8-10 W for a duration of 60-120 s, for example as shown in FIG. 14B.

The PADN procedure was performed with a dedicated 7.5F multiple-function (temperature-sensor and ablation) catheter which comprised two parts, a catheter shaft 3 and handle 2 (FIG. 15A) which is an embodiment of the catheter illustrated in FIGS. 1-4. The catheter of FIG. 15A had a tapered (to 5F) annular ring 4 with 10 pre-mounted electrodes 5 (E1-E10) each separated by 2 mm, however, other spacings can also be used. For purposes of the description set forth below, the electrodes 5 have been numbered, as shown in FIG. 15B, with the distal-most electrode 5 identified as electrode E1 and the proximal-most electrode 5 identified as electrode E10.

As described above with reference to FIGS. 1-4, the annular ring 4 or ("circular tip") can be constructed so as to be biased into an annular/circular shape, such as the circular shape illustrated in FIG. 15B and FIG. 1 to have any desired outer diameter. For example, in various embodiments, the annular ring 4 can be configured to be biased into a circular shape having an outer diameter of 20 mm, 25 mm, 30 mm, 35 mm, 40 mm, 45 mm, or other diameters. Additionally, a kit containing the catheter of FIG. 1 can include a plurality of different annular rings 4 configured to be biased to a plurality of different outer diameters, such as those noted above, or other diameters.

A controller or "connect box" can be connected to the handle 2 of the catheter for providing ablation energy. For example, an ablation controller 100 can be configured to provide ablation energy to each of the electrodes E1-E10. Thus, in some embodiments, the controller 100 includes a selector knob 102 configured to allow a user to select activation of all the electrodes E1-E10, or selective actuation of individual ones of the electrodes E1-E10, one at a time.

Thus, in some embodiments, as illustrated in FIG. 15D, the selector knob 102 includes a position indicator 104 which, by rotating the knob 102 can be aligned with indicia corresponding to the electrodes E1-E10. In the illustrated embodiment, the indicia on the controller 100 includes the numbers 1-10 as well as a position identified as "OFF" and a position identified as "NULL." In some embodiments, the connect cable 106 can include a plurality of wires, for example, ten wires which correspond to the lead wire 6 described above with reference to FIGS. 1-4, each one of which is individually connected to respective electrodes E1-E10.

The controller 100 can include a physical switch for creating an electrical connection between a source of RF energy and a desired one of the electrodes E1-E10. An electrode (not shown) can be directly connected to the knob 102 with additional contacts (not shown) disposed around the electrode at approximately the positions identified as 1 through 10 on the controller 100. Thus, rotation of the knob 102 will connect an internal electrode (not shown) with the contacts aligned with each one of the positions 1-10.

The controller 100 can be configured to provide the desired amount of ablation energy when a circuit is created by the alignment of the position indicator 104 with the corresponding position (1 through 10) on the controller 100 thereby delivering electrical energy to the selected one of the electrodes E1-E10 causing electrical energy to pass through the selected electrode 5 into any conductive material in contact with that selected electrode.

For example, during the PADN procedure, the electrodes E1-E10 can be in contact with an inner wall of the pulmonary artery trunk thereby allowing electrical energy from one of the electrodes E1-E10 to flow through the tissue of the inner wall of the pulmonary artery, described in greater detail below.

In some embodiments, with continued reference to FIG. 15D, the controller 100 can include a plurality of ports. For example, the controller 100 can include a catheter port 120, which can be configured for creating a fluidic connection to the annular ring for purposes of providing a flow of saline to the annular ring 4. The controller 100 can also include an RF port 122 configured to connect to any known radiofrequency generator used with regard to ablation procedures.

Additionally, the controller 100 can include an "ECG" port 124 configured for connection with standard ECG monitoring equipment. Thus, in some embodiments, the connect cable 106 can also include wires or conduits for transmitting data through the RF port 124.

Thus, in some configurations, the RF port 122 can be connected to a source of RF energy (not shown). One or more wires (not shown) can connect the port 122 to a contact on the end of an electrode connected to the selector knob 102. Additionally, the ten wires (not shown) can be configured to deliver RF electrical energy to the electrodes E1-E10 each of which can be connected to contacts (not shown)

associated with the selector positions 1-10 disposed around the periphery of the selector knob 102.

Thus, the electrode connected to the rotating selector knob 102 can be moved into contact with the electrical contacts associated with each of the positions 1-10 thereby creating a circuit connecting the electrical energy entering the controller 100 through the port 122 with the associated lead wire 6 for conducting electrical energy to the desired electrode E1-E10.

Thus, specifically, when the selector knob 102 is turned such that the position indicator 104 is aligned with position 1 on the controller 100, electrical energy from the RF port 122 is conducted through an associated lead wire 6 to the electrode E1. Aligning the indicator 104 with the other positions on the controller 100 would conduct electrical energy to the other electrodes associated with those other positions.

In some embodiments, a method for treating pulmonary hypertension can include a step of identifying the position of the pulmonary trunk of the patient using angiography. For example, baseline pulmonary artery angiography can be performed to identify the position of the pulmonary artery bifurcation from the main pulmonary artery into the left and right pulmonary arteries.

Additionally, the baseline pulmonary artery angiography can be used to determine the diameter of the portions of the pulmonary artery trunk upon which ablation is desired. As such, the appropriate diameter of the annular ring 4 can be determined based on the determined diameters of the pulmonary artery trunk noted above. For example, in some embodiments, an annular ring 4 having a biased diameter slightly larger than the diameters of the targeted anatomy can be used so as to enhance the contact between the electrodes 5 and the inner surface of the targeted anatomy. As such, for example, when the annular ring 4 is moved out of a sheath 1602 and allowed to expand into its biased circumferential configuration which has an outer diameter slightly larger than the inner diameter of the targeted portions of the pulmonary artery trunk, the bias of the annular ring 4 will assist in pressing the electrodes 5 into contact with the targeted tissue.

In some embodiments, with reference to FIGS. 16A-16H, a method can include a step of positioning a catheter in a pulmonary artery trunk. For example, the sheath 1602 can be inserted through the femoral vein and advanced to the main pulmonary artery, as shown in FIG. 16A. A catheter, such as the catheter illustrated in FIG. 1 and FIGS. 15A-15E can be advanced along the sheath 1602 shown in FIG. 16A to the location of the pulmonary artery trunk.

With the distal end of the catheter maintained in place, the sheath 1602 can be withdrawn. It may be necessary to push on the catheter to maintain its position with the portion of the catheter forming the annular ring 4 held within the pulmonary artery trunk.

As the annular ring 4 is released from the sheath 1602, as illustrated in FIG. 16B, the annular ring 4 can adopt the shape and diameter to which it is biased.

By slightly rotating and pushing the handle 2 in a clockwise direction, the annular ring 4 can be positioned at the proximal portion of the left pulmonary artery, such as at the ostium. In some embodiments, this initial position can be within a range of approximately 5 mm from the orifice of the left pulmonary artery or within a range of 2 mm, as illustrated in FIG. 16D.

By observing the orientation of the annular ring 4, the desired one or plurality of the electrodes E1-E10 can be selectively energized so as to perform ablation at the desired location on the interior surface of the left pulmonary artery. For example, in some embodiments, it may be more effective to selectively ablate the posterior wall of the left pulmonary artery, so as to achieve at least some sympathetic denervation of the left pulmonary artery and the proximal portion thereof, such as within 2 mm or 5 mm of the ostium of the left pulmonary artery.

The annular ring 4 can then be rotated, such as in the counterclockwise direction, by rotating and withdrawing the handle 2 in order to reposition the annular ring 4 into the distal portion of the main pulmonary artery such as at the bifurcation area. For example, in some embodiments, as illustrated in FIG. 16E, the annular ring 4 can be positioned within about 5 mm of the bifurcation in the pulmonary artery trunk. Ablation can then be performed using the desired one or plurality of the electrodes E1-E10.

For example, positioned as such, the selected one or plurality of electrodes E1-E10 can be energized to achieve the desired sympathetic denervation of the distal portion of the main pulmonary artery. In some embodiments, it may be desirable to perform ablation preferentially on the anterior wall of the distal portion of the main pulmonary artery.

Additionally, further rotating and pushing the handle 2 can be performed until the annular ring 4 is positioned in the proximal portion of the right pulmonary artery, such as at the ostium. In some embodiments, this position can be within 5 mm of the ostium of the right pulmonary artery. Further, in some embodiments, this position can be within 2 mm of the ostium of the right pulmonary artery.

With the annular ring 4 positioned as such, the desired one or plurality of electrodes E1-E10 can be energized so as to achieve at least some sympathetic denervation in the proximal portion of the right pulmonary artery. For example, in some embodiments, it may be beneficial to focus on the posterior wall of the right pulmonary artery.

In some embodiments, a method for treating pulmonary hypertension can also include a step of confirming the appropriate contact between the electrodes E1-E10 and the endovascular surface corresponding to the three positions noted above. For example, in some embodiments, such confirmation can be performed by determining if there is strong manual resistance when attempting to rotate the handle 2. Additionally, it can be determined if the annular ring 4 cannot be advanced distally, resulting in the deformation of the catheter as illustrated in FIG. 16G or if there is ease in withdrawing proximally, resulting in the deformation of the catheter illustrated in FIG. 16H. Additionally, confirmation can be performed using angiographic confirmation.

After the annular ring 4 is positioned as desired, such as in the positions illustrated in FIG. 16D, FIG. 16E and FIG. 16F, at least one of the electrodes E1-E10 can be energized so as to perform ablation. For example, in some embodiments, a method for treating pulmonary hypertension can include the sequential energization of each of the electrodes E1-E10.

Additionally, in some embodiments, a method for treating pulmonary hypertension or for performing pulmonary denervation can include the step of repositioning the annular ring 4 so as to shift the location of the electrodes E1-E10 and then repeating energization of all of the electrodes E1-E10. As such, a more complete denervation of the entire inner surface of the associated vessel can be achieved.

In some embodiments, any desired energy levels or temperatures can be used for performing ablation using the electrodes E1-E10 noted above. For example, in some embodiments, ablation can be performed at temperatures above 50° C., drawing an electrical load of 8-10 W for a duration of 60-120 s. Additionally, in some embodiments, the method of treatment of pulmonary hypertension or the method of sympathetic denervation of the pulmonary artery can be performed with a patient anesthetized but conscious. Thus, any ablation procedure can be stopped if the patient complained of intolerable chest pain.

In some embodiments, EKG and hemodynamic pressure can be monitored and continuously recorded throughout the method. In a study performed in accordance with the description noted above, success was defined as a reduction in the mean PAP≥10 mmHg (as measured by the Swan-Ganz catheter). During the study, there were no complications. Additionally, the patients were monitored in the Coronary Care Unit (CCU) for at least 24 hours after the PADN procedure was performed.

For example, in some embodiments of methods disclosed herein, a dedicated 7.5 F triple-function catheter (A) can be used, which can include a tapered annular ring 4 with 10 electrodes 5 (each has 0.75 mm electrode-width and is separated by 2 mm, pre-mounted. Electrodes are connected with a connect-cable 106 and a connect-box/controller 100. There are 10 positions of the knob 102 (FIG. 15D) on the surface of controller 100, and each is associated with one of the electrodes E1-E10 on the annular ring 4 of the ablation catheter. Sequential ablation can be performed by turning the knob 102 as desired after the whole system is set up. In certain embodiments, ablation is interrupted while switching ablation from one electrode to another.

In some embodiments of methods for performing pulmonary artery denervation or methods for treating primary PAH ablation of the distal portion of the main pulmonary artery can be performed preferentially on the anterior side thereof. For example, in some embodiments, as shown in FIG. 17A, ablation can be performed at the positions identified as M1, M2, M3, M4, and M5.

Figure 17A:
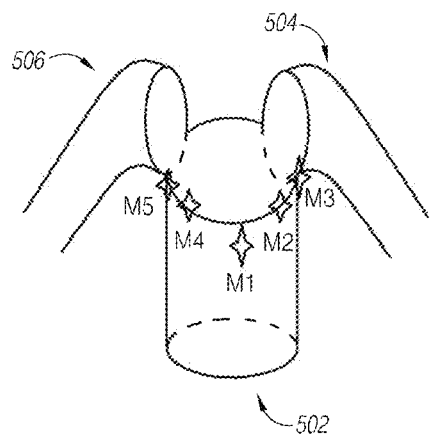
FIG. 17A is a schematic diagram of the trunk of a pulmonary artery and identifies locations for ablation in a distal portion of a main pulmonary artery.

With a continued reference to FIG. 17A, the position identified as M1 is at the "6 o'clock" position in the distal portion of the main pulmonary artery. The positions identified as M3 and M5 are the sites where the anterior wall of the main pulmonary artery connects to the left and right pulmonary arteries, respectively. The positions identified as M2 and M4 correspond to the "5 o'clock" and the "7 o'clock" positions on the anterior side of the distal portion of the main pulmonary artery.

Figure 17B:
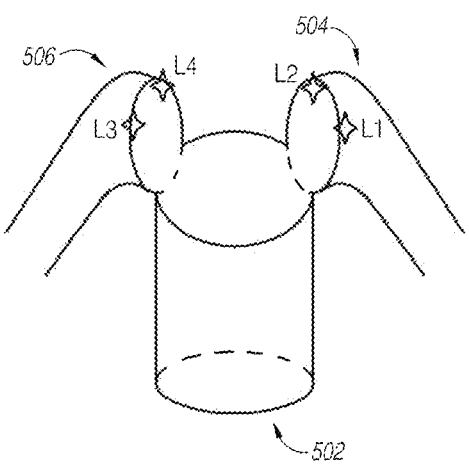
FIG. 17B is a schematic diagram of a pulmonary artery trunk and identifies locations for ablation in proximal portions of the left and right pulmonary arteries.

In some embodiments, with reference to FIG. 17B, sympathetic denervation in the left and right pulmonary arteries can be performed, preferentially, at approximately the middle of the anterior wall of the proximal portion of the left pulmonary artery (L1) and at approximately the upper conjunctive site of the distal portion of the main pulmonary artery in the left pulmonary artery (L2).

Similarly, during a method of performing pulmonary denervation of the right pulmonary artery, ablation can be preferentially performed at a point approximately at the middle anterior wall of the proximal portion of the right pulmonary artery (L3) and at approximately the upper conjunctive site of the distal portion of the main pulmonary artery and the right pulmonary artery (L4).

In some embodiments, sympathetic denervation can be performed, for example, for treatment of pulmonary hypertension associated with a pulmonary duct artery (PDA) 1802. For example, a pulmonary duct artery usually connects the descending aorta with the left pulmonary artery 504, as shown in FIG. 5. With this anatomy, the left pulmonary artery can be significantly larger than the right pulmonary artery.

Figure 18A:
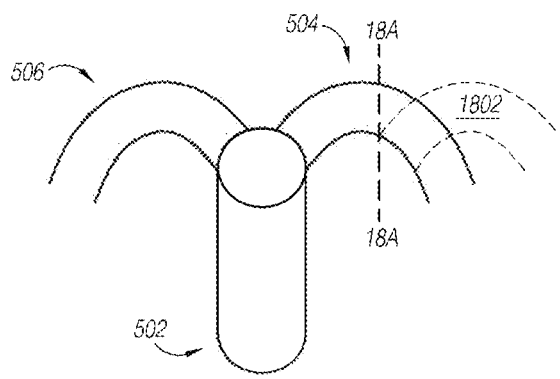
FIG. 18A is a schematic diagram of a pulmonary artery trunk identifying a position for ablation in a portion of the left pulmonary artery proximal to a pulmonary artery duct.

Thus, in some embodiments, ablation can be performed at a position proximal to connection between the left pulmonary artery and the pulmonary duct artery, identified by line 18A-18A in FIG. 18A and referred to as "Level A". Thus, using the technique described above with reference to FIGS. 16A-16H, the annular ring 4 can be positioned at a position corresponding to "Level A" of FIG. 18B. Ablation can then be performed around part or all of the interior wall of the left pulmonary artery at that location.

Figure 18B:
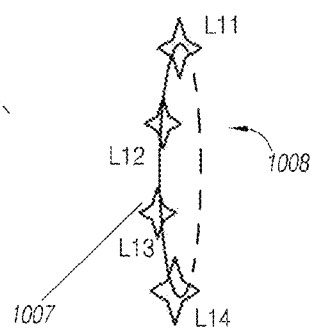
FIG. 18B is a schematic diagram of points of ablation in the anterior wall of the ablation position identified in FIG. 18A.

In some embodiments, ablation can be preferentially performed on the anterior wall of the left pulmonary artery proximal to the proximal end of the pulmonary duct artery. For example, ablation can be performed at four or more sites, such as those identified as sites L11, L12, L13, L14. As illustrated in FIG. 18B, which shows an anterior wall 1007 and a posterior wall 1008, position L11 corresponds to "12 o'clock", position L12 corresponds to "2 o'clock", position L13 corresponds to "3 o'clock", and position L14 corresponds to "6 o'clock." Other positions can also be used.

Additionally, in some embodiments, ablation can also be performed at positions M1-M5 illustrated in FIG. 17A and positions L1-L4 of FIG. 17B.

Figure 19A:
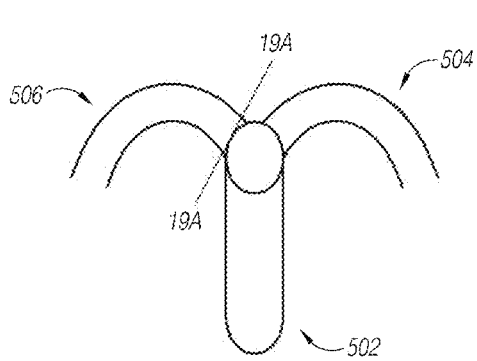
FIG. 19A is a schematic diagram of a pulmonary artery trunk identifying a position for ablation in a proximal portion of the right pulmonary artery for treatment of unilateral chronic thrombotic embolism.

In some embodiments, a method for sympathetic denervation can be used for treating pulmonary hypertension resulting from unilateral chronic thrombotic embolism. For example, a patient suffering from unilateral CTEH can have an occluded right pulmonary artery. For example, in some patients, the RPA can be significantly enlarged as illustrated on the left side of FIG. 19A. Similarly to the method described above with reference to FIG. 18B, ablation can be performed at the position identified by line 19A-19A in FIG. 19A and referred to as "Level B". Ablation can be performed at one or a plurality of locations along the inner surface of the right pulmonary artery at the position of Level B, or other positions. Additionally, ablation can be preferentially performed on a plurality of points along the anterior wall of the right pulmonary artery at the position of Level B.

Figure 19B:
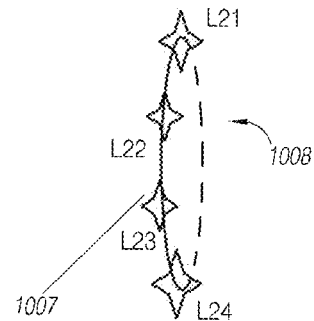
FIG. 19B is an enlarged schematic diagram of the portion identified in FIG. 20A and indicates positions for ablation in the anterior wall of the proximal portion of the right pulmonary artery.

For example, the positions identified in FIG. 19B can be considered such as position L21 corresponding to "12 o'clock", position L22 corresponding to "2 o'clock", position L23 corresponding to "3 o'clock", and position L24 corresponding to "6 o'clock." Additionally, in some embodiments, ablation can also be performed at positions M1-M5 illustrated in FIG. 17A and positions L1 and L2 illustrated in FIG. 17B.

Figure 20:
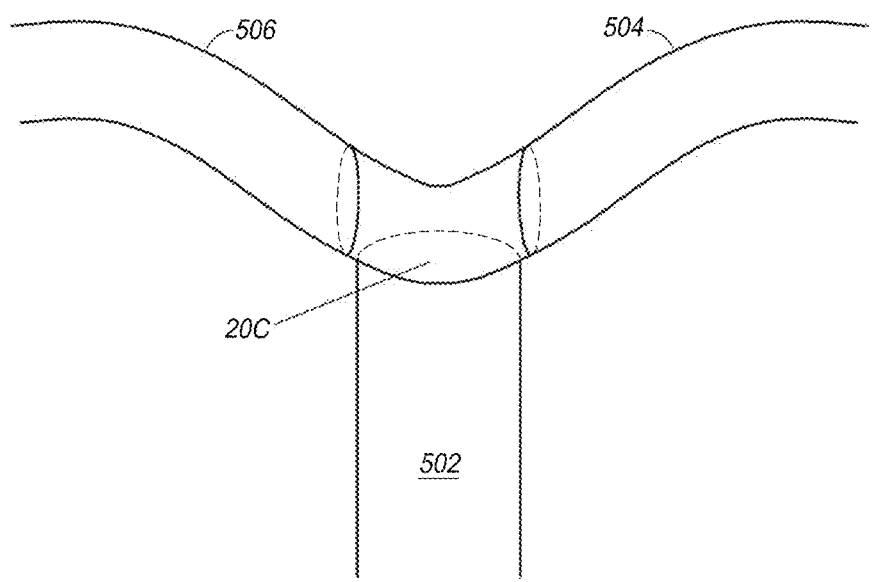
FIG. 20 is a schematic diagram of a pulmonary artery trunk including a distal portion of a main pulmonary artery and the proximal portions of the left and right pulmonary arteries.

With reference to FIG. 20, further embodiments of treatments for pulmonary hypertension can include selected ablation of portions of the pulmonary artery trunk, at fewer ablation sites than some of the embodiments described above. For example, FIG. 20 identifies "Level C", indicated as 20C, for reference with regard to the ablation sites identified in FIG. 21.

Figure 21:
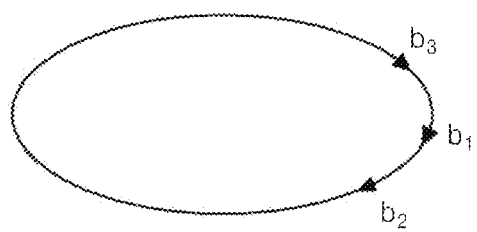
FIG. 21 is a schematic diagram of optional points of ablation along Level C identified in FIG. 20, proximate to a transition between a left lateral wall of the main pulmonary artery and a lower wall of a proximate portion of the left pulmonary artery.

With reference to FIG. 21, an enlarged schematic diagram of "Level C" identified in FIG. 20 identifies a plurality of ablation sites, $b_1$, $b_2$, $b_3$ which are grouped in a portion of the pulmonary artery trunk proximal to a left side lateral wall at the upper end of the main pulmonary artery and proximal to a lower wall of the proximal portion of the left pulmonary artery, where those portions meet. For example, as illustrated in FIG. 21, the ablation site $b_1$ is disposed at approximately a left lateral apex of the distal end of the main pulmonary artery, which connects with a lower wall of the proximal end of the left pulmonary artery. Additionally, the ablation sites $b_2$, $b_3$ are disposed, along or substantially along the "Level C" identified in FIG. 20, on the anterior and posterior sides, respectively, of the ablation site $b_1$. These ablation sites $b_1$, $b_2$, and $b_3$ may be targeted to ablate a particular bundled cluster of sympathetical nerves on the left lateral side of the distal end of the main pulmonary artery. These bundled clusters may be approximately 5 mm above the pulmonary valve 514 (FIG. 5) but under the carina 602 (FIG. 6).

Figure 22A:
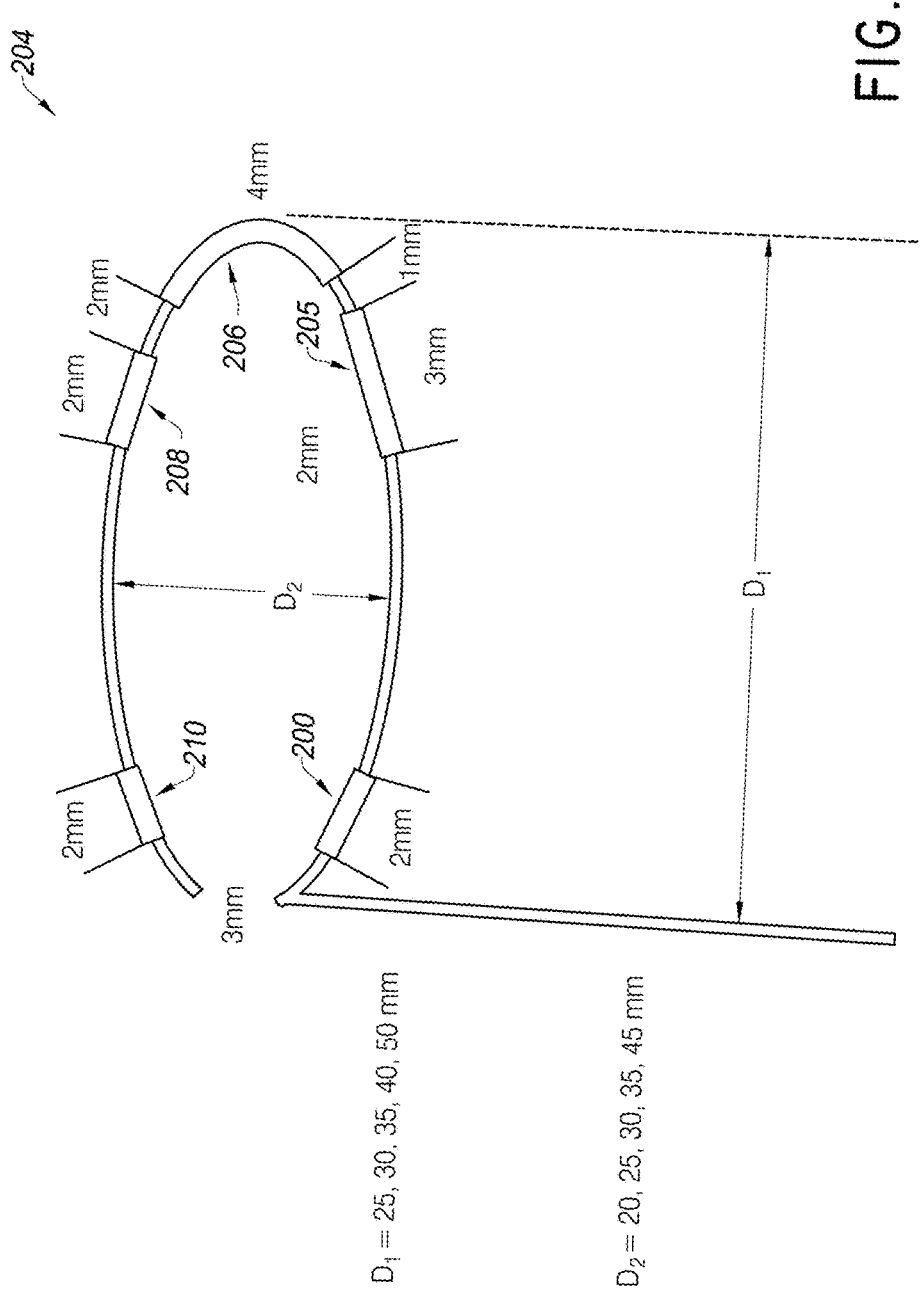
FIG. 22A is an enlarged perspective view of a further embodiment of the catheter of FIGS. 1 and 15A with indicia indicating positions of five (5) RF electrodes.

FIG. 22A illustrates a further embodiment of the annular ring 4 illustrated and described above with reference to FIG. 1 and FIG. 15B. The embodiment of the annular ring 4 illustrated in FIG. 22A is identified with the reference 204. The annular ring 204 illustrated in FIG. 22A can be constructed in accordance with the description set forth above with regard to the annular ring 4 and can be used with the handheld device 1 (FIG. 1), except with regard to the differences described below.

As shown in FIG. 22A, the annular ring 204 can have a fewer number of electrodes than that included in the annular ring 4 described above. In the illustrated embodiment, the annular ring 204 includes five electrodes, 200, 205, 206, 208, 210. Additionally, the annular ring 204 is provided with and configured to conform to (or be biased to) an oval shape, when in its deployed/relaxed state. In its deployed/relaxed state, the annular ring 204 may be substantially planar. Also, in its deployed/relaxed state, the annular ring 204 may be substantially orthogonal, and optionally perpendicular, to a portion of the flexible end 3 of the catheter body connected with the annular ring 204. As illustrated in FIG. 22A, in its deployed state, the annular ring 204 can have a diameter $D_1$ along its major axis. The diameter $D_1$ is larger than the second diameter $D_2$ along the minor axis of the annular ring 204. Such a configuration provides the angular ring 204 with an oval shape, when in its deployed state. The electrodes 200, 205, 206, 208, 210 of the annular ring 204 can be sized in space with the dimensions identified in FIG. 22A, or other dimensions. Also, in certain embodiments, the annular ring 204 may be elliptical and optionally substantially planar. Optionally, such an elliptical ring can be less than a complete loop. For example, the distal end of the annular ring 204 may not curve 360 degrees back to the proximal end of the annular ring but may curve around by an angle of less than 360 degrees (for example by curving at an angle of 270 degrees to 359 degrees). In certain embodiments, the proximal end of the annular ring may be separated by a distance of 3 mm as illustrated in FIG. 22A due to not curving 360 degrees back to the proximal end of the annular ring 204.

With continued reference to FIG. 22A, the electrodes 206, 205, 208 can be arranged and sized to provide for selective ablation of a pulmonary artery corresponding to the ablation sites $b_1$, $b_2$, $b_3$ described above with reference to FIG. 21. Further, the electrodes 206, 205, 208 can have different sizes. In some embodiments, the electrode 206, configured and sized to accommodate denervation of the site $b_1$ can be larger than the electrodes 205, 208. Further, in some embodiments, the electrode 205 can be larger than the electrode 208. For example, the electrode 206 for ablation at $b_1$ may be 4 mm long while the electrode 205 for ablation at $b_2$ may be 3 mm long and the electrode 208 for ablation at $b_3$ may be 2 mm long. Other arrangements, configurations, and sizes can also be used. The electrode 206, for ablation at $b_1$, may be located at an end of diameter $D_1$ and/or straddle an apex of the major axis of annular ring 204.

With continued reference to FIG. 22A, the annular ring 204 can be constructed with several sizes. For example, FIG. 22A includes examples of diameters $D_1$, $D_2$ that can be used for five different sizes of the annular ring 204. The diameters $D_1$, $D_2$ for those five different sizes can be combined in the following listed pairs of diameters (in millimeters), which are listed in the format $(D_1, D_2)$: (25, 20), (30, 25), (35, 30), (40, 35), and (50, 45). Thus, in some embodiments, the diameter $D_1$ is 5 mm larger than the diameter $D_2$. Other sizes and proportions can also be used.

It has been noted that in at least some patients, the sympathetic enervation of the pulmonary arteries (PAs) is concentrated mostly about the left proximal PA. There can be relatively less sympathetic enervation of the right PA. The vagus nerve can travel deep (from the PA perspective) to the sympathetic nerves.

In some embodiments, as noted above, effective reduction of PA hypertension (PAH) can be achieved by ablating at 3 sites in the left side only, such as approximately at the locations $b_1$, $b_2$, $b_3$ identified above with reference to FIG. 21. Additional ablations can be omitted. Thus, in some embodiments, ablations can be carried out at or in the vicinity of the ablations locations $b_1$, $b_2$, $b_3$ and further ablations be avoided or omitted.

Figure 22B:
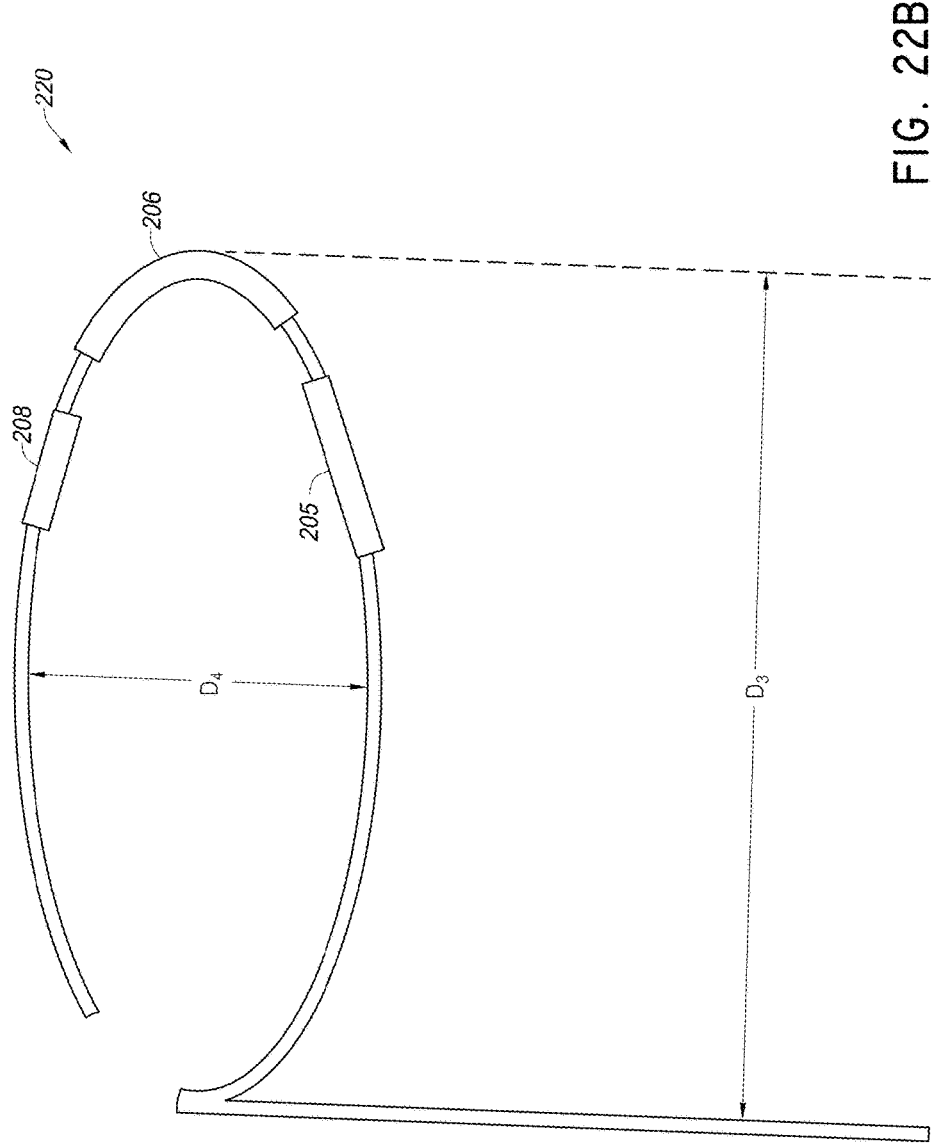
FIG. 22B is an enlarged perspective view of a further embodiment of the catheter of FIG. 22A with three (3) electrodes.

FIG. 22B illustrates a further embodiment of the annular ring 204 illustrated and described above with reference to FIG. 22A. The embodiment of the annular ring 204 illustrated in FIG. 22B is identified with the reference 220.

As illustrated in FIG. 22B, in its deployed state, the annular ring 220 can have a diameter $D_3$ along its major axis. The diameter $D_3$ is larger than the second diameter $D_4$ along the minor axis of the annular ring 220. Such a configuration provides the angular ring 220 with an oval shape, when in its deployed state. For example, FIG. 22B includes examples of diameters $D_3$, $D_4$ that can be used for five different sizes of the annular ring 220. The diameters $D_3$, $D_4$ for those five different sizes can be combined in the following listed pairs of diameters (in millimeters), which are listed in the format $(D_3, D_4)$: (25, 20), (30, 25), (35, 30), (40, 35), and (50, 45). Thus, in some embodiments, the diameter $D_3$ is 5 mm larger than the diameter $D_4$. Other sizes and proportions can also be used.

The annular ring 220 may be configured for the ablation of three sites with electrodes 206, 205, and 208 at approximately at the locations $b_1$, $b_2$, $b_3$ identified above with reference to FIG. 21 and FIG. 22A. The electrode 206, for ablation at $b_1$, may be located at an end of diameter $D_3$ and/or straddle an apex of the major axis of annular ring 220. The electrodes 208, 206, and 205 of the annular ring 220 can be sized in space with the dimensions identified in FIG. 22A, or other dimensions.

In some embodiments, the tissue temperature is raised to 50° C., (range) 48°-52°, for example, by applying RF energy to each of the 3 sites $b_1$, $b_2$, $b_3$ for 2 minutes each. As noted above, optionally, additional ablations can be omitted.

The generator can be configured to, and can be operated to, deliver 3-15 watts of RF energy. In some embodiments, it has been observed that an immediate decrease in PA blood pressure of at least about 10% can be achieved by ablating the three sites $b_1$, $b_2$, $b_3$ as described above. Such a physiological change can serve as immediate feedback and can be used to further guide treatment.

In some animals, visualization of the sympathetic nerves shows thinning of the axons following RF ablation. In humans with PAH and in animals (treated with MCHT to produce PAH experimentally), there is evidence of vascular remodeling 3 months post treatment, with some resolution of HTN induced wall thickening. For some patients, 1-2 years after treatment, the initial improvement in PAH note above persists for those intervals following treatment.

The efficacy of the PADN procedure versus standard pharmacotherapy for the treatment of PAH with different etiologies was investigated in an additional study. In the additional study, 28 patients with PAH were assigned to standard medication and the PADN procedure sequentially. The PADN procedure was associated with significant improvements in 6-minute walk distance (6MWD) and hemodynamics six months following the PADN procedure. Also, the PADN procedure had less frequent PAH-related events after 6- to 12-month following the PADN procedure.

The additional study included a total of 28 patients (11 males and 17 females, with an average age of 49 years). As described in Table, 1, there were 8 patients with IPAH, 9 with PH from LHD, 4 with connective tissue disease, 3 with chronic thrombolitic PH and 4 with congenital heart disease after surgical repairing. The mean time interval from the diagnosis of PAH/PH to the present study was 4.24 years. During wash-out period, there was 1 patient with LHD having the worsening of symptom needed diuretic treatment.

TABLE 1

Baseline characteristics

| Variables | Results |
|---|---|
| Patient number, n | 28 |
| Male, n (%) | 11 (39.3) |
| Age, yr | 49 ± 17 |
| Etiology, n (%) | |
| IPAH | 11 (39.3) |
| LHD | 8 (28.6) |
| CTD | 2 (7.1) |
| CTEPH | 3 (10.7) |
| CHDSR | 4 (14.3) |
| Time from diagnosis to enrolling, yr | 4.24 ± 7.13 |
| Presentation, n (%) | |
| Chest pain | 8 (28.6) |
| Syncope | 4 (14.3) |
| Fatigue | 27 (96.4) |
| Dyspnea | 27 (96.4) |
| Medication at screening, n (%) | |
| Diuretics | 23 (82.1) |
| Calcium-channel antagonist | 4 (14.3) |
| Beta-blocker | 8 (28.6) |
| Prostacyclin | 23 (82.1) |
| 5'-PDE | 10 (35.7) |
| ET receptor antagonist | 5 (17.9) |
| Digoxin | 13 (46.4) |

IPAH, idiopathic pulmonary hypertension;
LHD, left heart disease;
CTD, connective tissue disease;
CTEPH, chronic thrombolytic pulmonary hypertension;
CHDSR, congenital heart disease after surgical repair;
5'-PDE, phosphodiesterase type 5 inhibitor Patients with a resting mean PAP (mPAP)≥25 mmHg with WHO functional class II-IV PAH were included in the additional study. Particularly, for the patients with pulmonary hypertension (PH) secondary from left heart disease (LHD), additional requirements included a pulmonary vessel resistance (PVR)>2.5 woods unit and a pulmonary arterial obstructive pressure (PAOP)>15 mmHg at rest. None of the patients had active inflammation or cancer. Also, none of the patients had PH secondary from portable hypertension and drug or toxin exposure. The study protocol was approved by the Institute Research Board (Nanjing Medical University).

A wash-out consisting of 5 half-lives was performed for all the patients. All the patients who met the above inclusion and exclusion criteria were included and entered into the first wash-out period (defined as stopping all medications for at least 5 half-lives, with the exception of warfarin) as right heart catheterization and adenosine test for all patients were not performed before study. Warfarin was continuously prescribed. Otherwise, aspirin (100 mg/d) and Plavix (75 mg/d) were prescribed instead of warfarin for the patients who were intolerable to warfarin. Immediately after the PADN procedure, the standard medication for PAH were stopped for all the patients.

If the patients were taking multiple drugs, the longest half-lives of any drug was selected. For example, for a patient who was taking bosentan (half-time <5 h) and digoxin (half-time=33 h), then the wash-out period would be 5×33 h=165 h (7 days). After the wash-out period, the drugs were prescribed again and continued for 6 months (Medication treatment). The selection of drugs was left to the physician's discretion based on comprehensive analysis. After 6 months, the patients underwent a second wash-out period of 5 half-lives in order to establish the PADN procedure as a standard alone therapy.

For the PADN procedure, a 7F flow-directed Swan-Ganz catheter (Edwards, USA) was inserted percutaneously in the patients who were under local anesthesia into an internal jugular vein for the measurements of the resting RAP, sRVP, sPAP, mPAP, PAOP, and cardiac output (CO) values. The PVR [=(mPAP-PAOP)/CO] was then calculated. All the measurements were performed at the end of expiration. If the PAOP measurement was unreliable, the left ventricular end-diastolic pressure was measured and used rather than the PAOP measurement. Two blood samples from the RA, RV and PA were obtained for the measurements of oxygen pressure and saturation. If the difference between the oxygen pressure or saturation measurement of these two samples was >7%, further sampling was performed to identify the location of the left-to-right shunt.

Figures 23A, 23B, 23C:
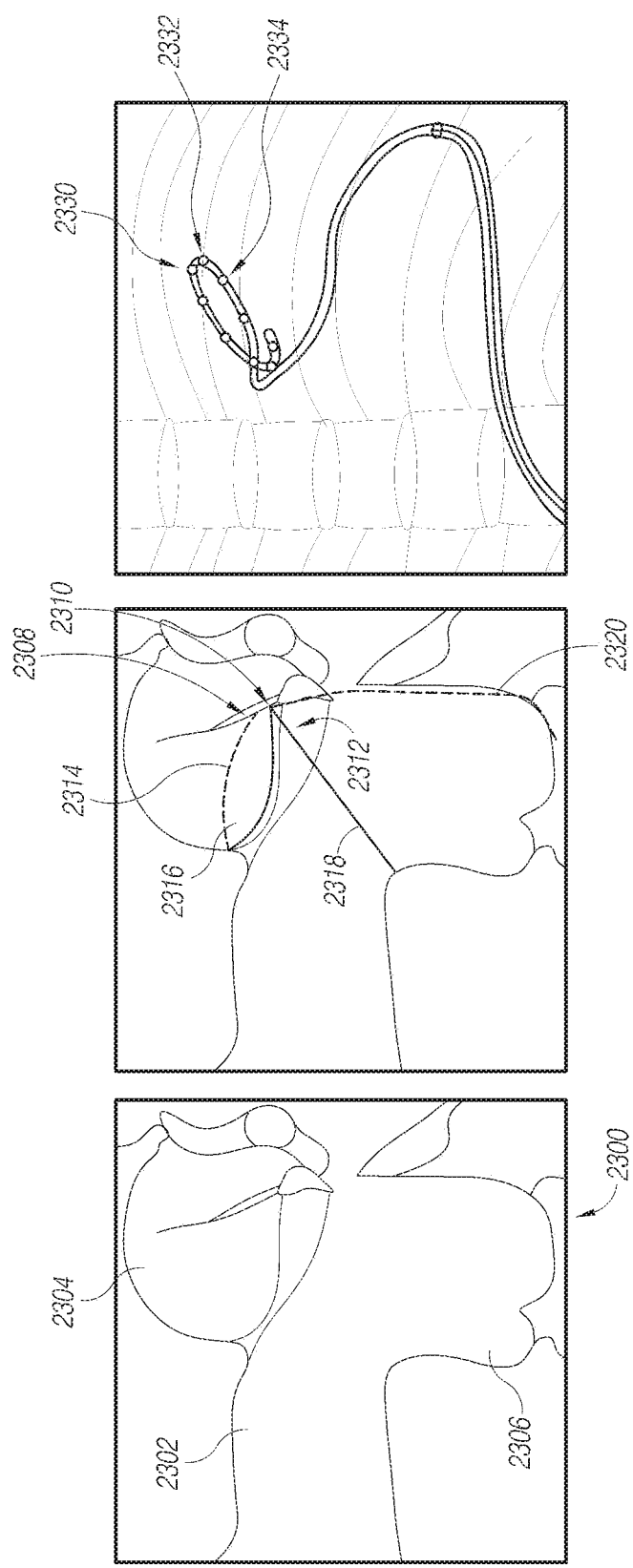
FIGS. 23A-23C are angiographs illustrating parts of the PADN procedure.

The PADN procedure was performed at three sites around the conjunctional area between the distal main trunk and the ostial left branch. FIG. 23A illustrates an anterior-posterior and cranial (20°) view of pulmonary arterial angiograph 2300. Specifically, the angiograph 2300 illustrates the RPA 2302, MPA 2306 and LPA 2304 of a heart of one of the patients. FIG. 23B illustrates the angiograph of FIG. 23A with a line representing the lateral wall of MPA 2320, a line 2318 representing the anterior wall of the LPA. The crossing site by these two lines 2312 and 2316 is the point 2310. The crossing site by a line 2314 representing the posterior wall of LPA and the line 2320 representing a wall of the MPA is the point 2308 which is 1-2 mm posteriori to the point 2310. The line 2316 starts from the inferior wall of RPA and ends at the point 2310, the point 2312 localizes at this level and 1-2 mm anteriorly to the point 2310. FIG. 23C illustrates the angiograph of FIG. 23A with a catheter with 10 electrodes is positioned at the distal MPA. In FIG. 23C, electrode 2332 matches with point 2310, electrode 2330 matches with point 2308 and electrode 2334 matches with point 2312. The following ablation parameters were programmed at each point: a temperature of 45° C.-50° C., energy ≤15 W, and a time of 120 s. The procedure would cease for 10 seconds if the patient felt intolerable chest pain during the procedure. The EKG and pressure lines (including cardiac output) were monitored and continuously recorded throughout the PADN procedure.

The patients were monitored in the CCU for at least 24 hours. All measurements were repeated post-procedure, at 24 hours, at 3 months, at 6 months, and at 12 months. Magnet resonance image (MRI) and CT scanning of the pulmonary artery were performed before the PADN procedure and at 6 months after the PADN procedure.

The success of a PADN procedure was defined as the reduction of sPAP or mPAP immediately after the procedure or at 24 hour ≥10% compared to the baseline values, without intra-procedural complications. The primary endpoint of the additional study was the difference in 6MWD after the 6 months between the medication and PADN procedure. The secondary endpoints included composite and individual PAH-related events including the worsening of PAH, the initiation of treatment with the intravenous or subcutaneous injection of drugs, lung transplantation, atrial septostomy or all-cause death. Repeat hospitalization also served as a secondary endpoint.

For assessing the 6MWD, baseline blood samples were obtained for the analysis of N-terminal brain natriuretic peptide (NT-pro BNP) levels prior to administering the 6MWD. The 6MWD, the Borg scale and the WHO functional class at rest and during exercise were estimated and recorded by a physician who was blinded to the study design. The 6MWD has been selected as an endpoint in previous studies of PAH patients. Notably, the 6MWD in patients without PAH-related events was higher than that in patients with PAH-related events, which suggests that a 15% reduction in the 6MWD may be clinically meaningful. This result supports the use of a 15% reduction in the 6MWD as a criterion for PAH worsening in clinical studies. Also, PAP, RAP and PVR are useful parameters correlated with the prognosis of the PAH patients. A sPAP between 50-70 mmHg and RAP>8 mmHg were markers indicating the severity of PAH disease. The 6MWD improvement after the PADN procedure was paralleled by an improvement in RAP, sPAP and mPAP. However, a correlation between the PA hemodynamics at baseline or post-medication with 6MWD was not established, most likely because the improvement of skeletal blood flow without a change in PA hemodynamics may also account for the improvement of 6MWD.

For the echocardiographic measurements, all echocardiograms were performed (Vivid 7, General Electric Co., Easton Turnpike, Conn., us) and interpreted in the Nanjing Echocardiographic Laboratory following the recommendations of the American Society of Echocardiography. Digital echocardiographic data that contained a minimum of 3 consecutive beats (or 5 beats in cases of atrial fibrillation) were acquired and stored. RV systolic pressure (sRVP) is equal to systolic PAP (sPAP) in the absence of pulmonary stenosis. sPAP is equal to the sum of right atrial (RA) pressure (RAP) and the RV to RA pressure gradient during systole. RAP was estimated based on the echocardiographic features of the inferior vena cava and was assigned a standard value. The RV to RA pressure gradient was calculated as $4v_t^2$ using the modified Bernoulli equation in which $v_t$ is the velocity of the tricuspid regurgitation jet in m/s. mPAP was estimated according to the velocity of the pulmonary regurgitation jet in m/s. The tricuspid excursion index (Tei) is defined as (A−B)/B in which A is the time interval between the end and the onset of tricuspid annular diastolic velocity, and B is the duration of tricuspid annular systolic velocity (or the RV ejection time).

Table 2 provides data indicating how the 6MWD increased from 361±112 m to 373±111 m (p=0.009) after 6-month Medication treatment and from 358±115 m to 423±98 m (p<0.001) 6-month after PADN procedure, in line with the significant reduction of the NT-pro BNP and WHO functional class.

TABLE 2

Comparison of measurements before and after treatment

|  | Medication (n = 28) | | | PADN (n = 28) | | |
| --- | --- | --- | --- | --- | --- | --- |
|  | Prior-to | 6-month | p | Prior-to | 6-month | p |
| NT-pro BNP, pg/ml | 2293 ± 2741 | 1732 ± 1878 | 0.007 | 2669 ± 3178 | 1296 ± 947 | 0.015 |
| WHO class, point | 2.75 ± 0.52 | 2.46 ± 0.58 | 0.009 | 2.75 ± 0.52 | 2.21 ± 0.63 | <0.001 |
| 6MWD, mm | 361 ± 112 | 373 ± 111 | 0.009 | 358 ± 115 | 423 ± 98 | <0.001 |
| Cardiac output | 3.2 ± 0.94 | 3.26 ± 0.89 | 0.221 | 3.25 ± 1.05 | 3.91 ± 1.08 | 0.002 |
| RHC |  |  |  |  |  |  |
| sPAP, mmHg | 91.9 ± 33.0 | 91.5 ± 33.4 | 0.485 | 91.9 ± 33.3 | 78.2 ± 29.4 | <0.001 |
| mPAP, mmHg | 56.1 ± 21.1 | 55.9 ± 21.2 | 0.762 | 56.7 ± 21.8 | 48.9 ± 19.2 | <0.001 |
| PCWP, mmHg | 13 ± 7.7 | 13.8 ± 6.9 | 0.365 | 12.5 ± 8.6 | 12.9 ± 6.3 | 0.788 |
| mRAP, mmHg | 11.5 ± 4.2 | 11.8 ± 4.6 | 0.442 | 11.4 ± 4.7 | 8.8 ± 3.4 | 0.001 |
| sRVP, mmHg | 89.3 ± 31.2 | 91.3 ± 32.1 | 0.255 | 89.3 ± 31.6 | 83.0 ± 34.7 | 0.147 |
| PVR, woods unit | 13.8 ± 7.6 | 13.6 ± 6.9 | 0.721 | 14.3 ± 8.6 | 9.7 ± 6.8 | 0.002 |
| Cardiac echo |  |  |  |  |  |  |
| mPAP, mmHg | 47.9 ± 24.2 | 45.6 ± 23.2 | <0.001 | 47.4 ± 24.8 | 38.1 ± 16.5 | 0.002 |
| mRAP, mmHg | 11.8 ± 3.1 | 11.1 ± 2.8 | 0.043 | 11.8 ± 3.1 | 8.9 ± 3.1 | <0.001 |
| sRVP, mmHg | 96.0 ± 87.9 | 87.9 ± 26.9 | <0.001 | 96.1 ± 31.7 | 78.6 ± 23.3 | <0.001 |
| sPAP, mmHg | 98.1 ± 29.5 | 87.2 ± 25.2 | <0.001 | 98.2 ± 32.2 | 79.9 ± 24.6 | <0.001 |
| Pericardial fluid, mm | 1.11 ± 1.64 | 1.43 ± 1.93 | 0.059 | 1.96 ± 2.89 | 0.85 ± 0.89 | 0.002 |
| RV Tei, % | 0.59 ± 0.17 | 0.55 ± 0.16 | 0.029 | 0.69 ± 0.09 | 0.36 ± 0.09 | <0.001 |

Figure 24A:
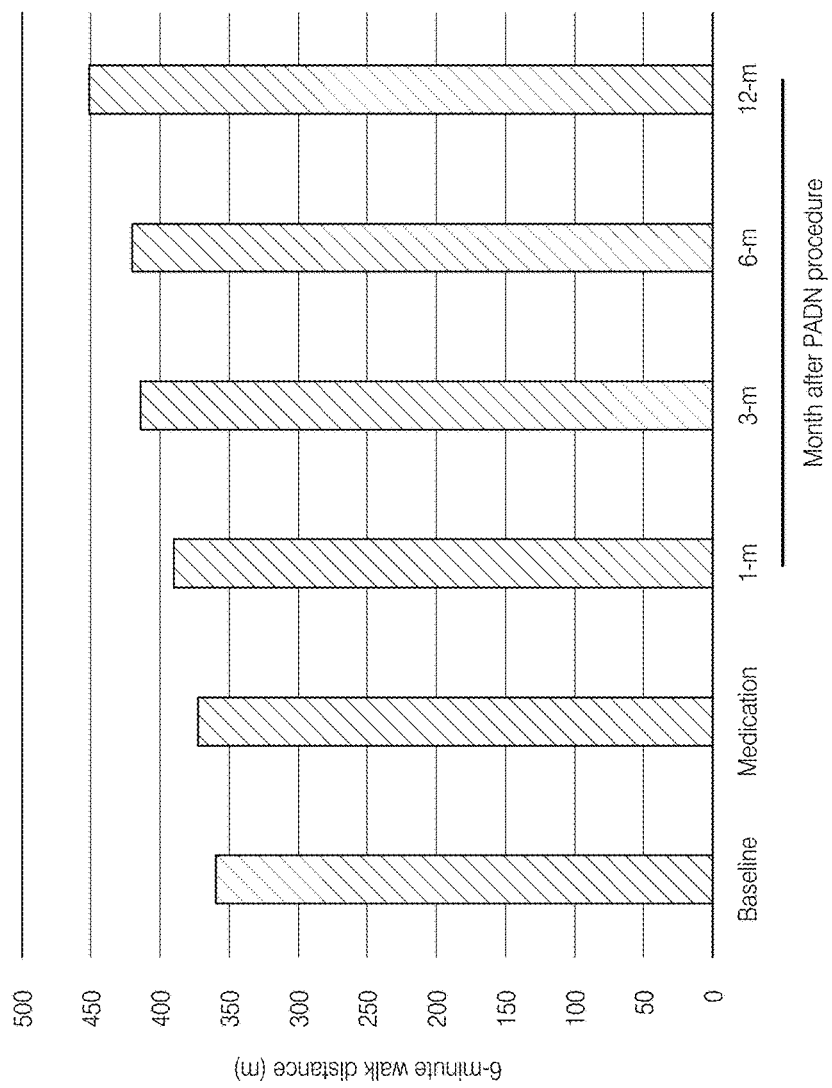
FIG. 24A is a chart illustrating the 6-minute walk distance (6MWD) at the 6-month follow-up minus the baseline 6MWD in the Medication treatment and the PADN procedure.
Figure 24B:
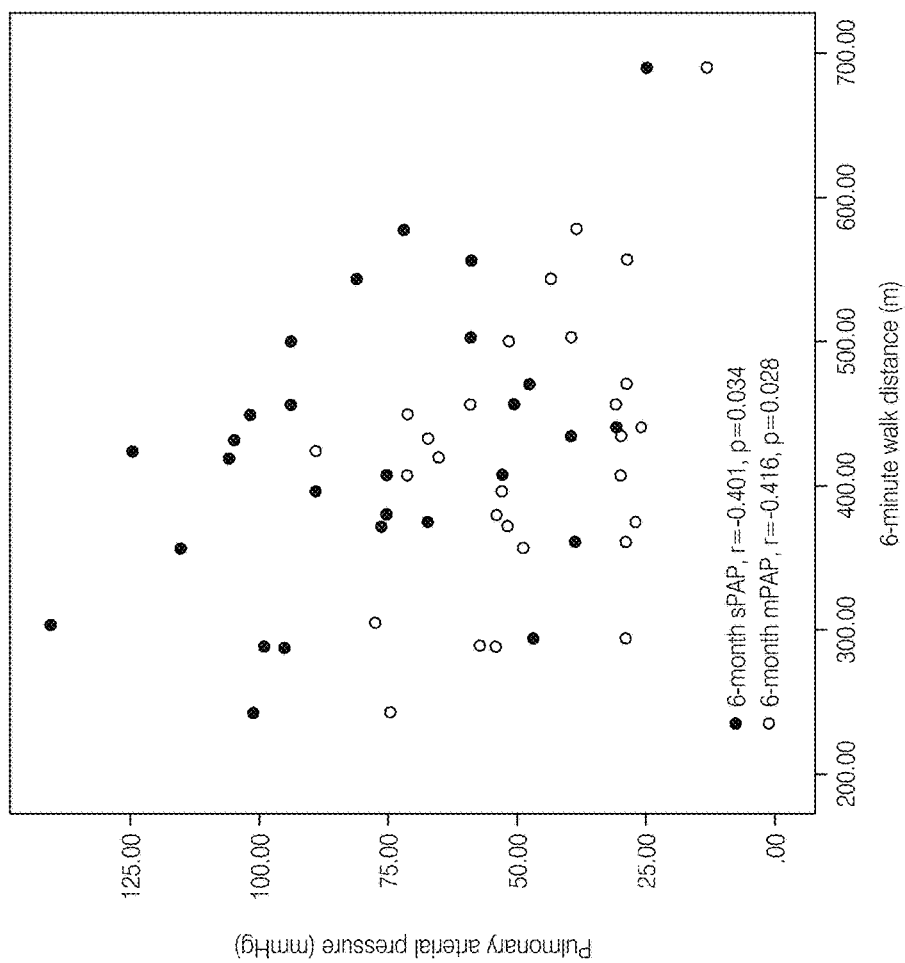
FIG. 24B is a chart illustrating how the 6MWD after the PADN procedure is correlated with a Medication treatment.
Figure 24C:
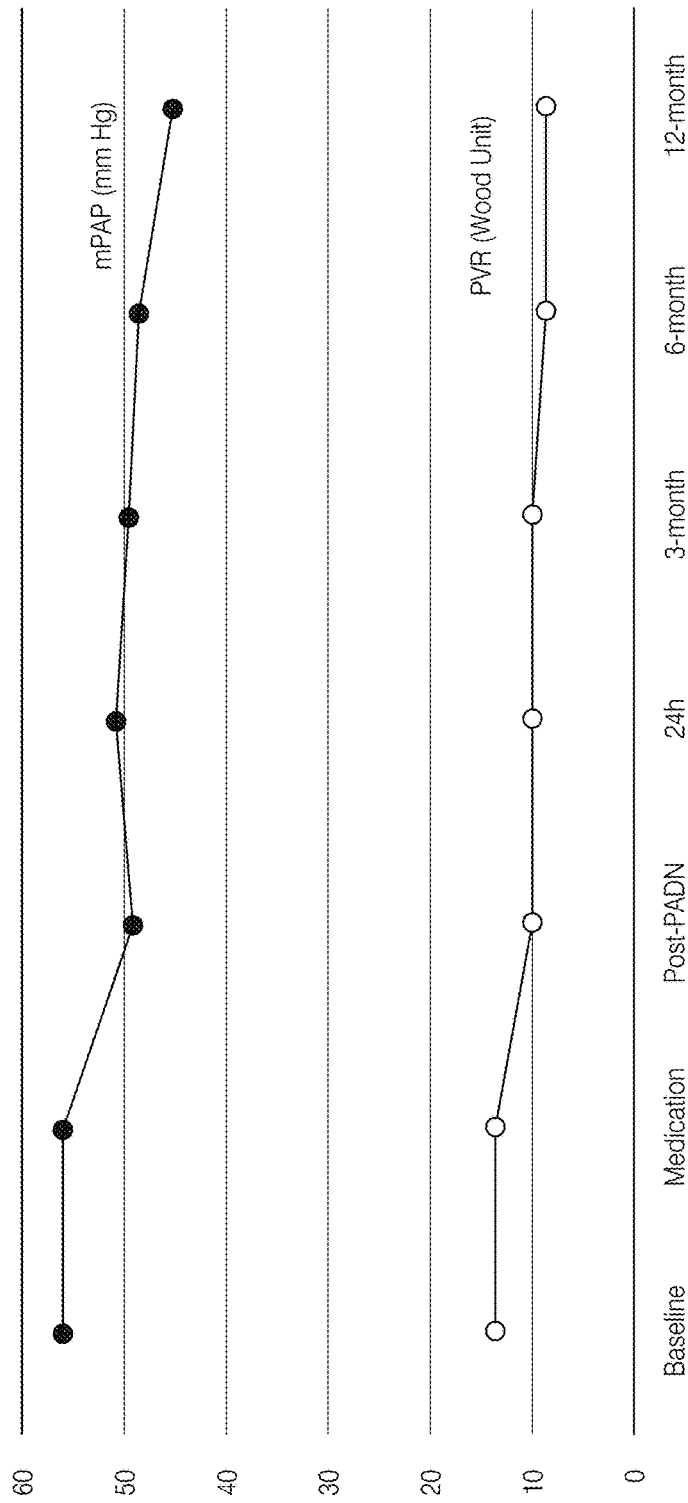
FIG. 24C is a chart illustrating how improvements in hemodynamic and cardiac functions were sustained through a one-year follow-up after the PADN procedure.

PADN, pulmonary artery denervation;
NT-pro BNP, N terminal-pro brain natriuretic peptide;
6MWD, 6-minute walk distance;
RHC, right heart catheterization;
sPAP, systolic pulmonary arterial pressure;
mPAP, mean pulmonary arterial pressure;
mRAP, mean right atrial pressure;
sRVP, systolic right ventricular pressure;
PVR, pulmonary vessel resistance;

There was a significant difference in the increase in 6MWD at the 6-month follow-up between the Medication (13±24 m) and the PADN procedure (65±85 m) (95% CI: −21.34~−3.49, p=0.002), coupled with the significant improvement of hemodynamic after PADN procedure. The PADN procedure was associated with less frequent PAH-related events at the 6-month (10.8%) and 12-month (17.9%) follow-up, compared to 42.9% after 6-month Medication treatment (all p<0.05). As illustrated in Table 3 and FIG. 24A, the Δ6MWD (defined as the 6MWD at the 6-month follow-up minus the baseline 6MWD) was +13±24 m (+3.9% increase) in the Medication treatment, which was significantly different to the +65±85 m (+23.9% increase, 95% CI: −21.34~−3.49, p=0.002) at the 6-month and +95±61 m (+34.9% increase) at one-year after the PADN procedure.

and Tei (−0.34±0.11 points vs. −0.04±0.09 points, p<0.001). As illustrated in FIG. 24C, these improvements were sustained through one-year follow-up after PADN procedure.

Table 4 illustrates how, after the 6-month treatment, a PAH-related event was observed in 12 patients (42.9%) in the Medication treatment and 3 patients (10.8%) in the PADN procedure (p=0.002). These events were mainly driven by the worsening of PAH.

TABLE 3

Comparison of the differences in measurements after 6-month treatments

|  | Medication (n = 28) | PADN (n = 28) | 95% CI | p |
|---|---|---|---|---|
| NT-pro BNP, pg/ml | −562 ± 1009 | −1373 ± 2792 | −42.84~1665.44 | 0.062 |
| WHO functional class | −0.36 ± 0.49 | −0.54 ± 0.58 | −0.10~0.46 | 0.202 |
| 6MWD, m | 13 ± 24 | 65 ± 85 | −21.34~−3.49 | 0.002 |
| % of increase | +3.9% | 23.9% | −0.31~−0.09 | 0.001 |
| Cardiac output | 0.06 ± 0.24 | 0.67 ± 1.05 | −0.10~−0.20 | 0.005 |
| RHC |  |  |  |  |
| sPAP, mmHg | −0.46 ± 3.47 | −13.75 ± 14.1 | 8.38~18.19 | <0.001 |
| mPAP, mmHg | −0.14 ± 2.48 | −7.86 ± 6.10 | 5.26~10.18 | <0.001 |
| PCWP, mmHg | 0.82 ± 4.72 | 0.36 ± 6.96 | −1.63~2.56 | 0.653 |
| mRAP, mmHg | −0.21 ± 2.62 | −2.53 ± 3.75 | 0.70~3.93 | 0.007 |
| sRVP, mmHg | 1.96 ± 8.93 | −6.22 ± 22.07 | 1.76~14.62 | 0.014 |
| PVR, woods unit | −0.17 ± 2.56 | −4.59 ± 7.06 | 1.99~6.83 | 0.001 |
| Cardiac echo |  |  |  |  |
| mPAP, mmHg | −2.36 ± 2.78 | −9.28 ± 13.93 | 1.98~11.86 | 0.008 |
| mRAP, mmHg | −0.54 ± 1.57 | −2.86 ± 2.86 | 1.20~3.44 | <0.001 |
| sRVP, mmHg | −8.07 ± 9.73 | −17.54 ± 16.97 | 4.78~14.15 | <0.001 |
| sPAP, mmHg | −10.89 ± 11.87 | −18.25 ± 16.73 | 3.13~11.58 | 0.001 |
| Pericardial fluid, mm | 0.11 ± 0.93 | −0.74 ± 2.63 | −1.04~2.47 | 0.036 |
| RV Tei, % | −0.04 ± 0.09 | −0.34 ± 0.11 | 0.24~0.35 | <0.001 |

CI, confidence interval;
PADN, pulmonary artery denervation;
NT-pro BNP, N terminal-pro brain natriuretic peptide;
6MWD, 6-minute walk distance;
RHC, right heart catheterization;
sPAP, systolic pulmonary arterial pressure;
mPAP, mean pulmonary arterial pressure;
mRAP, mean right atrial pressure;
sRVP, systolic right ventricular pressure;
PVR, pulmonary vessel resistance;

In the Medication treatment, there were 9 patients (32%) whose 6MWD decreased (range from −6 m to −47 m) after the 6-month treatment. Of those 9 patients, 5 patients had an average 6MWD increase of 45 m 6-month after the PADN procedure, whereas no change was observed in 4 patients. Among those 4 patients, there was still no change 6MWD in 1 patient at one-year after the PADN procedure. Finally, there were 2 patients who had no change in 6MWD at one-year follow-up after PADN procedure. As illustrated in FIG. 24B, the 6MWD after the PADN procedure rather than Medication treatment was negatively correlated with mPAP (r=−0.416, p=0.028) and sPAP (r=−0.401, p=0.034).

The study also demonstrated improvement of hemodynamic and cardiac function. The Δ mPAP and ΔCO at 6-month after the PADN procedure were greater than those in the Medication treatment (−7.86±6.10 mmHg vs. −0.14±2.48 mmHg, P<0.001; 0.67±1.05 L/min/1.73 m² vs. 0.06±0.24 L/min/1.73 m², p=0.005, Table 3), with resultant significant differences in the reduction of the pericardial fluid amount (−0.74±2.63 mm vs. +0.11±0.93 mm, p=0.036)

TABLE 4

Clinical follow-up after the 6-month treatments

|  | Medication (n = 28) | PADN (n = 28) | p |
|---|---|---|---|
| PAH-event, n (%) | 12 (42.9) | 3 (10.8) | 0.002 |
| All-cause death | 0 | 0 |  |
| Atrial septostomy | 0 | 0 |  |
| Lung transplantation | 0 | 0 |  |
| Needing IV & IS | 2 (7.2) | 0 |  |
| Worsening of PAH | 10 (36.0) | 3 (10.8) |  |
| Re-hospitalization, n (%) | 12 (38.3) | 4 (14.4) | 0.018 |
| Cost, x10,000 USD/per pt | 3.5 ± 1.2 | 0.6 ± 0.7 | <0.001 |
| Any-cause Death, n (%) | 0 | 0 |  |
| Access site hematoma, n (%) | 0 | 0 |  |
| Aneurysm, n (%) | 0 | 0 |  |
| Thrombus, n (%) | 0 | 0 |  |

PADN, pulmonary artery denervation;
PAH, pulmonary arterial hypertension;
pt, patient;

The mean time from treatment to clinical worsening was 125 days (range of 22 to 166 days) in the Medication treatment, which was significantly shorter than the 166 days (range from 47 to 172 days) reported in the PADN procedure (p=0.01). Re-hospitalization was required in 42.9% of the patients in the Medication compared to 14.4% of the patients in the PADN procedure (as described when p=0.018 in Table 4). There were no access hematomas, aneurysms, thrombus formations or any-cause deaths after the 6-month treatment.

The Δ6MWD was approximately +60 m after PADN procedure and +15 m after the medication treatment. A total of 28 patients were required to achieve significance (2-sided p-value, 80% power). The difference in each variable (at the 6-month period minus the baseline) for each treatment was calculated and compared between the two treatments. The continuous variables were expressed as the mean±SD. A normality test for all the continuous variables was performed using the Kolmogorov-Smirnov and Shapiro-Wilk tests. The differences in the continuous variables between the two treatments were analyzed using a paired t-test or the Mann-Whitney U test when appropriate. The categorical variables were compared using Fisher's exact test. The event-free survival rate was generated using the Kaplan-Meier method and was analyzed with the log-rank test. Statistical significance was defined as a two-sided P value <0.05. All the analyses were performed using the statistical program SPSS 19.0 (SPSS Institute Inc., Chicago, Ill., USA).

For the additional study, a worsening of PAH was defined as the occurrence of all three of the following measurements: a decrease in the 6MWD of at least 15% from baseline, confirmed by a second 6MWD performed on a different day within 14 days of the first measurement; a worsening of the symptoms of PAH; and the need for additional treatment for PAH. A worsening of the symptoms of PAH was defined as any of the following measurements: a change from baseline to a higher WHO functional class (or no change in patients who were in WHO functional class IV at baseline) and the appearance or worsening of signs of right heart failure, which did not respond to oral diuretic therapy. An independent clinical event committee adjudicated, in a blind fashion, all the events related to PAH and all the deaths that were reported up to the end of the treatment.

At the one-year follow-up, there were 5 (17.9%) PAH-related events (2 new events, including 2 sudden deaths). The 6MWD in patients without PAH-related events was 467±100 m, which was higher than the 393±42 m reported in patients who had experienced an event (p=0.018). Accordingly, patients with 6MWD<400 m had higher rate of PAH-related event (44.4%) at one-year after the PADN procedure, compared 5.3% in patients with 6MWD≥400 m (p=0.010).

Therefore, the additional study indicated that the PADN procedure was associated with a significant improvements in 6MWD and hemodynamics at 6-month, with resultant less PAH-related events. For example, the PADN procedure led to a greater improvement of pulmonary arterial hemodynamics with subsequently less frequent PAH-related events and re-hospitalizations.

FIGS. 25A-25H are various views of a digital ablation controller 2500 that can be used in lieu of the controller 100 illustrated in FIGS. 15C-15D. Similar to the controller 100, the digital ablation controller 2500 can be connected to the handle 2 of the catheter for providing ablation energy. For example, the digital ablation controller 2500 can be configured to provide ablation energy and control the electrodes E1-E10 of FIG. 15B.

Generally described, the digital ablation controller 2500 provides for a single, portable housing for both control and feedback during performance of the PADN procedure. The digital ablation controller 2500 may control the amount of power provided to the electrodes 5 from a power source (such as a battery or a power grid) such that the amount of power is within nominal limits for ablation. Also, the digital ablation controller 2500 may enable the storage and retrieval of various patient profiles that may include different configuration settings for catheter configuration and/or provision of power to the electrodes of the catheter.

For example, different patient profiles may include different settings for which the PADN procedure is to be performed with different settings for different electrodes. Also, the digital ablation controller 2500 may include a user interface from which a user or operator of the digital ablation controller may provide manual control and/or enter or retrieve information from the patient profiles.

For example, the user interface may include information on the operational characteristics of the electrodes (such as ablation temperature and time captured by the catheter's sensors) and the user or operator of the digital ablation controller may perform the PADN procedure based upon the operational characteristics of the electrodes. Also, the user or operator of the digital ablation controller may directly select a particular electrode (or electrodes) to activate for ablation from the user interface. Thereby, the digital ablation controller would direct power (such as power from the battery) to the appropriate electrode(s) selected via the user interface.

In certain embodiments, the digital ablation controller may provide automatic control of the PADN procedure based upon feedback from sensors on the catheter. For example, the operational characteristics of the electrodes may be captured by the catheter's sensors and used to regulate aspects of the PADN procedure (such as the amount of time ablation is performed at a particular location based upon the temperature at the location of ablation).

In certain embodiments, the digital ablation controller includes a battery configured to store power at a level sufficient for ablation using one or more electrodes 5 of the multi-pole synchronous pulmonary artery radiofrequency ablation catheter. By directly using the battery, the provision of power to the electrodes is contingent upon stored power rather than power provided ad hoc to the electrodes, such as from power provided by a local power grid. Thereby, the availability of power is not contingent upon power being readily available to the digital ablation controller but rather the digital ablation controller may function independent of the local power grid so long as the battery is sufficiently charged.

FIG. 25A illustrates a top perspective view of the digital ablation controller 2500 in a closed position. The top perspective view illustrates the power cord 2504 connected to the digital ablation controller 2500. As illustrated, the digital ablation controller 2500 may be a single housing configured to provide an interface for control and power for the multi-pole synchronous pulmonary artery radiofrequency ablation catheter. For example, the digital ablation controller 2500 may receive and store power such that the PADN procedure may be performed using the stored (battery) power in the digital ablation controller 2500. Also, the digital ablation controller 2500 may provide precise regulation of power by digitally controlling different aspects of the PADN procedure, such as the particular electrode(s) used for ablation, the power at any particular electrode and the time for ablation. The digital ablation controller 2500 may also provide real time feedback from sensors (such as temperature sensors and/or impedance sensors) disposed at various points on the multi-pole synchronous pulmonary artery radiofrequency ablation catheter (such as at the locations of the electrodes), as discussed in FIGS. 1-4.

Figure 25B:
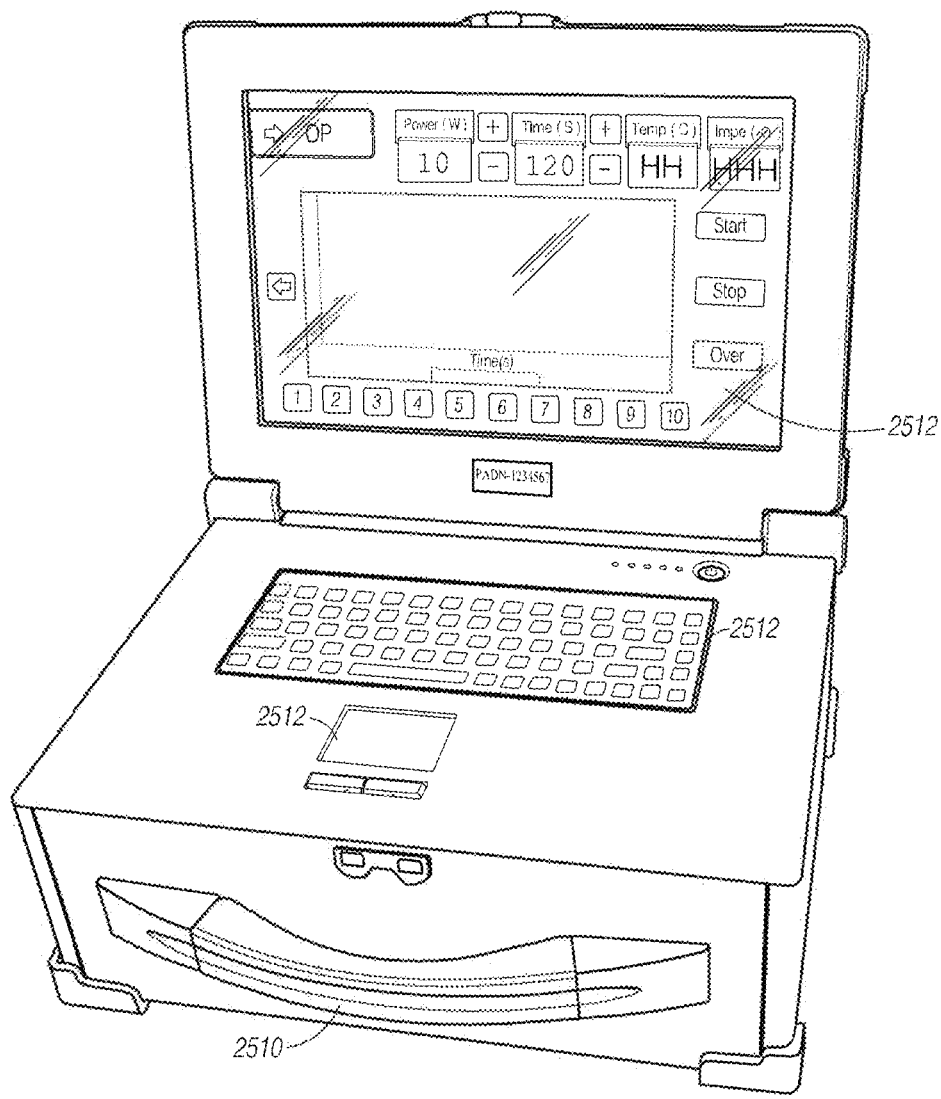
Figure 25C:
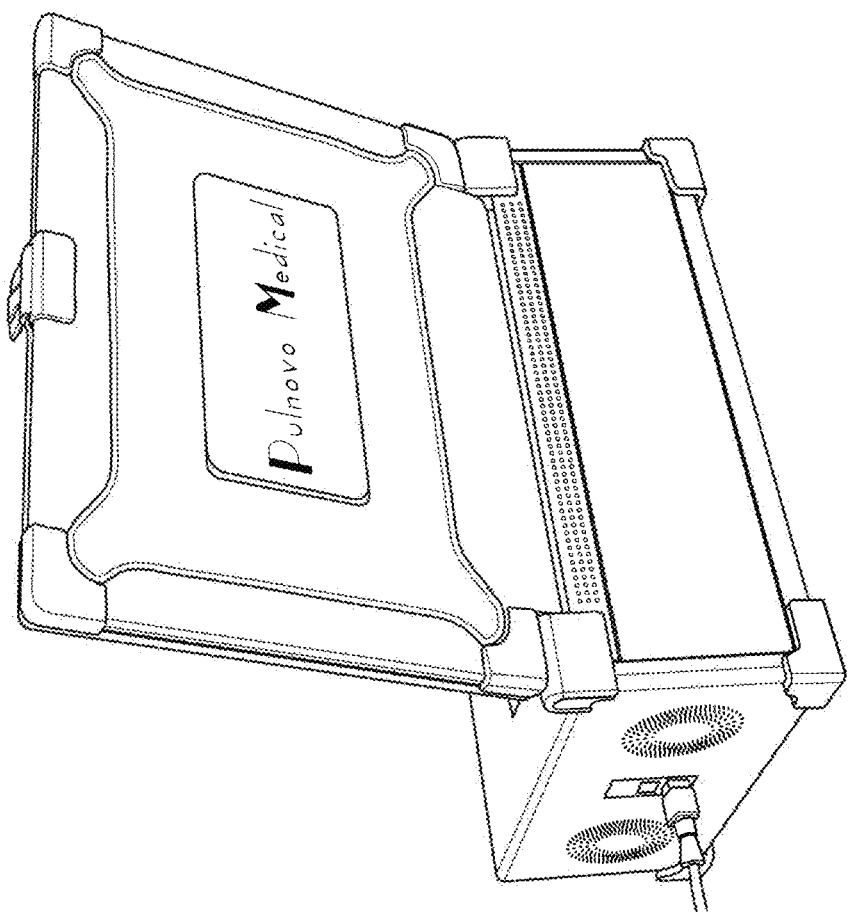

FIG. 25B illustrates a top perspective view of the digital ablation controller 2500 in an open position. The user interface 2512 is visible and usable in the open position of the digital ablation controller 2500. Also, a carrying handle 2510 is illustrated on the digital ablation controller 2500. FIG. 25C illustrates a back perspective view of the digital ablation controller 2500 in the open position.

Figure 25D:
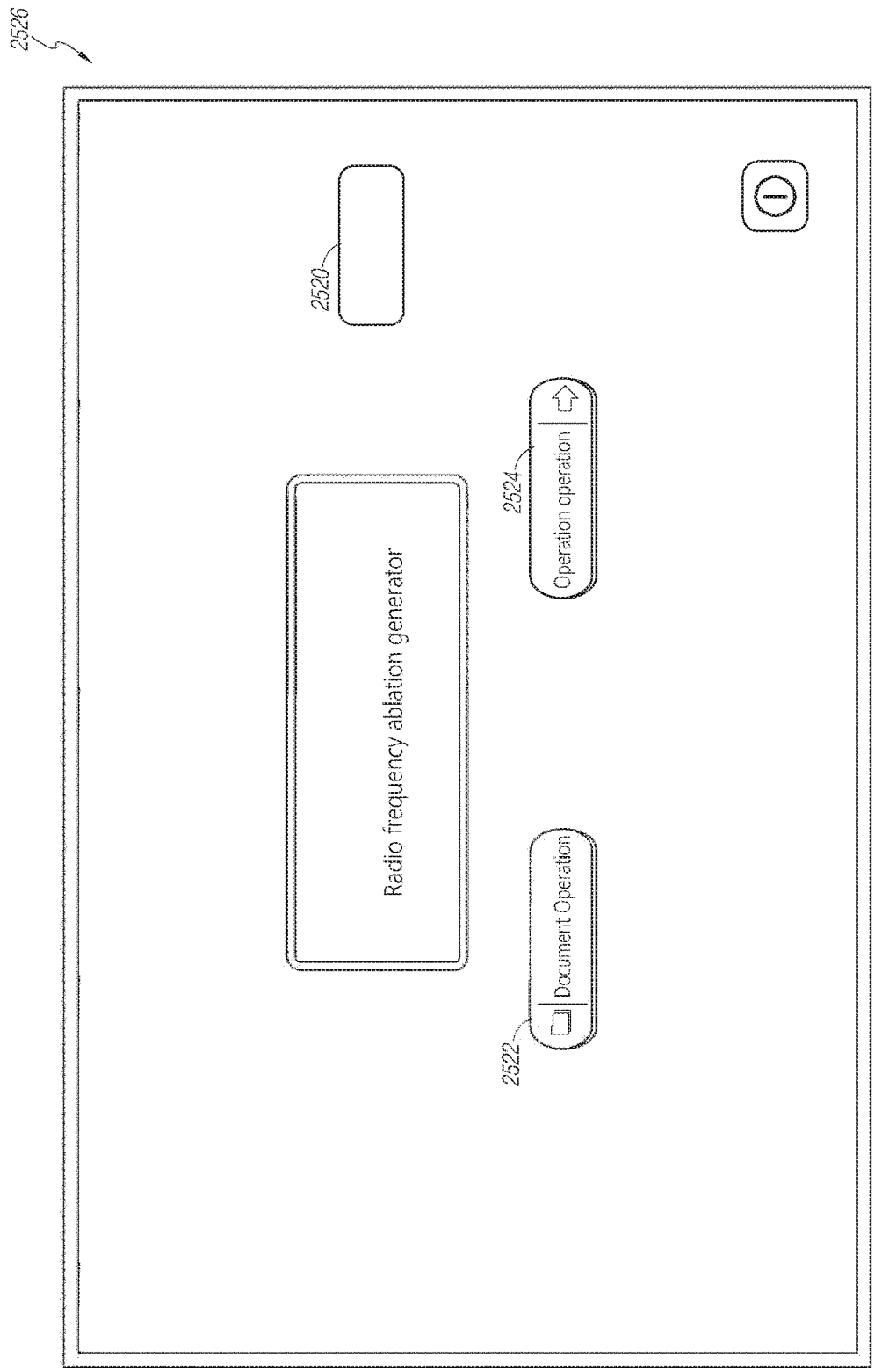

FIG. 25D is a screen shot of an initial user interface 2526 of the digital ablation controller 2500. The initial user interface includes buttons that may be selected to interact with the digital ablation controller 2500. For example, the initial user interface 2526 illustrates a button 2520 for changing a language setting of the user interface 2520, a button 2522 to access data stored in the digital ablation controller 2500 and a button 2524 to begin operation of the digital ablation controller 2500.

Figure 25E:
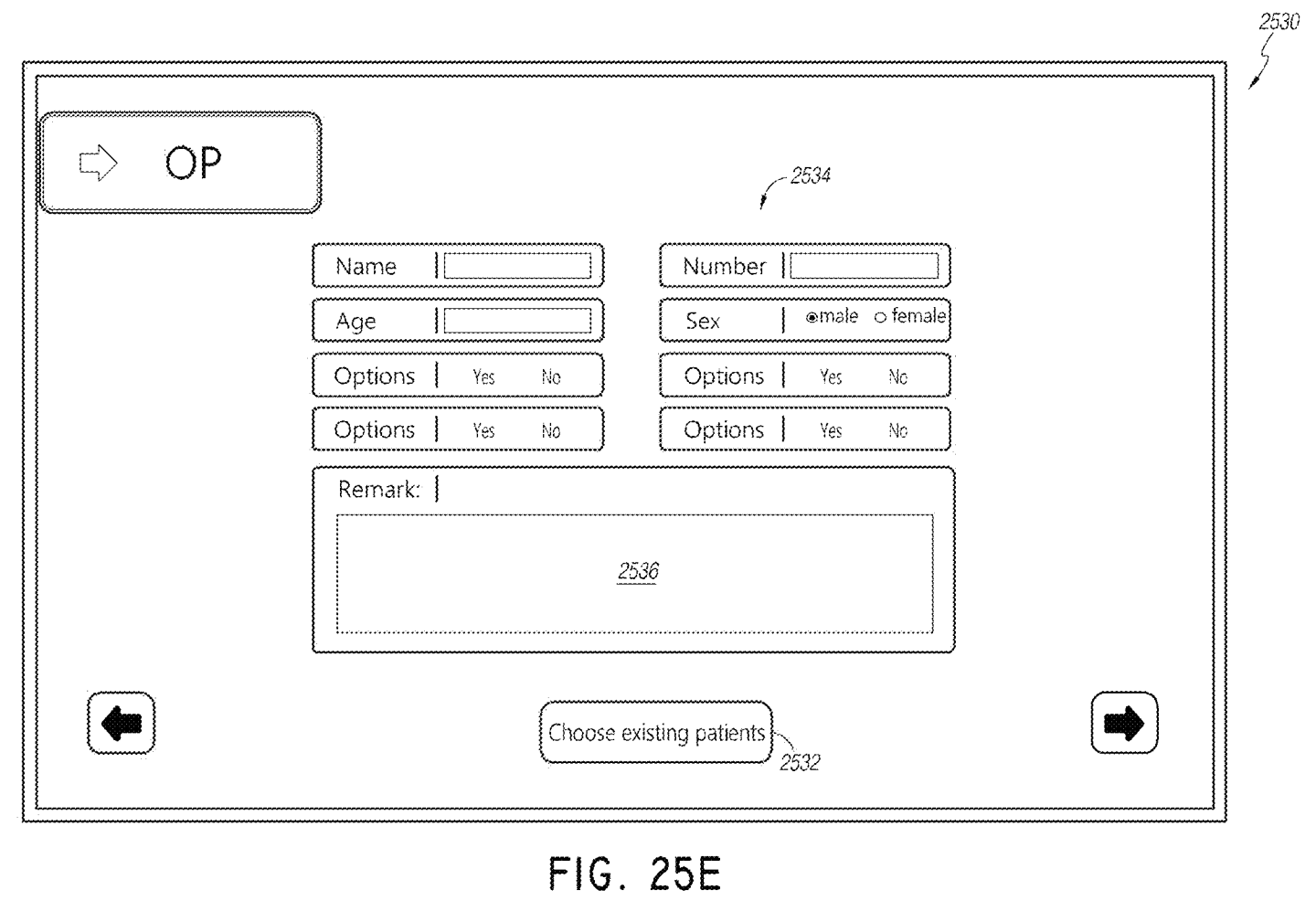

FIG. 25E is a screen shot of the user interface 2530 presenting options for entering patient information for performance of the PADN procedure. The user interface includes a button 2532 to begin browsing existing patient profiles stored in the digital ablation controller 2500. The user interface also includes sections 2534 for inputting information for a new patient profile, such as a patient's name, identification number, age, sex and the selection of various preset operational settings for the digital ablation controller 2500. The user interface also includes a section 2536 to input remarks concerning the patient for the patient profile.

Figure 25F:
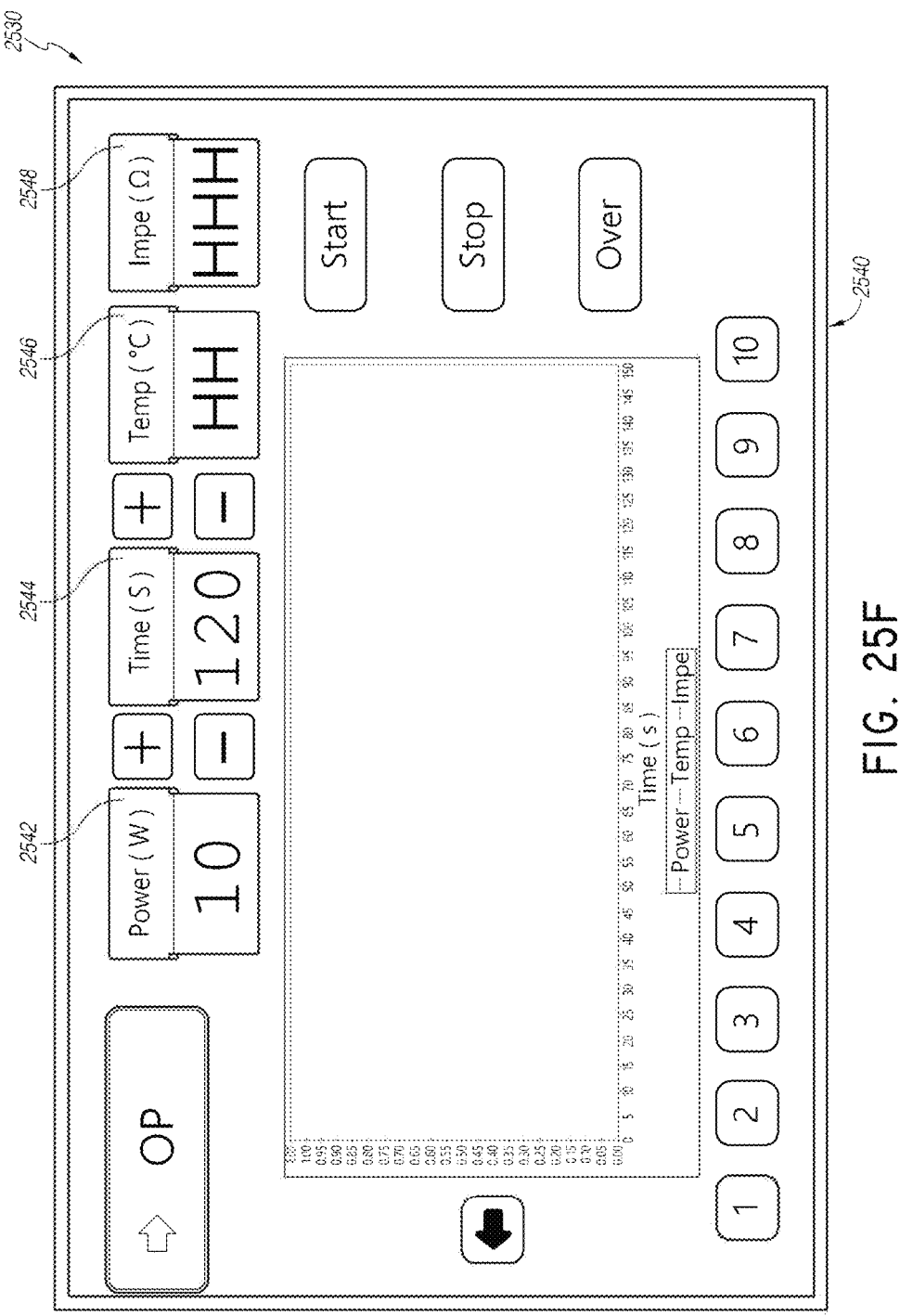

FIG. 25F is a screen shot of a user interface 2540 of the digital ablation controller 2500 at the initiation of the PADN procedure. The user interface 2540 includes information concerning the power level 2542, time 2544, temperature 2546 and impedance 2548 of the electrodes of the catheter. The user interface also includes buttons from which a particular electrode 5 on the annular ring 4 may be selected for activation.

Figure 25G:
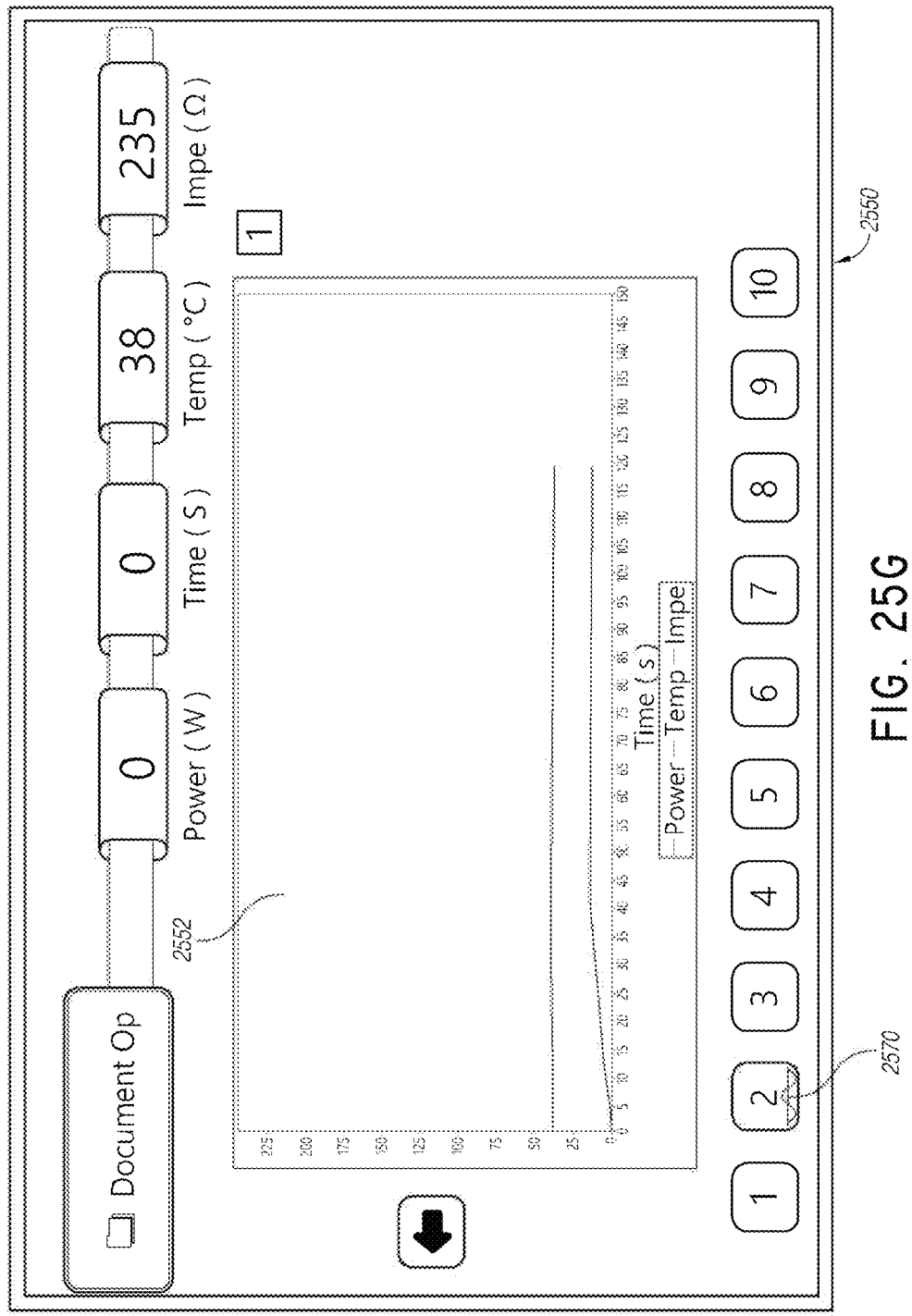

FIG. 25G is a screen shot of a user interface 2550 of the digital ablation controller 2500 during operation. Ablation may be initiated by selecting a button for a particular electrode, such as a button 2570 associated with electrode 2572 designated with the number "2" highlighted on the user interface. The operational relationship of the electrode 2572 between impedance, power and temperature over time is displayed on a graph 2552. Although a single electrode is selected in the user interface and used for ablation in the illustrated embodiment, certain embodiments provide for multiple electrodes selected and used at once for ablation. Also, ablation may be interrupted while switching between electrodes used for ablation. The switching between different electrodes for ablation may be implemented in any manner that allows for energy used for ablation to be guided to different electrodes of the multi-pole synchronous pulmonary artery radiofrequency ablation catheter, such as via digital or analog/solid state switching.

Figure 25H:
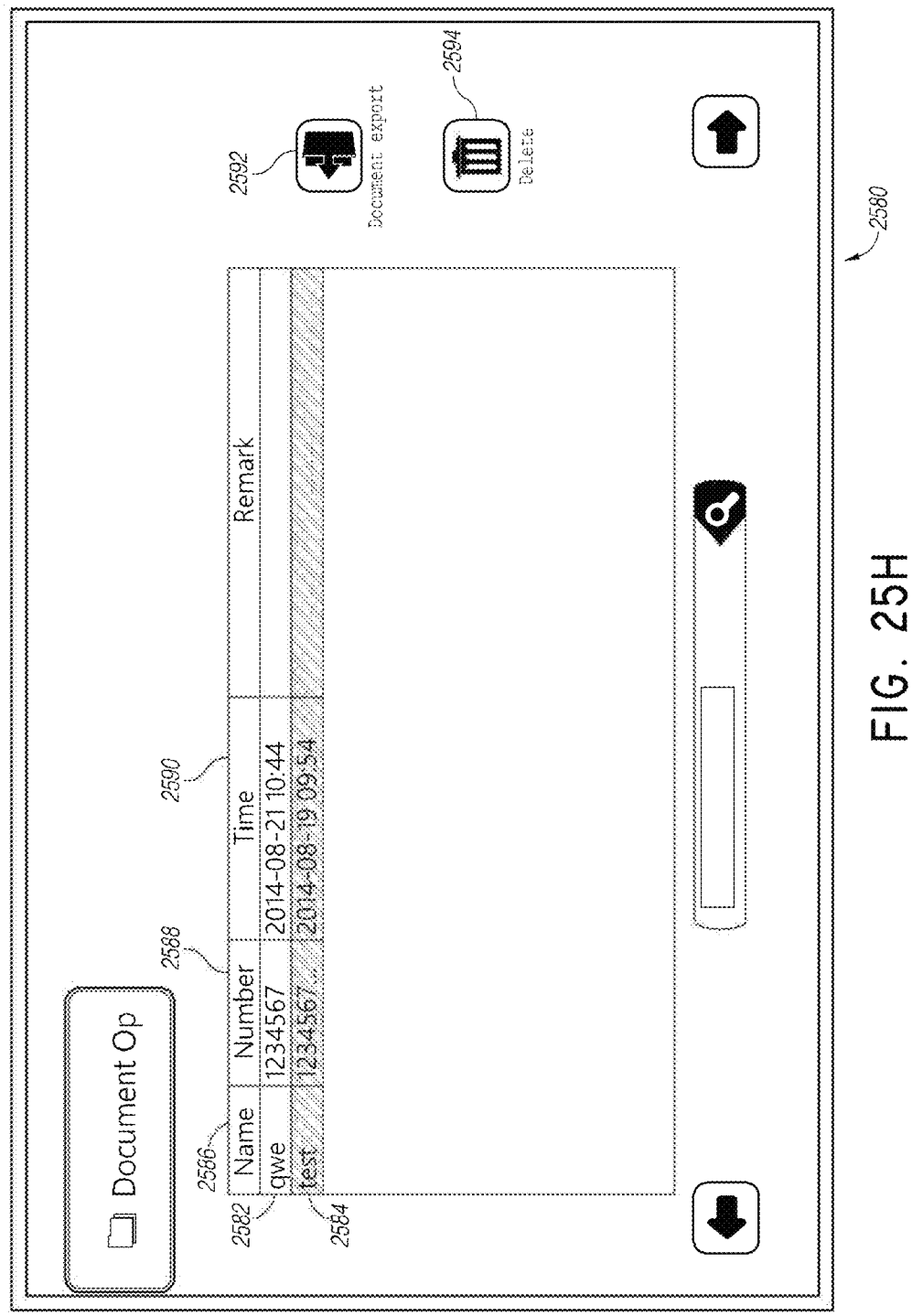

FIG. 25H is a screen shot 2580 of a user interface of the digital ablation controller 2500 presenting information on stored patient profiles. The user interface indicates that there are two patient profiles 2582, 2584 that may be selected. The patient profiles are presented with a name 2586, patient identification number 2588 and time 2590 of last access of the stored patient profile. The user interface also includes buttons 2592 for exporting the various patient profiles and an option button 2594 to delete a selected patient profile.

Figure 26:
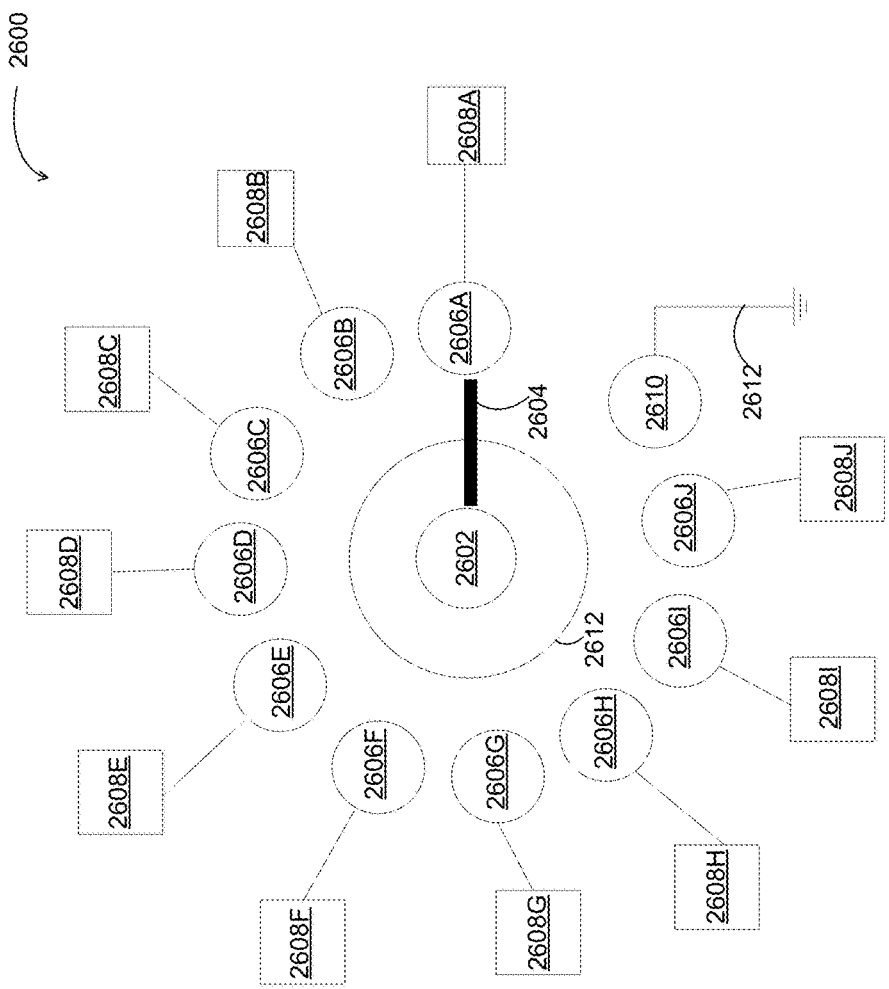
FIG. 26 is a schematic diagram illustrating a mechanical switching system that may be implemented in the controller of FIGS. 25A-25H or the controller of FIGS. 15C-15D.

FIG. 26 is a schematic diagram illustrating a mechanical switching system 2600 that may be implemented in the controller 2500 of FIGS. 25A-25H or the controller 100 of FIGS. 15C-15D. The mechanical switching system 2600 includes a source contact 2602, a mechanical switch 2604, electrode contacts 2606A-J, and a ground contact 2610. The source contact 2602 may be connected with a source of RF energy at a level sufficient for ablation. The electrode contacts 2606A-J may be each connected with a different electrode 2608A-J that may be used for ablation. The ground contact 2610 may be connected to ground 2612. The electrodes 2608A-J may be located at the distal end of the catheter. The mechanical switch 2604 may be actuated as part of a dial or knob 2612 that may be physically moved such that the mechanical switch 2604 connects the source contact 2602 with a particular electrode contact 2606A-J or the ground contact 2610. For example, the mechanical switch 2604 may be actuated by being physically moved in a clockwise or a counter clockwise direction. In the illustrated embodiment, the switch 2604 is positioned to connect the source contact 2602 to the electrode contact 2606A.

Figure 27:
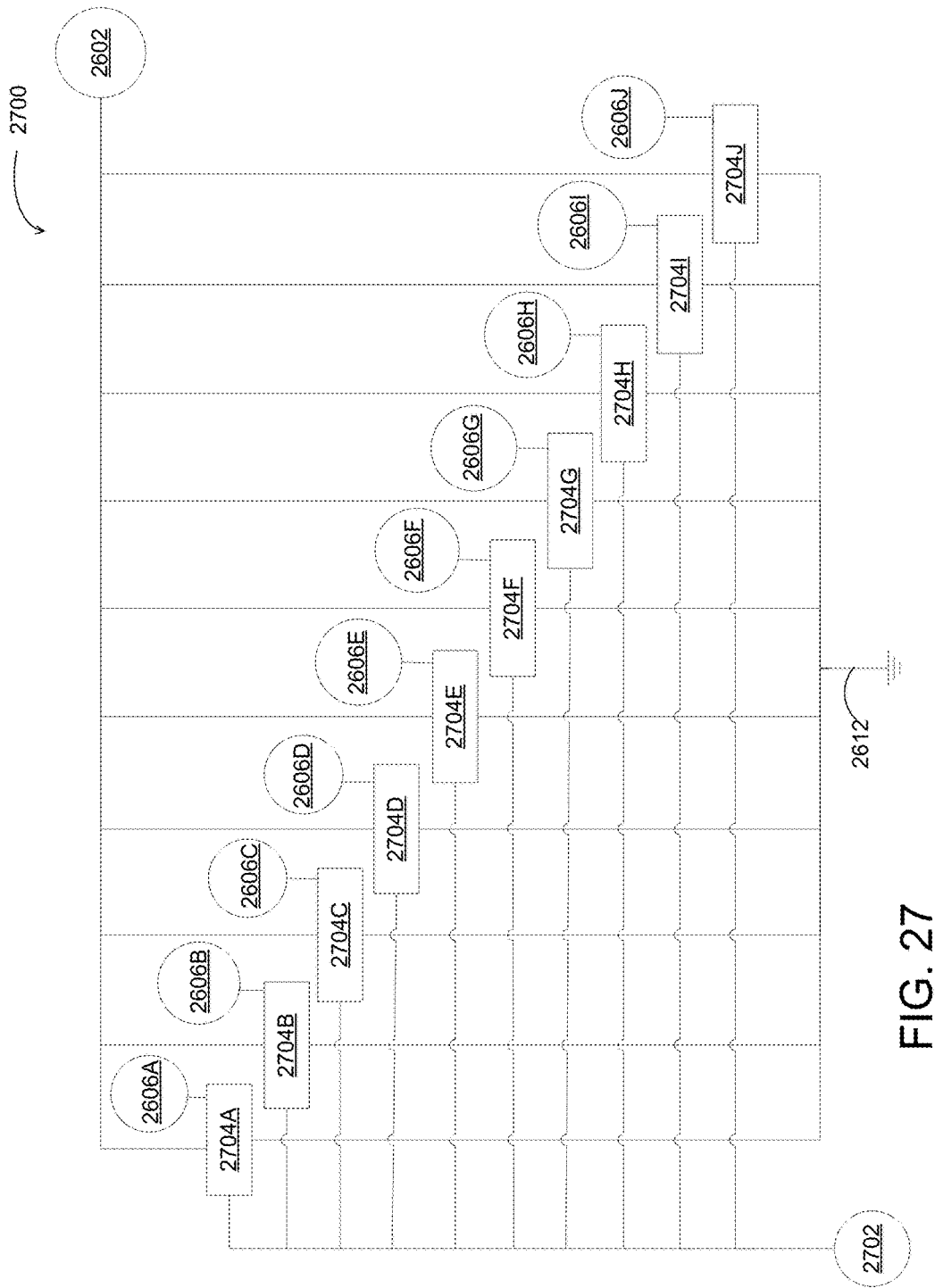
FIG. 27 is a schematic diagram illustrating a solid state switching system that may be implemented in the controller of FIGS. 25A-25H or the controller of FIGS. 15C-15D.

FIG. 27 is a schematic diagram illustrating a solid state switching system 2700 that may be implemented in the controller 2500 of FIGS. 25A-25H or the controller 100 of FIGS. 15C-15D. In contrast with the mechanical switching system 2600 of FIG. 26, the solid state switching system 2700 is actuated without use of any physically moving parts. The solid state switching system 2700 may include the source contact 2602, a selector contact 2702 connected with a signal source, solid state switches 2704A-J, the electrode contacts 2606A-J, and ground 2612. The electrode contacts 2606A-J are each connected with the different electrodes 2608A-J that may be used for ablation. The source contact 2602 may be connected with the source of RF energy at a level sufficient for ablation. The solid state switching system may set the selector contact 2702 to a particular signal (such as to a particular voltage level) that causes a particular solid state switch 2704A-J to connect the source contact 2602 with a particular electrode contact 2606A-J. For example, the solid state switching system may set the selector contact 2702 to a voltage level which activates solid state switch 2704J to connect the source contact 2602 with the electrode contact 2606J, thereby providing RF energy at a level sufficient for ablation to the electrode associated with the electrode contact 2606J. Also, the other solid state switches 2604A-I may maintain a connection between their associated electrode contacts 2606A-I and ground 2612 while the solid state switch 2604J connects the source contact 2602 to the electrode contact 2606J. The solid state switches may be implemented using any type of solid state device, including MOSFETs, IGBTs, bipolar transistors, and thyristors.

Figure 28:
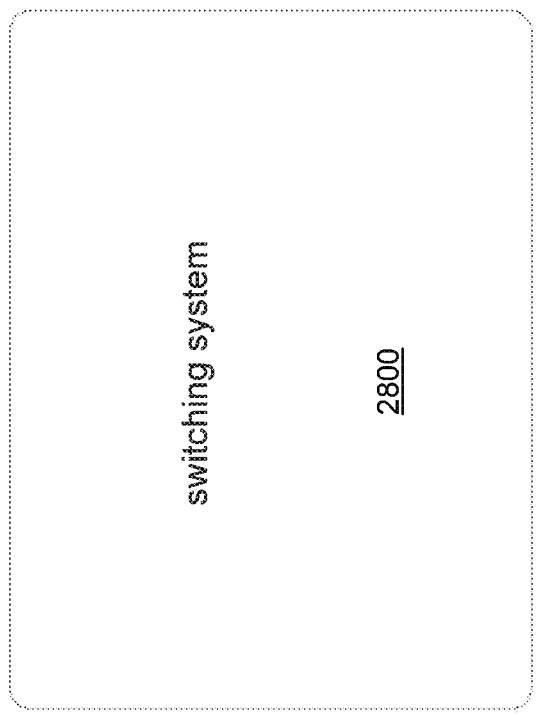
FIG. 28 is a diagram illustrating a generic switching system that may be implemented in the controller of FIGS. 25A-25H or the controller of FIGS. 15C-15D.

FIG. 28 is a diagram illustrating a generic switching system 2800 that may be implemented in the controller 2500 of FIGS. 25A-25H or the controller 100 of FIGS. 15C-15D. The generic switching system 2800 may implement any type of switching system to connect the source contact 2602 to a particular electrode contact 2606A-J. For example, the generic switching system may be implemented using mechanical switches, solid state switches, or a combination of mechanical and solid state switches.

As used herein, the term "animal" is intended to include human beings and other animals such canines, other mammals, etc. As used herein, the terms "live", "living", "live animal" are intended to exclude methods of euthanasia, surgery performed on dead animals including dissection and autopsies, or other techniques for disposing of dead bodies.

While at least a plurality of different embodiments are disclosed herein, it should be appreciated that a vast number of variations exist. It should also be appreciated that the embodiments described herein are not intended to limit the scope, applicability, or configuration of the claimed subject matter in any way. Rather, the foregoing detailed description will provide those skilled in the art with a convenient road map for implementing the described embodiments. It should be understood that various changes can be made in the function and arrangement of elements or steps without departing from the scope defined by the claims, which includes known equivalents and foreseeable equivalents at the time of filing this patent application.

What is claimed is:

1. A device for ablating a target tissue of a patient, the device comprising:
    a catheter body comprising a proximal end and a terminal distal end;
    an elliptical ring coupled to the terminal distal end of the catheter body, the elliptical ring having a major axis and a minor axis, wherein the minor axis divides the elliptical ring into a first portion and a second portion, the first portion encompassing an apex of the major axis; and
    a plurality of electrodes supported by the elliptical ring, wherein a number of the plurality of electrodes supported by the first portion of the elliptical ring exceeds a number of the plurality of electrodes supported by the second portion of the elliptical ring, and
    wherein at least one electrode of the plurality of electrodes is disposed over the apex of the major axis.

2. The device according to claim 1, wherein the major axis comprises a first diameter and the minor axis comprises a second diameter, and wherein the first diameter is 5 mm longer than the second diameter.

3. The device according to claim 1, wherein the plurality of electrodes straddle both sides of the apex of the major axis.

4. The device according to claim 1, wherein the distal end of the catheter body is flexible, and wherein the elliptical ring is orthogonal to the distal end.

5. The device according to claim 1, wherein the elliptical ring is planar.

6. The device according to claim 1, wherein the elliptical ring comprises a curve of less than 360 degrees.

7. The device according to claim 1, wherein the plurality of electrodes comprises a first electrode of a first length, a second electrode of a second length different than the first length, and a third electrode of a third length different than the first length and different than the second length.

8. The device according to claim 7, wherein the first, second, and third electrodes are substantially coplanar.

9. The device according to claim 7, wherein the elliptical ring comprises a curve of less than 360 degrees and greater than 270 degrees.

10. The device according to claim 7, wherein the first length is about 4 mm.

11. The device according to claim 10, wherein the second length is at least 3 mm and is less than the first length.

12. The device according to claim 11, wherein the third length is at least 2 mm and is less than the second length.

13. The device according to claim 7, wherein the first electrode is separated from the second electrode and the third electrode by an equal distance.

14. The device according to claim 1, wherein the major axis comprises a first diameter having a length from about 25 mm to about 50 mm, and wherein the minor axis comprises a second diameter shorter than the first diameter and having a length of about 20 mm to about 45 mm.

15. The device according to claim 14, wherein the length of the second diameter is about 10% to about 20% shorter than the length of the first diameter.

* * * * *